United States Patent
Morsey et al.

(10) Patent No.: US 10,550,194 B2
(45) Date of Patent: Feb. 4, 2020

(54) PD-L1 ANTIBODIES BINDING CANINE PD-L1

(71) Applicant: Intervet Inc., Madison, NJ (US)

(72) Inventors: Mohamad Morsey, Omaha, NE (US); Yuanzheng Zhang, Edison, NJ (US); Denise Bartels-Morozov, Fremont, NE (US); Jason Erskine, Omaha, NE (US); Ian Tarpey, St. Ives (GB)

(73) Assignee: Intervet Inc., Madison, NJ (US)

( * ) Notice: Subject to any disclaimer, the term of this patent is extended or adjusted under 35 U.S.C. 154(b) by 179 days.

(21) Appl. No.: 15/514,920

(22) PCT Filed: Sep. 29, 2015

(86) PCT No.: PCT/EP2015/072324
§ 371 (c)(1),
(2) Date: Mar. 28, 2017

(87) PCT Pub. No.: WO2016/050721
PCT Pub. Date: Apr. 7, 2016

(65) Prior Publication Data
US 2018/0237535 A1 Aug. 23, 2018

Related U.S. Application Data

(60) Provisional application No. 62/057,541, filed on Sep. 30, 2014, provisional application No. 62/172,511, filed on Jun. 8, 2015.

(51) Int. Cl.
*C07K 16/28* (2006.01)
*A61K 39/00* (2006.01)

(52) U.S. Cl.
CPC .......... *C07K 16/2896* (2013.01); *A61K 39/00* (2013.01); *C07K 2317/24* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,703,360 B2 | 3/2004 | McCall et al. | |
| 7,595,048 B2 | 9/2009 | Honjo et al. | |
| 7,807,158 B2 | 10/2010 | Endl et al. | |
| 8,008,449 B2 | 8/2011 | Korman et al. | |
| 8,337,842 B2 | 12/2012 | Hansen | |
| 8,354,509 B2 | 1/2013 | Carven et al. | |
| 8,569,460 B2 | 10/2013 | Hansen | |
| 8,652,470 B2 | 2/2014 | Hansen | |
| 9,580,496 B2 | 2/2017 | Gearing | |
| 9,616,120 B2 | 4/2017 | Hansen | |
| 9,790,280 B2 | 10/2017 | Rue et al. | |
| 10,280,223 B2 | 5/2019 | Mizuno | |
| 2016/0039903 A1* | 2/2016 | Ring | C07K 14/70503 424/1.69 |
| 2016/0333096 A1 | 11/2016 | Morsey et al. | |

FOREIGN PATENT DOCUMENTS

| | | |
|---|---|---|
| EP | 1836226 B1 | 6/2011 |
| EP | 2705057 B1 | 3/2016 |
| WO | 1999051642 A1 | 10/1999 |
| WO | 2010110838 A2 | 9/2010 |
| WO | 2010117448 A2 | 10/2010 |
| WO | 2012153121 A1 | 11/2012 |
| WO | 2012153122 A1 | 11/2012 |
| WO | 2012153123 A1 | 11/2012 |
| WO | 2013030568 A1 | 3/2013 |
| WO | 2013034900 A1 | 3/2013 |
| WO | 2013063186 A2 | 5/2013 |
| WO | WO2013079174 A1 | 6/2013 |
| WO | WO2015091910 A2 | 6/2015 |
| WO | WO2015091911 | 6/2015 |
| WO | WO2015091914 | 6/2015 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
Brown et al (JI, 156:3285-3291, 1996).*
Kuroda et al (Proteins, 75:139-146, 2009).*
Al-Lazikani, Standard Conformations for the Canonical Structures of Immunoglobulins, J. Mol. Biol., 1997, 927-948, 273.
Alegre, A non-activating "humanized" anti-CD3 monoclonal antibody retains immunosuppressive properties in vivo, Transplantation, 1994, 1537-1543, 57.
Barber, Restoring function in exhausted CD8T cells during chronic viral infection, Nature, 2006, 682-687, 439.
Brown, Blockade of Programmed Death-1 Ligands on Dendritic Cells Enhances T Cell Activation and Cytokine Production, J. Immunol., 2003, 1257-1266, 170.
Chothia, Canonical Structures for the Hypervariable Regions of Immunoglobins, J. Mol. Biol., 1987, 901-917, 196.
Chothia, Conformations of immunoglobin hypervariable regions, Nature, 1989, 877-883, 342.
Dong et al., Tumor-associated B7-H1 promotes T-cell apoptosis: A potential mechanism of immune evasion, Nature Medicine, 2002, 793-800, 8(8).

(Continued)

Primary Examiner — Brad Duffy

(57) ABSTRACT

The present disclosure describes antibodies including caninized antibodies against canine PD-L1 with specific properties. The document relates to epitopes of canine PD-L1 that bind to these antibodies, as well as to anti-canine PD-L1 antibodies that bind these epitopes, and to the use of the caninized anti-canine PD-L1 antibodies in the treatment of cancer in dogs.

12 Claims, 2 Drawing Sheets
Specification includes a Sequence Listing.

(56) References Cited

OTHER PUBLICATIONS

Hao, Epitope Characterization of an anti-PD-L1 antibody using orthogonal approaches, Journal of Molecular Recognition, 2015, 269-276, 28.
Hutchins, Improved bio distribution, tumor targeting and reduced immunogenicity in mice with a gamma 4 variant of CAMPATH-1H, Proc. Natl. Acad. Sci. USA, 1995, pp. 11980-11984, 92.
International Search Report for PCTEP2015072324 dated Jan. 20, 2016, 5 pages.
Iwai, Involvement of PD-L1 on tumor cells in the escape from host immune system and tumor immunotherapy by PD-L1 blockade, Proc. Natl. Acad. Sci., 2002, 12293-12297, 99.
Kabat, The Structural Basis of Antibody Complementarity, Adv. Prot. Chem., 1978, 1-75, 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.
Lin, The PD-1/PD-L1 complex resembles the antigen-binding Fv domains of antibodies and T cell receptors, Proc. Nat. Acad. Sci., 2008, 3011-3016, 105.
McEarchern, Engineered anti-CD70 antibody with multiple effector functions exhibits in vitro and in vivo antitumor activities, Blood, 2007, 1185-1192, 109.
Nomi et al., Clinical Significance and Therapeutic Potential of the Programmed Death-1 Ligand/Programmed Death-1 Pathway in Human Pancreatic Cancer, Clinical Cancer Research, 2007, 2151-2157, 13.
Okazaki, PD-1 and PD-1 ligands: from discovery to clinical application, Int. Immunol., 2007, 813-824, 19.
Sazinsky, Aglycosylated immunoglobin G1 variants productively engage activating Fc receptors, Proc. Natl. Acad. Sci., 2008, 20167-20172, 105.
Shields, High Resolution Mapping of the Binding Site on Human IgG1 for FcγRI, FcγRII, FcγRIII, and FcRn and Design of IgG1 Variants with Improved Binding to the FcγR, J. of Biol. Chem., 2001, 6591-6604, 276-9.
Strome, B7-H1 Blockade Augments Adoptive T-Cell Immunotherapy for Squamous Cell Cancinoma, Cancer Research, 2003, 6501-6505, 63.
Tang et al., Cloning and characterization of cDNAs encoding four different canine immunoglobulin Y chains, Veterinary Immunology and Immunopathology, 2001, pp. 259-270, 80.
Thompson et al., PD-1 Is Expressed by Tumor-Infiltrating Immune Cells and Is Associated with Poor Outcome for Patients with Renal Cell Carcinoma, Clinical Cancer Research, 2007, 1757-1761, 15.
Thompson et al., Tumor B7-H1 Is Associated with Poor Prognosis in Renal Cell Carcinoma Patients with Long-Term Follow-up, Cancer Res., 2006, 3381-3385, 66.
Tsushima, Predominant expression of B7-H1 and its immunoregulatory roles in oral squamous cell carcinoma, Oral Oncol., 2006, 268-274, 42.
Wintterle, Expression of the B7-Related Molecule B7-H1 by Glioma Cells: A Potential Mechanism of Immune Paralysis, Caner Res., 2003, 7462-7467, 63.
Zang, Structural and Functional Analysis of the Costimulatory Receptor Programmed Death-1, Immunity, 2004, 337-347, 20.
Baudino et al., Crucial Role of aspartic acid at position 265 in the CH2 domain for muri e IgG2a and IgG2b Fc-assiciated effector functions, J. Immunology, 2008, pp. 6664-6669, vol. 181.
Dorai, H et al., Aglycosylated chimeric mouse/human IgG1 antibody retains some effector function, Hybridoma, 1991, pp. 211-217, 10(2).
Lund et al., J. Immunol., J. Immunol., 1996, pp. 4963-4969, 157.
Mimura, Y et al., Glycosylation engineering of therapeutic IgG antibodies: challenges for the safety, functionality and efficacy, Protein Cell, 2018, pp. 47-62, 9(1).
Tao et al., J. Immunol., Journal of Immunology, 1989, pp. 2595-2601, 143.
Shosu, Kazuha, Production of monoclonal antibodies against PD-1 and PD-L1 in dogs and analysis of their functions, 157th Abstracts of lectures of the Japan Society of Veterinary Medicine, 2014, 483, English translation, HSO-26.
Shosu, Kazuha, Production of monoclonal antibodies against PD-1 and PD-L1 in dogs and analysis of their functions, 157th Abstracts of lectures of the Japan Society of Veterinary Medicine, 2014, 483, HSO-26.

* cited by examiner

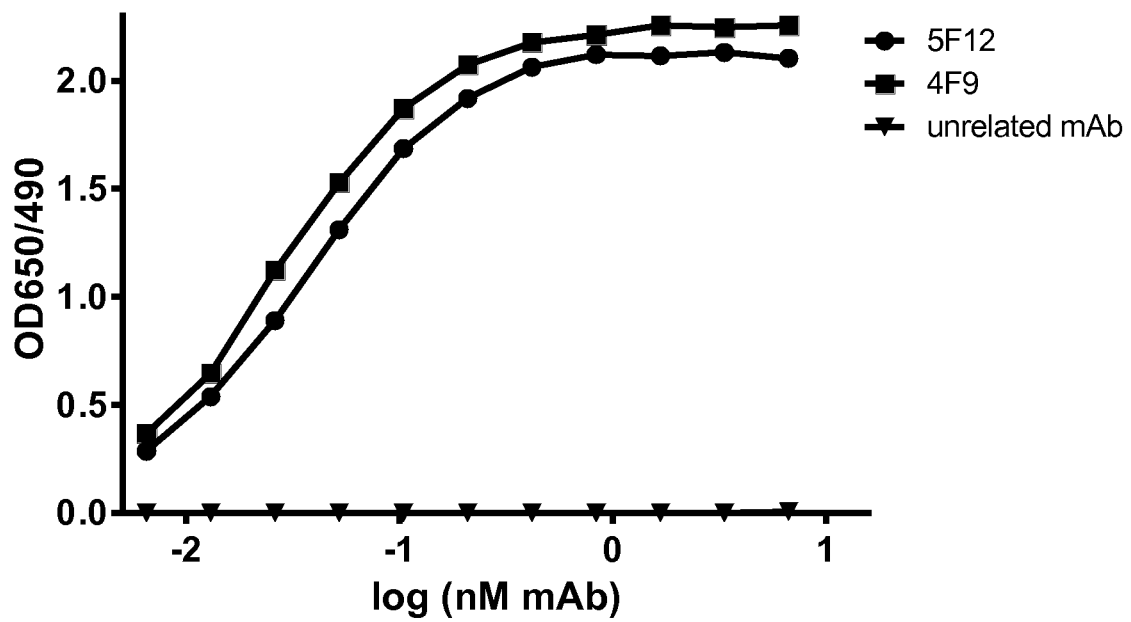
Figure 1 shows the ELISA results for reactivity of two mouse anti-canine PDL-1 mAbs against canine PDL-1, as a function of OD 650/490 versus the log mAb (nM). Both mAbs, designated 4F9 and 5F12, demonstrate strong and dose-dependent binding to canine PDL-1.

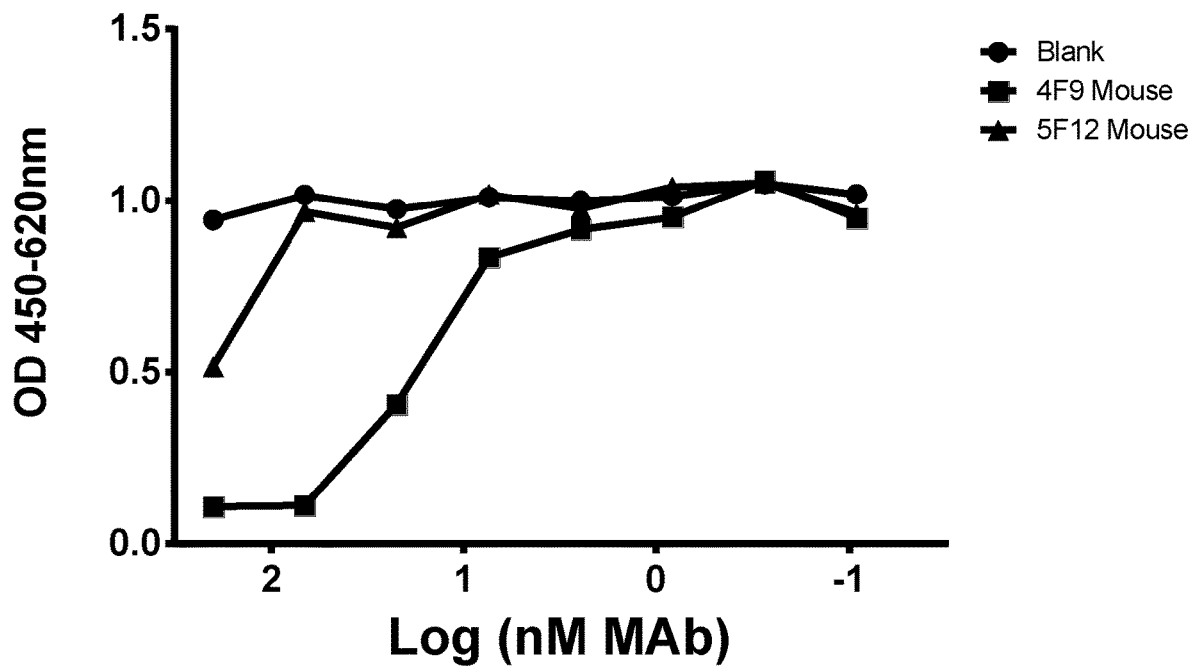
Figure 2 shows ligand blockade with mouse anti-canine PDL-1 mAbs. Two mAbs designated 4F9 and 5F12 were tested for their ability to inhibit binding of PDL-1 to PD-1 expressed on CHO cells. Both mAbs blocked the binding of PDL-1 to PD-1, although mAb 4F9 is a stronger inhibitor than 5F12.

PD-L1 ANTIBODIES BINDING CANINE PD-L1

CROSS-REFERENCE TO RELATED APPLICATIONS

This application is a national stage entry under 35 U.S.C. § 371 of PCT/EP2015/072324 filed on Sep. 29, 2015, which claims priority to U.S. Application No. 62/057,541 filed on Sep. 30, 2014 and U.S. Application No. 62/172,511 filed on Jun. 8, 2015. The content of PCT/EP2015/072324 is hereby incorporated by reference in its entirety.

FIELD OF THE INVENTION

The present invention relates to anti-canine PD-L1 antibodies with specific properties. The present invention also relates to caninized antibodies against canine PD-L1 that have specific sequences and a high binding affinity for canine PD-L1. The present invention further relates to epitopes of canine PD-L1 that bind to these antibodies, as well as to anti-canine PD-L1 antibodies that bind these epitopes. The invention further relates to use of the antibodies of the present invention in the treatment of dogs, including cancer treatment.

BACKGROUND OF THE INVENTION

An immunoinhibitory receptor that is primarily expressed on activated T and B cells, Programmed Cell Death Receptor 1, also referred to as Programmed Death Receptor 1 (PD-1), is a member of the immunoglobulin superfamily related to CD28 and cytotoxic T-lymphocyte associated protein-4 (CTLA-4). PD-1 and like family members are type I transmembrane glycoproteins containing an extracellular Ig Variable-type (V-type) domain that binds its ligands and a cytoplasmic tail that binds signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

PD-1 attenuates T-cell responses when bound to Programmed Cell Death Ligand 1, also referred to as Programmed Death Ligand 1 (PD-L1), and/or Programmed Cell Death Ligand 2, also referred to as Programmed Death Ligand 2 (PD-L2). The binding of either of these ligands to PD-1 negatively regulates antigen receptor signaling. Blocking the binding of PD-L1 to PD-1 enhances tumor-specific CD8+ T-cell immunity, while aiding the clearance of tumor cells by the immune system. The three-dimensional structure of murine PD-1, as well as the co-crystal structure of mouse PD-1 with human PD-L1 have been reported [Zhang et al., *Immunity* 20: 337-347 (2004); Lin et al., *Proc. Natl. Acad. Sci. USA* 105: 3011-3016 (2008)].

PD-L1 and PD-L2 are type I transmembrane ligands that contain both IgV- and IgC-like domains in the extracellular region along with short cytoplasmic regions with no known signaling motifs. Both PD-L1 and PD-L2 are either constitutively expressed or can be induced in a variety of cell types, including non-hematopoietic tissues as well as various tumor types. PD-L1 is not only expressed on B, T, myeloid and dendritic cells (DCs), but also on peripheral cells, such as microvascular endothelial cells and non-lymphoid organs e.g., heart or lung. In contrast, PD-L2 is only found on macrophages and DCs. The expression pattern of PD-1 ligands suggests that PD-1 plays a role in maintaining peripheral tolerance and may further serve to regulate self-reactive T- and B-cell responses in the periphery.

In any case, it is now abundantly clear that PD-1 and PD-L1 play critical roles in at least certain human cancers, presumably by mediating immune evasion. Accordingly, PD-L1 has been shown to be expressed on a number of mouse and human tumors and is inducible by IFN-γ in the majority of PD-L1 negative tumor cell lines [Iwai et al., *Proc. Natl. Acad. Sci. U.S.A.* 99: 12293-12297 (2002); Strome et al., *Cancer Res.*, 63: 6501-6505 (2003)]. Furthermore, the expression of PD-1 on tumor infiltrating lymphocytes and/or PD-L1 on tumor cells has been identified in a number of primary human tumor biopsies. Such tumor tissues include cancers of the lung, liver, ovary, cervix, skin, colon, glioma, bladder, breast, kidney, esophagus, stomach, oral squamous cell, urothelial cell, and pancreas, as well as tumors of the head and neck [Brown et al., *J. Immunol.* 170: 1257-1266 (2003); Dong et al., *Nat. Med.* 8: 793-800 (2002); Wintterle et al., *Cancer Res.* 63: 7462-7467 (2003); Strome et al., *Cancer Res.*, 63: 6501-6505 (2003); Thompson et al., *Cancer Res.* 66: 3381-5 (2006); Thompson et al., *Clin. Cancer Res.* 13: 1757-1761 (2007); Nomi et al., *Clin. Cancer Res.* 13: 2151-2157. (2007)]. More strikingly, PD-ligand expression on tumor cells has been correlated to poor prognosis of human cancer patients across multiple tumor types [reviewed in Okazaki and Honjo, *Int. Immunol.* 19: 813-824 (2007)].

Moreover, Nomi et al. [*Clin. Cancer Res.* 13: 2151-2157 (2007)] demonstrated the therapeutic efficacy of blocking the binding of PD-L1 to PD-1 in a murine model of aggressive pancreatic cancer through administering either PD-1 or PD-L1 directed antibody. These antibodies effectively promoted tumor reactive CD8+ T cell infiltration into the tumor resulting in the up-regulation of anti-tumor effectors including IFN-γ, granzyme B, and perforin. Similarly, the use of antibodies to block the binding of PD-L1 and PD-1 significantly inhibited tumor growth in a model of mouse squamous cell carcinoma [Tsushima et al., *Oral Oncol.* 42: 268-274 (2006)].

In other studies, transfection of a murine mastocytoma line with PD-L1 led to decreased lysis of the tumor cells when co-cultured with a tumor-specific CTL clone. Lysis was restored when anti-PD-L1 monoclonal antibody was added [Iwai et al., *Proc. Natl. Acad. Sci. U.S.A.* 99: 12293-12297 (2002)]. In vivo, blocking the PD1/PD-L1 interaction was shown to increase the efficacy of adoptive T cell transfer therapy in a mouse tumor model [Strome et al., *Cancer Res.* 63: 6501-6505 (2003)]. Further evidence for the role of PD-1 and PD-L1 in cancer treatment comes from experiments performed with PD-1 knockout mice in which PD-L1 expressing myeloma cells grew only in wild-type animals (resulting in tumor growth and associated animal death), but not in PD-1 deficient mice [Iwai Y. et al., *Proc. Natl. Acad. Sci. U.S.A.* 99: 12293-12297 (2002)]. More recently, humanized murine monoclonal antibodies against human PD-1 have shown initial success in cancer therapy in humans [see e.g., U.S. Pat. No. 8,354,509 B2, U.S. Pat. No. 8,008,449 B2, and U.S. Pat. No. 7,595,048 B2].

Anti-PD-L1 antibodies may also be useful in chronic viral infection. Memory CD8+ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen.

Although functional effector T cells are initially generated during the early stages of infection, they gradually lose function during the course of a chronic infection. Barber et al. [*Nature* 439: 682-687 (2006)] showed that mice infected with a laboratory strain of LCMV developed chronic infection resulted in high levels of virus in the blood and other tissues. These mice initially developed a robust T cell response, but eventually succumbed to the infection upon T cell exhaustion. Barber et al. found that the decline in number and function of the effector T cells in chronically infected mice could be reversed by injecting an antibody that blocked the interaction between PD-1 and PD-L1.

Canine antibodies (also referred to as immunoglobulin G or IgG) are large tetrameric proteins of about 150 Kd. Each IgG protein is composed of two identical light chains of about 25 Kd each, and two identical heavy chains of about 50 Kd each. There are four known IgG heavy chain subclasses of canine IgG and they are referred to as IgGA, IgGB, IgGC, and IgGD. There are two types of light chains; kappa and lambda chains. Each of the kappa or lambda light chains is composed of one variable domain (VL) and one constant domain (CL). Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region". In humans, IgG exists in one of four subclasses referred to as IgG1, IgG2, IgG3, and IgG4. The subclass of IgG is determined largely by the sequence of the hinge region, which differs among the four subclasses of IgG. The two heavy chains are linked to each other by disulfide bonds and each heavy chain is linked to one of the light chains also through a disulfide bond.

Digestion of IgG antibodies with the enzyme papain breaks the antibody molecule in the hinge region and results in the formation of three fragments. Two of these fragments are identical and each consists of the light chain held together with the VH and CH1 domains of the heavy chain. These fragments are called the "Fab" fragments and they contain the antigen binding sites of the antibody. The third fragment that results from digestion with papain is called the "Fc" and it contains the remainder of the two heavy chains held together by disulfide bonds. The Fc thus contains a dimer consisting of the CH2 and CH3 domain of each of the two heavy chains. While the Fab enables the antibody to bind to its cognate epitope, the Fc enables the antibody to mediate immune effector functions such as antibody dependent cellular cytotoxicity (ADCC), antibody-dependent phagocytosis (ADCP) and complement dependent cytotoxicity (CDC).

It is well known in the art that IgG antibodies mediate effector functions such as ADCC and ADCP through binding of their Fc portion to a family of proteins known as $Fc_\gamma$ receptors, whereas CDC is mediated through the binding of the Fc to the first component of complement, C1q. It is also well known in the art that different IgG sub-classes differ in their capacity to mediate these effector functions. For example, human IgG1 displays strong ADCC and CDC, whereas IgG4 displays a weak to no ADCC and CDC. In addition, methods for identification of which IgG subclasses display or lack effector functions are well known in the art.

Approaches that rely on use of monoclonal antibodies for therapeutic purposes require the design of fit-for-purpose antibodies or antibody fragments to achieve the desired therapeutic response. For example, some therapeutic approaches for cancer require the therapeutic antibodies to have enhanced effector functions, while others require the effector functions to be significantly reduced or eliminated altogether. Enhancement or elimination of effector functions may be achieved through introduction of one or more amino acid mutations (substitutions) in the Fc portion of the antibody so as to enhance or reduce binding to $Fc_\gamma$ receptors and the first component of complement. There are numerous reports in the prior art describing amino acid substitutions that may be introduced into an antibody molecule in order to modulate its effector functions. For example, Shields et al., [*J. of Biol. Chem.*, 276 (9): 6591-6604 (2001)] disclosed that an asparagine to alanine (N297A) substitution, which result in a non-glycosylated antibody, significantly reduced antibody binding to several $Fc_\gamma$ receptors. Additionally, Shields et al., disclosed that an aspartic acid-to-alanine (D265A) substitution also significantly reduced binding of the antibody to $Fc_\gamma$ receptors. Each of the N297A and D265A substitutions were also shown to significantly impair CDC. There are other similar reports identifying potential substitutions to reduce or eliminate effector function in antibodies [e.g., Sazinsky et al., *Proc. Nat. Acad. Sci.*, 105:20167-20172 (2008), Alegre et al., *Transplantation*, 57:1537-1543 (1994), Hutchins et al., *Proc. Nat. Acad. Sci.* 92:11980-11984 (1994), McEarchem et al., *Blood*, 109:1185-1192 (2007)].

The citation of any reference herein should not be construed as an admission that such reference is available as "prior art" to the instant application.

SUMMARY OF THE INVENTION

The present invention provides antibodies and antigen binding fragments thereof (including isolated antibodies and isolated antigen binding fragments thereof) that bind canine Programmed Death Ligand 1 (canine PD-L1) with specificity. In particular embodiments the antibodies and the fragments thereof are mammalian antibodies. In more particular embodiments the mammalian antibodies are murine (i.e., mouse) antibodies. In a related aspect of the present invention the isolated antibodies are caninized antibodies. In specific embodiments the caninized antibodies are caninized mammalian (e.g., mouse) anti-canine PD-L1 antibodies. The antibodies and antigen binding fragments thereof of the present invention bind canine PD-L1 and can block the binding of canine PD-L1 to canine Programmed Death Receptor 1 (PD-1). The present invention further provides the use of such antibodies or antigen binding fragments thereof in the treatment of disease, e.g., the treatment of cancer in canines.

In particular embodiments the antibodies or antigen binding fragments thereof that bind canine PD-L1 with specificity comprise three light chain complementary determining regions (CDRs): CDR light 1 (CDRL1), CDR light 2 (CDRL2), and CDR light 3 (CDRL3); and three heavy chain CDRs: CDR heavy 1 (CDRH1), CDR heavy 2 (CDRH2) and CDR heavy 3 (CDRH3).

In certain embodiments the CDRH1 comprises the amino acid sequence of SEQ ID NO: 13. In other embodiments the CDRH1 comprises a conservatively modified variant of SEQ ID NO: 13. In yet other embodiments the CDRH1 comprises a variant (e.g., a function-conservative variant) of SEQ ID NO: 13 that comprises the canonical structure class of 1. In still other embodiments the CDRH1 comprises an amino acid sequence of SEQ ID NO: 19. In yet other embodiments the CDRH1 comprises a conservatively modified variant of SEQ ID NO: 19. In still other embodiments the CDRH1 comprises a variant (e.g., a function-conservative variant) of SEQ ID NO: 19 that comprises the canonical structure class of 1.

In certain embodiments the CDRH2 comprises the amino acid sequence of SEQ ID NO: 14. In other embodiments the CDRH2 comprises a conservatively modified variant of SEQ ID NO: 14. In still other embodiments the CDRH2 comprises a variant (e.g., a function-conservative variant) of SEQ ID NO: 14 that comprises the canonical structure class of 3B. In yet other embodiments the CDRH2 comprises the amino acid sequence of SEQ ID NO: 20. In still other embodiments the CDRH2 comprises a conservatively modified variant of SEQ ID NO: 20. In yet other embodiments the CDRH2 comprises a variant (e.g., a function-conservative variant) of SEQ ID NO: 20 that comprises the canonical structure class of 3B.

In certain embodiments the CDRH3 comprises the amino acid sequence of SEQ ID NO: 15. In other embodiments the CDRH3 comprises a conservatively modified variant of SEQ ID NO: 15. In still other embodiments the CDRH3 comprises a variant (e.g., a function-conservative variant) of SEQ ID NO: 15 that comprises the canonical structure class of 10. In yet other embodiments the CDRH3 comprises the amino acid sequence of SEQ ID NO: 21. In still other embodiments the CDRH3 comprises a conservatively modified variant of SEQ ID NO: 21. In yet other embodiments the CDRH3 comprises a variant (e.g., a function-conservative variant) of SEQ ID NO: 21 that comprises the canonical structure class of 8.

In certain embodiments the CDRL1 comprises the amino acid sequence of SEQ ID NO: 16. In other embodiments the CDRL1 comprises a conservatively modified variant of SEQ ID NO: 16. In still other embodiments the CDRL1 comprises a variant (e.g., a function-conservative variant) of SEQ ID NO: 16 that comprises the canonical structure class of 2. In yet other embodiments the amino acid sequence of the CDRL1 comprises SEQ ID NO: 22. In still other embodiments the CDRL1 comprises a conservatively modified variant of SEQ ID NO: 22. In yet other embodiments the CDRL1 comprises a variant (e.g., a function-conservative variant) of SEQ ID NO: 22 that comprises the canonical structure class of 3.

In certain embodiments the CDRL2 comprises the amino acid sequence of SEQ ID NO: 17. In other embodiments the CDRL2 comprises a conservatively modified variant of SEQ ID NO: 17. In still other embodiments the CDRL2 comprises a variant (e.g., a function-conservative variant) of SEQ ID NO: 17 that comprises the canonical structure class of 1. In yet other embodiments the CDRL2 comprises SEQ ID NO: 23. In still other embodiments the CDRL2 comprises a conservatively modified variant of SEQ ID NO: 23. In yet other embodiments the CDRL2 comprises a variant (e.g., a function-conservative variant) of SEQ ID NO: 23 that comprises the canonical structure class of 1.

In certain embodiments the CDRL3 comprises the amino acid sequence of SEQ ID NO: 18. In other embodiments the CDRL3 comprises a conservatively modified variant of SEQ ID NO: 18. In still other embodiments the CDRL3 comprises a variant (e.g., a function-conservative variant) of SEQ ID NO: 18 that comprises the canonical structure class of 1. In yet other embodiments the CDRL3 comprises the amino acid sequence of SEQ ID NO: 24. In still other embodiments the CDRL3 comprises a conservatively modified variant of SEQ ID NO: 24. In still other embodiments the CDRL3 comprises a variant (e.g., a function-conservative variant) of SEQ ID NO: 24 that comprises the canonical structure class of 1.

The present invention further provides combinations of two or more of the CDRs of the present invention (or variants thereof) in a given antibody, e.g., a CDRH3 that comprises the amino acid sequence of SEQ ID NO: 15 and a CDRL3 that comprises the amino acid sequence of SEQ ID NO: 18.

In specific embodiments the antibodies and antigen binding fragments thereof that bind canine PD-L1 comprise a CDRH1 that comprises an amino acid sequence of SEQ ID NO: 13, a conservatively modified variant of SEQ ID NO: 13, or a variant (e.g., a function-conservative variant) of SEQ ID NO: 13 that comprises the canonical structure class of 1; a CDRH2 that comprises the amino acid sequence of SEQ ID NO: 14, a conservatively modified variant of SEQ ID NO: 14, or a variant (e.g., a function-conservative variant) of SEQ ID NO: 14 that comprises the canonical structure class of 3B; a CDRH3 that comprises SEQ ID NO: 15, a conservatively modified variant of SEQ ID NO: 15, or a variant (e.g., a function-conservative variant) of SEQ ID NO: 15 that comprises the canonical structure class of 10; a CDRL1 that comprises an amino acid sequence of SEQ ID NO: 16, a conservatively modified variant of SEQ ID NO: 16, or a variant (e.g., a function-conservative variant) of SEQ ID NO: 16 that comprises the canonical structure class of 2; a CDRL2 that comprises the amino acid sequence of SEQ ID NO: 17, a conservatively modified variant of SEQ ID NO: 17 or a variant (e.g., a function-conservative variant) of SEQ ID NO: 17 that comprises the canonical structure class of 1; and a CDRL3 that comprises the amino acid sequence of SEQ ID NO: 18, a conservatively modified variant of SEQ ID NO: 18, or a variant (e.g., a function-conservative variant) of SEQ ID NO: 18 that comprises the canonical structure class of 1.

In related embodiments the antibodies and antigen binding fragments thereof that bind canine PD-L1 comprise a CDRH1 that comprises an amino acid sequence of SEQ ID NO: 19, a conservatively modified variant of SEQ ID NO: 19, or a variant (e.g., a function-conservative variant) of SEQ ID NO: 19 that comprises the canonical structure class of 1; a CDRH2 that comprises the amino acid sequence of SEQ ID NO: 20, a conservatively modified variant of SEQ ID NO: 20, or a variant (e.g., a function-conservative variant) of SEQ ID NO: 20 that comprises the canonical structure class of 3B; a CDRH3 that comprises SEQ ID NO: 21, a conservatively modified variant of SEQ ID NO: 21, or a variant (e.g., a function-conservative variant) of SEQ ID NO: 21 that comprises the canonical structure class of 8; a CDRL1 that comprises an amino acid sequence of SEQ ID NO: 22, a conservatively modified variant of SEQ ID NO: 22, or a variant (e.g., a function-conservative variant) of SEQ ID NO: 22 that comprises the canonical structure class of 3; a CDRL2 that comprises the amino acid sequence of SEQ ID NO: 23, a conservatively modified variant of SEQ ID NO: 23 or a variant (e.g., a function-conservative variant) of SEQ ID NO: 23 that comprises the canonical structure class of 1; and a CDRL3 that comprises the amino acid sequence of SEQ ID NO: 24, a conservatively modified variant of SEQ ID NO: 24, or a variant (e.g., a function-conservative variant) of SEQ ID NO: 24 that comprises the canonical structure class of 1. Accordingly, in a particular aspect of the present invention, the present invention further provides caninized anti-canine PD-L1 antibodies. In certain embodiments the caninized anti-canine PD-L1 antibodies are caninized mammalian (e.g., murine) anti-canine PD-L1 antibodies. In specific embodiments, the caninized anti-canine PD-L1 antibodies (e.g., caninized mammalian anti-canine PD-L1 antibodies, such as caninized murine anti-canine PD-L1 antibodies) comprise a cFc that has been genetically modified to augment, decrease, or eliminate one or more effector functions. In particular embodiments of this type, the genetically modified cFc decreases or eliminates one or more effector functions. In other particular embodiments the genetically modified cFc augments one or more effector function.

In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

The present invention further provides canine frames and/or full length heavy chains that comprise the genetically modified cFc regions. Accordingly, the present invention provides full length heavy chains of antibodies in which the full length heavy chains comprise the genetically modified cFc regions of the present invention and the CDRs of the present invention. Such full length heavy chains can also be combined with corresponding canine light (kappa or lambda) chains to form a complete antibody. In particular embodiments of this type, the resulting antibody binds to canine PD-L1.

In certain embodiments, the genetically modified cFc region comprises the amino acid sequence of SEQ ID NO: 66 (or SEQ ID NO: 68) in which one to seven of the following amino acid residues are replaced by another amino acid residue at the indicated positions: P4, D31, N63, G64, T65, A93, or P95. The amino acid substituting for P4, D31, N63, G64, T65, A93, and/or P95 are individually selected from one of the other 19 standard naturally occurring amino acids, as listed in Table 1 below. The present invention further provides variants of the genetically modified cFc regions that comprise an amino acid sequence that is 90%, 95%, 98%, or 99% identical to the amino acid sequence of such genetically modified cFc regions and retain at least 50%, 75%, 90%, 95%, or more of the augmentation, decrease, or elimination of the ADCC and/or the CDC as the genetically modified cFc regions comprising the amino acid sequence of SEQ ID NO: 66 (or SEQ ID NO: 68) in which one or more of the following amino acid residues were replaced: i.e., at P4, D31, N63, G64, T65, A93, or P95.

In other embodiments two to five of the following amino acid residues are replaced by another amino acid residue at the indicated positions: P4, D31, N63, G64, T65, A93, or P95. In particular embodiments of this type, the genetically modified cFc region comprises the amino acid sequence of SEQ ID NO: 66 or SEQ ID NO: 68 with the following substitutions: P4A, D31A, N63A, A93G, and P95A. In related embodiments, the genetically modified cFc region comprises the amino acid sequence of SEQ ID NO: 66 or SEQ ID NO: 68 with the following substitutions: P4A, D31A, N63A, and P95A. In other embodiments, the genetically modified cFc region comprises the amino acid sequence of SEQ ID NO: 66 or SEQ ID NO: 68 with substitutions at D31 and N63. In particular embodiments of this type, the aspartic acid residue at position 31 is replaced with a glutamic acid residue, an asparagine residue, or an alanine residue, whereas the asparagine residue at position 63 is replaced with a glutamine residue, a histidine residue, or an alanine residue. In a more particular embodiment of this type, the genetically modified cFc region comprises the amino acid sequence of SEQ ID NO: 66 or SEQ ID NO: 68 with the following substitutions: D31A and N63A. In particular embodiments, the genetically modified cFc region is encoded by the nucleotide sequence of SEQ ID NO: 65 or SEQ ID NO: 67 comprising nucleotide changes that correspond to the amino acid sequences that they encode.

In another embodiments, the genetically modified cFc region comprises the amino acid sequence of SEQ ID NO: 66 or SEQ ID NO: 68 with the substitution at A93. In a particular embodiment of this type, the substitution is A93G. In a related embodiment the the substitution is A93S. As described in U.S. provisional application No. 62/030,812, filed on Jul. 30, 2014, hereby incorporated by reference in its entirety, the substitution of A93G leads to an enhancement in complement C1q binding, which is indicative of increasing CDC activity.

In related embodiments the genetically modified cFc region further comprises a hinge region that comprises the amino acid sequence of SEQ ID NO: 45. In other embodiments the genetically modified Fc region further comprises a hinge region that comprises the amino acid sequence of SEQ ID NO: 46. In still other embodiments the genetically modified Fc region further comprises a hinge region that comprises the amino acid sequence of SEQ ID NO: 47. In yet other embodiments the genetically modified Fc region further comprises a genetically modified hinge region that comprises the amino acid sequence of SEQ ID NO: 48.

In alternative embodiments, the present invention provides a canine IgGD Fc region with a genetically modified hinge region from a canine IgGD antibody, a hinge region from a canine IgGA antibody, a hinge region from a canine IgGB antibody, or a hinge region from a canine IgGC antibody. Moreover, the present invention provides full length heavy chains of antibodies in which the full length heavy chains comprise the canine IgGD Fc region of the present invention with a genetically modified hinge region from a canine IgGD antibody, a hinge region from a canine IgGA antibody, a hinge region from a canine IgGB antibody, or a hinge region from a canine IgGC antibody. Such full length heavy chains also can be combined with corresponding canine light (kappa or lambda) chains to form a complete antibody.

Accordingly, the present invention provides a canine IgGD Fc region that further comprises a genetically modified hinge region from a canine IgGD antibody. In particular embodiments of this type the canine IgGD Fc region and genetically modified hinge region comprise the amino acid sequence of SEQ ID NO: 6 or an amino acid sequence that is 90%, 95%, 98%, or 99% identical to the amino acid sequence of SEQ ID NO: 6, which comprises a proline residue at position 10 (P10). In a more particular embodiment the canine IgGD Fc region and genetically modified hinge region is encoded by the nucleotide sequence of SEQ ID NO: 5. In other embodiments, the canine IgGD Fc region further comprises a hinge region from a canine IgGA antibody. In particular embodiments of this type the canine IgGD Fc region and hinge region comprise the amino acid sequence of SEQ ID NO: 8 or an amino acid sequence that is 90%, 95%, 98%, or 99% identical to the amino acid sequence of SEQ ID NO: 8. In a more particular embodiment the canine IgGD Fc region and hinge region is encoded by the nucleotide sequence of SEQ ID NO: 7. In still other embodiments, the canine IgGD Fc region further comprises a hinge region from a canine IgGB antibody. In particular embodiments of this type the canine IgGD Fc region and hinge region comprise the amino acid sequence of SEQ ID NO: 10 or an amino acid sequence that is 90%, 95%, 98%, or 99% identical to the amino acid sequence of SEQ ID NO: 10. In a more particular embodiment the canine IgGD Fc region and hinge region is encoded by the nucleotide sequence of SEQ ID NO: 9. In yet other embodiments, the canine IgGD Fc region further comprises a hinge region from a canine IgGC antibody. In particular embodiments of this type the canine IgGD cFc region and hinge region comprise the amino acid sequence of SEQ ID NO: 12 or an amino acid sequence that is 90%, 95%, 98%, or 99% identical to the amino acid sequence of SEQ ID NO: 12. In a more particular embodiment the canine IgGD cFc region and hinge region is encoded by the nucleotide sequence of SEQ ID NO: 11. The present invention further provides caninized antibodies that comprise these canine IgGD Fc regions and hinge regions. In a particular embodiment the caninized antibody or antigen binding fragment thereof binds canine Programmed Death Receptor 1 (canine PD-1) with specificity.

The present invention therefore provides caninized anti-canine PD-L1 antibodies with specificity and/or that have a high binding affinity for canine PD-L1. In particular embodiments, the caninized anti-canine PD-L1 antibodies also have the ability to block the binding of canine PD-L1 to canine PD-1. Such caninized antibodies or antigen binding fragments thereof that specifically bind canine PD-L1 can comprise a canine IgG heavy chain of the present invention and a canine kappa or lambda light chain. In particular embodiments the caninized anti-canine PD-L1 antibodies are caninized murine anti-canine PD-L1 antibodies. The present invention also relates to use of such caninized antibodies in the treatment of disease such as cancer and/or those due to infections.

In particular embodiments the caninized anti-canine PD-L1 antibody comprises a genetically modified cFc region of the present invention. In alternative embodiments the caninized anti-canine PD-L1 antibody comprises the canine IgGD Fc region with a genetically modified hinge region from a canine IgGD antibody, a hinge region from a canine IgGA antibody, a hinge region from a canine IgGB antibody, or a hinge region from a canine IgGC antibody. The present invention further provides such caninized anti-canine PD-L1 antibodies comprising the canine frames of the present invention in combination with CDRs obtained from mouse anti-canine PD-L1 antibodies, i.e., three light chain CDRs: CDR light 1 (CDRL1), CDR light 2 (CDRL2), and CDR light 3 (CDRL3) and three heavy chain CDRs CDR heavy 1 (CDRH1), CDR heavy 2 (CDRH2) and CDR heavy 3 (CDRH3).

In particular embodiments, the caninized murine anti-canine PD-L1 antibodies comprise the genetically modified cFc region of IgGB or IgGC of the present invention or alternatively, the canine IgGD Fc region, together with a genetically modified hinge region from a canine IgGD antibody, a hinge region from a canine IgGA antibody, a hinge region from a canine IgGB antibody, or a hinge region from a canine IgGC antibody in combination with CDRs obtained from mouse anti-canine PD-L1 antibodies. Moreover, the present invention not only provides caninized mouse anti-canine PD-L1 antibodies with specific CDRs as detailed herein, but further provides caninized mouse anti-canine PD-L1 antibodies comprising conservatively modified variants of those CDRs as well as variants that comprise (e.g., share) the same canonical structure.

Accordingly in particular embodiments the caninized anti-canine PD-L1 antibody further comprises complementary determining regions (CDRs) in which the CDRs have canonical structures of: H1-1, H2-3B, and H3-10, respectively for CDR1, CDR2, and CDR3 of the heavy chain. In even more particular embodiments, the CDRs for the corresponding light chains have canonical structures of: L1-2, L2-1, and L3-1, respectively for CDR1, CDR2, and CDR3 of the light chain. In other embodiments the caninized anti-canine PD-L1 antibody further comprises complementary determining regions (CDRs) in which the CDRs have canonical structures of: H1-1, H2-3B, and H3-8, respectively for CDR1, CDR2, and CDR3 of the heavy chain. In even more particular embodiments of this type, the CDRs for the corresponding light chains have canonical structures of: L1-3, L2-1, and L3-1, respectively for CDR1, CDR2, and CDR3 of the light chain.

In more particular embodiments, the caninized antibody of the present invention or antigen binding fragment thereof comprises one or more of the heavy chain complementary determining region 1 (VH CDR1) with an amino acid sequence of SEQ ID NO: 13 or SEQ ID NO: 19. In another embodiment, the heavy chain complementary determining region 2 (VH CDR2) comprises an amino acid sequence of SEQ ID NO: 14 or SEQ ID NO: 20. In still another embodiment the heavy chain complementary determining region 3 (VH CDR3) comprises an amino acid sequence of SEQ ID NO: 15 or SEQ ID NO: 21. In a particular embodiment of this type, the caninized antibody or antigen binding fragment comprises both a VH CDR1 comprising an amino acid sequence of SEQ ID NO: 13 or SEQ ID NO: 19 and a VH CDR2 comprising an amino acid sequence of SEQ ID NO: 14 or SEQ ID NO: 20.

In another such embodiment, the caninized antibody or antigen binding fragment comprises both a VH CDR1 comprising an amino acid sequence of SEQ ID NO: 13 or SEQ ID NO: 19 and a VH CDR3 comprising an amino acid sequence of SEQ ID NO: 15 or SEQ ID NO: 21. In yet another such embodiment, the caninized antibody or antigen binding fragment comprises both a VH CDR2 comprising an amino acid sequence of SEQ ID NO: 14 or SEQ ID NO: 20 and a VH CDR3 comprising an amino acid sequence of SEQ ID NO: 15 or SEQ ID NO: 21. In still another such embodiment, the caninized antibody or antigen binding fragment comprises a VH CDR1 comprising an amino acid sequence of SEQ ID NO: 13 or SEQ ID NO: 19, a VH CDR2 comprising an amino acid sequence of SEQ ID NO: 14 or SEQ ID NO: 20, and a VH CDR3 comprising an amino acid sequence of SEQ ID NO: 15 or SEQ ID NO: 21.

In particular embodiments, the caninized antibody or antigen binding fragment also comprises a light chain complementary determining region 1 (VL CDR1) comprising an amino acid sequence of SEQ ID NO: 16 or SEQ ID NO: 22. In related embodiments the light chain complementary determining region 2 (VL CDR2) comprises an amino acid sequence of SEQ ID NO: 17 or SEQ ID NO: 23. In still another embodiment the light chain complementary determining region 3 (VL CDR3) comprises an amino acid sequence of SEQ ID NO: 18 or SEQ ID NO: 24. In a particular embodiment of this type, the caninized antibody or antigen binding fragment comprises both a VL CDR1 comprising an amino acid sequence of SEQ ID NO: 16 or SEQ ID NO: 22 and a VL CDR2 comprising an amino acid sequence of SEQ ID NO: 17 or SEQ ID NO: 23. In another such embodiment, the caninized antibody or antigen binding fragment comprises both a VL CDR1 comprising an amino acid sequence of SEQ ID NO: 16 or SEQ ID NO: 22 and a VL CDR3 comprising an amino acid sequence of SEQ ID NO: 18 or SEQ ID NO: 24. In yet another such embodiment, the caninized antibody or antigen binding fragment comprises both a VL CDR2 comprising an amino acid sequence of SEQ ID NO: 17 or SEQ ID NO: 23 and a VL CDR3 comprising an amino acid sequence of SEQ ID NO: 18 or SEQ ID NO: 24. In still another such embodiment, the caninized antibody or antigen binding fragment comprises a VL CDR1 comprising an amino acid sequence of SEQ ID NO: 16 or SEQ ID NO: 22, a VL CDR2 comprising an amino acid sequence of SEQ ID NO: 17 or SEQ ID NO: 23, and a VL CDR3 comprising an amino acid sequence of SEQ ID NO: 18 or SEQ ID NO: 24.

The present invention further provides caninized antibodies that comprise the amino acid sequence of SEQ ID NO: 26 or that is 90%, 95%, 98%, or 99% identical to the amino acid sequence of SEQ ID NO: 26 and SEQ ID NO: 28 or that is 90%, 95%, 98%, or 99% identical to the amino acid sequence of SEQ ID NO: 28 or antigen binding fragments of these caninized antibodies. The present invention also provides caninized antibodies that comprise the amino acid sequence of SEQ ID NO: 30 or that is 90%, 95%, 98%, or 99% identical to the amino acid sequence of SEQ ID NO: 30 and SEQ ID NO: 32 or that is 90%, 95%, 98%, or 99% identical to the amino acid sequence of SEQ ID NO: 32 or antigen binding fragments of these caninized antibodies.

In particular embodiments, the heavy chain of an antibody comprises the amino acid sequence of SEQ ID NO: 26 (or 90%, 95%, 98%, or 99% identical to SEQ ID NO: 26) that comprises (i) P, A, G, or S at position 242, (ii) A, G, or S at position 269, (iii) A, G, or S at position 301, (iv) G, P, or A at position 302, (v) T, A, G, or S at position 303, (vi) A, G, or S at position 331, and (vii) P, A, G, or S at position 333. In other embodiments, the heavy chain of an antibody comprises the amino acid sequence of SEQ ID NO: 28 or 30 (or 90%, 95%, 98%, or 99% identical to SEQ ID NO: 28 or 30) that comprises (i) P, A, G, or S at position 240, (ii) A, G, or S at position 267, (iii) A, G, or S at position 299, (iv) G, P, or A at position 300, (v) T, A, G, or S at position 301, (vi) A, G, or S at position 329, and (vii) P, A, G, or S at position 331. In yet other embodiments, the heavy chain of an antibody comprises the amino acid sequence of SEQ ID NO: 32 (or 90%, 95%, 98%, or 99% identical to SEQ ID NO: 32) that comprises (i) P, A, G, or S at position 238, (ii) A, G, or S at position 265, (iii) A, G, or S at position 297, (iv) G, P, or A at position 298, (v) T, A, G, or S at position 299, (vi) A, G, or S at position 327, and (vii) P, A, G, or S at position 329.

In still other embodiments, the heavy chain of an antibody comprises the amino acid sequence of SEQ ID NO: 26 (or 90%, 95%, 98%, or 99% identical to SEQ ID NO: 26) that comprises (i) P, A, G, or S at position 242, (ii) A at position 269, (iii) A at position 301, (iv) G, P, or A at position 302, (v) T, A, G, or S at position 303, (vi) A, G, or S at position 331, and (vii) P, A, G, or S at position 333. In other embodiments, the heavy chain of an antibody comprises the amino acid sequence of SEQ ID NO: 28 or 30 (or 90%, 95%, 98%, or 99% identical to SEQ ID NO: 28 or 30) that comprises (i) P, A, G, or S at position 240, (ii) A at position 267, (iii) A at position 299, (iv) G, P, or A at position 300, (v) T, A, G, or S at position 301, (vi) A, G, or S at position 329, and (vii) P, A, G, or S at position 331. In yet other embodiments, the heavy chain of an antibody comprises the amino acid sequence of SEQ ID NO: 32 (or 90%, 95%, 98%, or 99% identical to SEQ ID NO: 32) that comprises (i) P, A, G, or S at position 238, (ii) A at position 265, (iii) A at position 297, (iv) G, P, or A at position 298, (v) T, A, G, or S at position 299, (vi) A, G, or S at position 327, and (vii) P, A, G, or S at position 329.

In still other embodiments, the heavy chain of an antibody comprises the amino acid sequence of SEQ ID NO: 26 (or 90%, 95%, 98%, or 99% identical to SEQ ID NO: 26) that comprises (i) A at position 242, (ii) A at position 269, (iii) A at position 301, (iv) P at position 302, (v) A at position 303, (vi) G, at position 331, and (vii) A, at position 333. In other embodiments, the heavy chain of an antibody comprises the amino acid sequence of SEQ ID NO: 28 or 30 (or 90%, 95%, 98%, or 99% identical to SEQ ID NO: 28 or 30) that comprises (i) A at position 240, (ii) A at position 267, (iii) A at position 299, (iv) P at position 300, (v) A at position 301, (vi) G at position 329, and (vii) A at position 331. In yet other embodiments, the heavy chain of an antibody comprises the amino acid sequence of SEQ ID NO: 32 (or 90%, 95%, 98%, or 99% identical to SEQ ID NO: 32) that comprises (i) A at position 238, (ii) A at position 265, (iii) A at position 297, (iv) P at position 298, (v) A at position 299, (vi) G at position 327, and (vii) A at position 329.

In yet other embodiments, the heavy chain of an antibody comprises the amino acid sequence of SEQ ID NO: 26 (or 90%, 95%, 98%, or 99% identical to SEQ ID NO: 26) that comprises (i) P at position 242, (ii) A, G, or S at position 269, (iii) A, G, or S at position 301, (iv) G at position 302, (v) T at position 303, (vi) A at position 331, and (vii) P at position 333. In other embodiments, the heavy chain of an antibody comprises the amino acid sequence of SEQ ID NO: 28 or 30 (or 90%, 95%, 98%, or 99% identical to SEQ ID NO: 28 or 30) that comprises (i) P at position 240, (ii) A, G, or S at position 267, (iii) A, G, or S at position 299, (iv) G at position 300, (v) T at position 301, (vi) A at position 329, and (vii) P at position 331. In yet other embodiments, the heavy chain of an antibody comprises the amino acid sequence of SEQ ID NO: 32 (or 90%, 95%, 98%, or 99% identical to SEQ ID NO: 32) that comprises (i) P at position 238, (ii) A, G, or S at position 265, (iii) A, G, or S at position 297, (iv) G at position 298, (v) T at position 299, (vi) A at position 327, and (vii) P at position 329.

In still other embodiments, the heavy chain of an antibody comprises the amino acid sequence of SEQ ID NO: 26 (or 90%, 95%, 98%, or 99% identical to SEQ ID NO: 26) that comprises (i) P at position 242, (ii) A at position 269, (iii) A at position 301, (iv) G at position 302, (v) T at position 303, (vi) A at position 331, and (vii) P at position 333. In other embodiments, the heavy chain of an antibody comprises the amino acid sequence of SEQ ID NO: 28 or 30 (or 90%, 95%, 98%, or 99% identical to SEQ ID NO: 28 or 30) that comprises (i) P at position 240, (ii) A at position 267, (iii) A at position 299, (iv) G at position 300, (v) T at position 301, (vi) A at position 329, and (vii) P at position 331. In yet other embodiments, the heavy chain of an antibody comprises the amino acid sequence of SEQ ID NO: 32 (or 90%, 95%, 98%, or 99% identical to SEQ ID NO: 32) that comprises (i) P at position 238, (ii) A at position 265, (iii) A at position 297, (iv) G at position 298, (v) T at position 299, (vi) A at position 327, and (vii) P at position 329.

In other embodiments, the heavy chain of an antibody comprises the amino acid sequence of SEQ ID NO: 26 (or 90%, 95%, 98%, or 99% identical to SEQ ID NO: 26) that comprises (i) P, A, G, or S at position 242, (ii) A, G, or S at position 269, (iii) A, G, or S at position 301, (iv) G at position 302, (v) T at position 303, (vi) A, G, or S at position 331, and (vii) P, A, G, or S at position 333. In other such embodiments, the heavy chain of an antibody comprises the amino acid sequence of SEQ ID NO: 28 or 30 (or 90%, 95%, 98%, or 99% identical to SEQ ID NO: 28 or 30) that comprises (i) P, A, G, or S at position 240, (ii) A, G, or S at position 267, (iii) A, G, or S at position 299, (iv) G at position 300, (v) T at position 301, (vi) A, G, or S at position 329, and (vii) P, A, G, or S at position 331. In yet other embodiments, the heavy chain of an antibody comprises the amino acid sequence of SEQ ID NO: 32 (or 90%, 95%, 98%, or 99% identical to SEQ ID NO: 32) that comprises (i) P, A, G, or S at position 238, (ii) A, G, or S at position 265, (iii) A, G, or S at position 297, (iv) G at position 298, (v) T at position 299, (vi) A, G, or S at position 327, and (vii) P, A, G, or S at position 329.

In still other embodiments, the heavy chain of an antibody comprises the amino acid sequence of SEQ ID NO: 26 (or 90%, 95%, 98%, or 99% identical to SEQ ID NO: 26) that comprises (i) P, A, G, or S at position 242, (ii) A at position 269, (iii) A at position 301, (iv) G at position 302, (v) T at position 303, (vi) A, G, or S at position 331, and (vii) P, A, G, or S at position 333. In yet other embodiments, the heavy chain of an antibody comprises the amino acid sequence of SEQ ID NO: 28 or 30 (or 90%, 95%, 98%, or 99% identical to SEQ ID NO: 28 or 30) that comprises (i) P, A, G, or S at position 240, (ii) A at position 267, (iii) A at position 299, (iv) G at position 300, (v) T at position 301, (vi) A, G, or S at position 329, and (vii) P, A, G, or S at position 331. In other such embodiments, the heavy chain of an antibody comprises the amino acid sequence of SEQ ID NO: 32 (or 90%, 95%, 98%, or 99% identical to SEQ ID NO: 32) that comprises (i) P, A, G, or S at position 238, (ii) A at position 265, (iii) A at position 297, (iv) G at position 298, (v) T at position 299, (vi) A, G, or S at position 327, and (vii) P, A, G, or S at position 329.

In still other embodiments, the heavy chain of an antibody comprises the amino acid sequence of SEQ ID NO: 26 (or 90%, 95%, 98%, or 99% identical to SEQ ID NO: 26) that comprises (i) A at position 242, (ii) A at position 269, (iii) A at position 301, (iv) G at position 302, (v) T at position 303, (vi) G at position 331, and (vii) A at position 333. In yet other embodiments, the heavy chain of an antibody comprises the amino acid sequence of SEQ ID NO: 28 or 30 (or 90%, 95%, 98%, or 99% identical to SEQ ID NO: 28 or 30) that comprises (i) A at position 240, (ii) A at position 267, (iii) A at position 299, (iv) G at position 300, (v) T at position 301, (vi) G at position 329, and (vii) A at position 331. In other such embodiments, the heavy chain of an antibody comprises the amino acid sequence of SEQ ID NO: 32 (or 90%, 95%, 98%, or 99% identical to SEQ ID NO: 32) that comprises (i) A at position 238, (ii) A at position 265, (iii) A at position 297, (iv) G at position 298, (v) T at position 299, (vi) G at position 327, and (vii) A at position 329. In addition, the present invention provides caninized antibody or antigen binding fragment thereof that further comprise a canine light chain that comprises the amino acid sequence of SEQ ID NO: 38 or SEQ ID NO: 44.

Accordingly, the present invention further provides a caninized antibody or antigen binding fragment thereof that comprises a heavy chain comprising the amino acid sequence of SEQ ID NO: 34 and a light chain comprising the amino acid sequence of SEQ ID NO: 38. In a related embodiment, the caninized antibody or antigen binding fragment thereof comprises a heavy chain comprising the amino acid sequence of SEQ ID NO: 36 and a light chain comprising the amino acid sequence of SEQ ID NO: 38. In another embodiment, the caninized antibody or antigen binding fragment thereof comprises a heavy chain comprising the amino acid sequence of SEQ ID NO: 40 and a light chain comprising the amino acid sequence of SEQ ID NO: 44. In a related embodiment, the caninized antibody or antigen binding fragment thereof comprises a heavy chain comprising the amino acid sequence of SEQ ID NO: 42 and a light chain comprising the amino acid sequence of SEQ ID NO: 44.

In yet another embodiment, the caninized antibody or antigen binding fragment thereof comprises a heavy chain comprising the amino acid sequence of SEQ ID NO: 34 and a light chain comprising the amino acid sequence of SEQ ID NO: 44. In a related embodiment, the caninized antibody or antigen binding fragment thereof comprises a heavy chain comprising the amino acid sequence of SEQ ID NO: 36 and a light chain comprising the amino acid sequence of SEQ ID NO: 44. In still another embodiment, the caninized antibody or antigen binding fragment thereof comprises a heavy chain comprising the amino acid sequence of SEQ ID NO: 40 and a light chain comprising the amino acid sequence of SEQ ID NO: 38. In a related embodiment, the caninized antibody or antigen binding fragment thereof comprises a heavy chain comprising the amino acid sequence of SEQ ID NO: 42 and a light chain comprising the amino acid sequence of SEQ ID NO: 38.

The present invention further provides a caninized antibody or antigen binding fragment thereof that comprises a heavy chain comprising the amino acid sequence of SEQ ID NO: 26 and a light chain comprising the amino acid sequence of SEQ ID NO: 38. In a related embodiment, the caninized antibody or antigen binding fragment thereof comprises a heavy chain comprising the amino acid sequence of SEQ ID NO: 28 and a light chain comprising the amino acid sequence of SEQ ID NO: 38. In another embodiment, the caninized antibody or antigen binding fragment thereof comprises a heavy chain comprising the amino acid sequence of SEQ ID NO: 30 and a light chain comprising the amino acid sequence of SEQ ID NO: 44. In a related embodiment, the caninized antibody or antigen binding fragment thereof comprises a heavy chain comprising the amino acid sequence of SEQ ID NO: 32 and a light chain comprising the amino acid sequence of SEQ ID NO: 44.

The present invention further provides a caninized antibody or antigen binding fragment thereof that comprises a heavy chain comprising the amino acid sequence of SEQ ID NO: 26 and a light chain comprising the amino acid sequence of SEQ ID NO: 44. In a related embodiment, the caninized antibody or antigen binding fragment thereof comprises a heavy chain comprising the amino acid sequence of SEQ ID NO: 28 and a light chain comprising the amino acid sequence of SEQ ID NO: 44. In another embodiment, the caninized antibody or antigen binding fragment thereof comprises a heavy chain comprising the amino acid sequence of SEQ ID NO: 30 and a light chain comprising the amino acid sequence of SEQ ID NO: 38. In a related embodiment, the caninized antibody or antigen binding fragment thereof comprises a heavy chain comprising the amino acid sequence of SEQ ID NO: 32 and a light chain comprising the amino acid sequence of SEQ ID NO: 38.

The present invention further provides nucleic acids that encode any of the amino acid sequences of the present invention including the CDRs, cFc regions, the cFc regions with the hinge regions, and the heavy chains, and the light chains of the caninized antibodies of the present invention. The present invention further provides expression vectors that comprise one or more of the nucleic acids of the present invention. The present invention further provides host cells that comprise one or more expression vectors of the present invention and methods for expressing the CDRs, and/or cFc regions, and/or the cFc regions with the hinge regions, and/or the heavy chains, and/or the light chains of the caninized antibodies of the present invention using such host cells. The present invention also provides host cells that have been genetically engineered to express the CDRs, and/or cFc regions, and/or the cFc regions with the hinge regions, and/or the heavy chains, and/or the light chains of the caninized antibodies of the present invention in the absence of such vectors. In particular embodiments, these nucleic acids, expression vectors, polypeptides, or host cells of the invention are useful in methods of making an antibody.

In particular embodiments, the antibody is a recombinant antibody or a recombinant antigen binding fragment thereof. In related embodiments, the variable heavy chain domain and variable light chain domain are connected by a flexible linker to form a single-chain antibody.

In certain embodiments the present invention provides an antibody or antigen binding fragment thereof (e.g., an isolated antibody or isolated antigen binding fragment thereof) that binds canine PD-L1 with specificity, and which when it is bound to canine PD-L1, the antibody or antigen binding fragment thereof binds to at least one amino acid residue within the amino acid sequence of SEQ ID NO: 82. In related embodiments, the antibody or antigen binding fragment thereof that binds canine PD-L1 with specificity, also binds to at least one amino acid residue within the amino acid sequence of SEQ ID NO: 83. In still other embodiments, the antibody or antigen binding fragment thereof that binds canine PD-L1 with specificity, also binds to at least one amino acid residue within the amino acid sequence of SEQ ID NO: 82 and to at least one amino acid residue within the amino acid sequence of SEQ ID NO: 83. In particular embodiments, these antibodies and/or antigen binding fragments thereof block the binding of canine PD-L1 to canine PD-1. In related embodiments, the antibody is a monoclonal antibody. In particular embodiments of this type the antibody is a monoclonal murine anti-canine PD-L1 antibody. In more particular embodiments, the monoclonal antibody is a caninized antibody. In still more particular embodiments, the monoclonal antibody is a caninized murine anti-canine PD-L1 antibody.

In certain embodiments, the antibody or antigen binding fragment thereof binds to 2 to 5 amino acid residues of SEQ ID NO: 82. In other embodiments, the antibody or antigen binding fragment thereof binds to 6 to 12 amino acid residues of SEQ ID NO: 82. In yet other embodiments, the isolated antibody or antigen binding fragment thereof binds to 13 to 20 amino acid residues of SEQ ID NO: 82. In related embodiments, the antibody or antigen binding fragment thereof binds to 2 to 5 amino acid residues of SEQ ID NO: 83. In other embodiments, the antibody or antigen binding fragment thereof binds to 6 to 11 amino acid residues of SEQ ID NO: 83.

In still other embodiments monoclonal antibodies or antigen binding fragments thereof are provided that cross-compete for binding with canine PD-L1 with one or more of the anti-canine PD-L1 antibodies of the present invention. In particular embodiments, the cross-competing antibodies and antigen binding fragments thereof bind canine PD-L1 and block the binding of canine PD-L1 to canine PD-1. In a more particular embodiments the monoclonal antibodies or antigen binding fragments thereof cross-compete with 4F9 (or an antibody with the 6 CDRs of 4F9) for binding canine PD-L1. In other more particular embodiments the monoclonal antibodies or antigen binding fragments thereof cross-compete with 5F12 (or an antibody with the 6 CDRs of 5F12) for binding canine PD-L1. In yet other embodiments the monoclonal antibodies or antigen binding fragments thereof cross-compete with both 4F9 and with 5F12 for binding canine PD-L1.

In particular embodiments a monoclonal antibody of the present invention is a murine antibody. In other embodiments the monoclonal antibody is a caninized antibody. In more particular embodiments a monoclonal antibody of the present invention is a caninized murine antibody.

Furthermore, the present invention provides antibodies (e.g., caninized antibodies) to canine PD-L1 that comprise the CDRs of the present invention or variants of the CDRs, which have the corresponding canonical structures provided herein, and/or that bind to the amino acid sequence of SEQ ID NO: 82 and/or 83 of PD-L1. In particular embodiments of this type, the dissociation constant (Kd) for caninized antibody-canine PD-L1 binding is $1 \times 10^{-5}$ to $1 \times 10^{-12}$M. In more particular embodiments the caninized antibodies to canine PD-L1 comprise variants of the CDRs of the present invention that have the corresponding canonical structures provided herein and bind to the amino acid sequence of SEQ ID NO: 82 and/or 83 of PD-L1. The present invention therefore includes caninized antibodies and antigen binding fragments thereof that bind canine PD-L1 with specificity, and when they are bound to canine PD-L1, the antibody binds to at least one amino acid residue within the amino acid sequence of SEQ ID NO: 82 and/or 83 of PD-L1. In particular embodiments of this type, the antibodies and antigen binding fragments thereof bind canine PD-L1 and block the binding of canine PD-L1 to canine PD-1. Accordingly, in particular embodiments when bound to canine PD-L1, the caninized antibody (including the antibodies with one or more variant CDR, e.g., a variant such as, but not limited to a conservatively modified variant and/or a variant that comprises a defined canonical structure class) binds to at least one amino acid residue within an epitope of PD-L1, e.g., the amino acid sequence of SEQ ID NO: 82 and/or SEQ ID NO: 83.

The present invention further provides caninized antibodies or antigen binding fragments thereof that bind to canine PD-L1 with a dissociation constant (Kd) that is lower than $1 \times 10^{-12}$M (e.g., $1 \times 10^{-13}$ M, or even lower). In other embodiments the caninized antibodies or antigen binding fragments thereof bind to canine PD-L1 with a dissociation constant of $1 \times 10^{-5}$M to $1 \times 10^{-12}$M. In more particular embodiments the caninized antibodies or antigen binding fragments thereof bind to canine PD-L1 with a dissociation constant of $1 \times 10^{-7}$M to $1 \times 10^{-11}$M. In still more particular embodiments the caninized antibodies or antigen binding fragments thereof bind to canine PD-L1 with a dissociation constant of $1 \times 10^{-8}$M to $1 \times 10^{-11}$M. In yet more particular embodiments the caninized antibodies or antigen binding fragments thereof bind to canine PD-L1 with a dissociation constant of $1 \times 10^{-8}$M to $1 \times 10^{-10}$ M.

The present invention also provides caninized antibodies or antigen binding fragments thereof that bind to canine PD-L1 with an on rate ($k_{on}$) that is greater than $1 \times 10^{7}$M$^{-1}$s$^{-1}$. In other embodiments the caninized antibodies or antigen binding fragments thereof bind to canine PD-L1 with an on rate of $1 \times 10^{2}$ M$^{-1}$s$^{-1}$ to $1 \times 10^{7}$M$^{-1}$s$^{-1}$. In more particular embodiments the caninized antibodies or antigen binding fragments thereof bind to canine PD-L1 with an on rate of $1 \times 10^{3}$ M$^{-1}$s$^{-1}$ to $1 \times 10^{6}$M$^{-1}$s$^{-1}$. In still more particular embodiments the caninized antibodies or antigen binding fragments thereof bind to canine PD-L1 with an on rate of $1 \times 10^{3}$ M$^{-1}$s$^{-1}$ to $1 \times 10^{5}$M$^{-1}$s$^{-1}$. In yet more particular embodiments the caninized antibodies or antigen binding fragments thereof bind to canine PD-L1 with an on rate of $1\times10^4$ $M^{-1}s^{-1}$ to $1\times10^5$ $M^{-1}$ $s^{-1}$.

The present invention also provides caninized antibodies or antigen binding fragments thereof that bind to canine PD-L1 with an off rate ($k_{off}$) slower than $1\times10^{-7}s^{-1}$. In particular embodiments the caninized antibodies or antigen binding fragments thereof bind to canine PD-L1 with an off rate of $1\times10^{-3}$ $s^{-1}$ to $1\times10^{-8}$ $s^{-1}$. In more particular embodiments the caninized antibodies or antigen binding fragments thereof bind to canine PD-L1 with an off rate of $1\times10^{-4}$ $s^{-1}$ to $1\times10^{-7}$ $s^{-1}$. In still more particular embodiments the caninized antibodies or antigen binding fragments thereof bind to canine PD-L1 with an off rate of $1\times10^{-5}$ $s^{-1}$ to $1\times10^{-7}$ $s^{-1}$.

In related embodiments, the antibodies (e.g., caninized antibodies) or antigen binding fragments thereof stimulate antigen-specific memory responses to a tumor or pathogen. In particular embodiments, the antibodies (e.g., caninized antibodies) or antigen binding fragments thereof stimulate an antibody response in vivo. In other particular embodiments, the antibodies (e.g., caninized antibodies) or antigen binding fragments thereof stimulate an immune response in an animal subject. In more specific embodiments the animal subject is a canine. In a related embodiment, the animal subject is a feline.

Accordingly, any of the antibodies (e.g., caninized antibodies) of the present invention can exhibit one, two, three, four, five, or all these properties, i.e., the aforesaid dissociation constants with canine PD-L1, the aforesaid on rates for binding with canine PD-L1, the aforesaid off rates for dissociating from the caninized antibody-canine PD-L1 binding complex, stimulating an antigen-specific memory responses to a tumor or pathogen, stimulating an antibody response in vivo, and/or stimulating an immune response in an animal subject.

In more particular embodiments the antibodies and/or antigen binding fragments thereof of the present invention bind canine PD-L1 and also block the binding of canine PD-L1 to PD-1. In even more particular embodiments the caninized antibodies and antigen binding fragments thereof of the present invention bind canine PD-L1 and block the binding of canine PD-L1 to PD-1.

As indicated above, the antibodies (and antigen binding fragments thereof) of the present invention, including certain aforesaid antibodies (and antigen binding fragments thereof), can be monoclonal antibodies (and antigen binding fragments thereof), mammalian antibodies (and antigen binding fragments thereof), e.g., murine (mouse) antibodies (and antigen binding fragments thereof), caninized antibodies (and antigen binding fragments thereof) including caninized murine antibodies (and antigen binding fragments thereof). In certain embodiments the antibodies (and antigen binding fragments thereof) are isolated.

In particular embodiments, the antibody is a recombinant antibody or an antigen binding fragment thereof. In related embodiments, the variable heavy chain domain and variable light chain domain are connected by a flexible linker to form a single-chain antibody.

In particular embodiments, the antibody or antigen binding fragment is a Fab fragment. In other embodiments, the antibody or antigen binding fragment is a Fab' fragment. In other embodiments, the antibody or antigen binding fragment is a (Fab')$_2$ fragment. In still other embodiments, the antibody or antigen binding fragment is a diabody. In particular embodiments, the antibody or antigen binding fragment is a domain antibody. In particular embodiments, the antibody or antigen binding fragment is a camelized single domain antibody.

In particular embodiments, a caninized murine anti-canine PD-L1 antibody or antigen binding fragment increases the immune response of the animal subject (e.g., canine or feline) being treated.

The present invention further provides nucleic acids (including isolated nucleic acids) that encode any one of the antibodies and portions thereof (including CDRs) of the present invention. In certain embodiments, the present invention provides nucleic acids (including isolated nucleic acids) that encode any one of the light chains of the caninized antibodies or portions thereof of the present invention. Similarly, the present invention provides nucleic acids (including isolated nucleic acids) that encode any one of the heavy chains of the caninized antibody or portions thereof of the present invention. The present invention further provides expression vectors that comprise one or more of the nucleic acids (including isolated nucleic acids) of the present invention. Accordingly, the present invention provides nucleic acids that encode the caninized murine anti-canine PD-L1 antibodies or portions thereof of the present invention. In related embodiments such antibodies or antigen binding fragments can be used for the preparation of a medicament to treat cancer in a canine and/or feline subject. Alternatively, or in conjunction, the present invention provides for the use of any of the antibodies or antibody fragments of the present invention for diagnostic use. In yet additional embodiments, a kit is provided comprising any of the caninized antibodies or antigen binding fragments disclosed herein.

In specific embodiments an expression vector is provided comprising an isolated nucleic acid encoding any of the caninized murine anti-canine PD-L1 antibodies or antigen binding fragments of the invention. The present invention further provides host cells that comprise one or more expression vectors of the present invention. In particular embodiments, these nucleic acids, expression vectors or polypeptides of the invention are useful in methods of making an antibody.

The present invention further provides antigenic peptides (including isolated antigenic peptides) that consist of 80 or fewer amino acid residues that comprise the amino acid sequence of SEQ ID NO: 82 and/or SEQ ID NO: 83. In related embodiments, the antigenic peptides (including isolated peptides) consist of 60 or fewer amino acid residues that comprise the amino acid sequence of SEQ ID NO: 82 and/or SEQ ID NO: 83. In related embodiments, the antigenic peptides (including isolated peptides) consist of 11 to 45 amino acid residues that comprise the amino acid sequence of SEQ ID NO: 82 and/or SEQ ID NO: 83. In yet other embodiments the antigenic peptides consist of 5 to 20 amino acid residues from the amino acid sequence of SEQ ID NO: 83. In still other embodiments the antigenic peptides consist of 5 to 11 amino acid residues from the amino acid sequence of SEQ ID NO: 83.

The present invention further provides antigenic peptides (including isolated peptides) that consist of 80 or fewer amino acid residues that comprise an amino acid sequence that is 80%, 85%, 90%, 95% or 100% identical with the amino acid sequence of SEQ ID NO: 82 and/or SEQ ID NO: 83 and binds to an isolated mammalian antibody or antigen binding fragment thereof of the present invention. In related embodiments, the antigenic peptides (including isolated antigenic peptides) consist of 60 or fewer amino acid residues that comprise an amino acid sequence that is 80%, 85%, 90%, 95% or 100% identical with the amino acid sequence of SEQ ID NO: 82 and/or SEQ ID NO: 83 and binds to an isolated mammalian antibody or antigen binding fragment thereof. In other embodiments the peptides consist of 5 to 20 amino acid residues from an amino acid sequence that is 80%, 85%, 90%, 95% or 100% identical with the amino acid sequence of SEQ ID NO: 82 and binds to an isolated mammalian antibody or antigen binding fragment thereof. In other embodiments the peptides consist of 5 to 11 amino acid residues from an amino acid sequence that is 80%, 85%, 90%, 95% or 100% identical with the amino acid sequence of SEQ ID NO: 83 and binds to an isolated mammalian antibody or antigen binding fragment thereof. In particular embodiments the mammalian antibody is 4E9. In other embodiments the mammalian antibody is 5F12.

The present invention further provides fusion proteins that comprise any of the aforesaid antigenic peptides. In a particular embodiment, the fusion protein comprises such an antigenic peptide and an Fc region of a non-canine mammalian IgG antibody. In a more particular embodiment the fusion protein comprises an Fc region of a non-canine mammalian IgG antibody. In certain embodiments the non-canine mammalian IgG antibody is a murine IgG. In alternative embodiments the non-canine mammalian IgG antibody is a human IgG. In other embodiments the non-canine mammalian IgG antibody is an equine IgG. In still other embodiments the non-canine mammalian IgG antibody is a porcine IgG. In yet other embodiments the non-canine mammalian IgG antibody is a bovine IgG.

In particular embodiments the non-canine mammalian IgG antibody is an IgG1. In other embodiments the non-canine mammalian IgG antibody is an IgG2a. In still other embodiments the non-canine mammalian IgG antibody is an IgG3. In yet other embodiments the non-canine mammalian IgG antibody is an IgG4.

In other embodiments the fusion protein comprises any of the aforesaid antigenic peptides and maltose-binding protein. In yet other embodiments, the fusion protein comprises any of the aforesaid antigenic peptides and beta-galactosidase. In still other embodiments the fusion protein comprises any of the aforesaid antigenic peptides and glutathione S-transferase. In yet other embodiments, the fusion protein comprises any of the aforesaid antigenic peptides and thioredoxin. In still other embodiments the fusion protein comprises any of the aforesaid antigenic peptides and Gro EL. In yet other embodiments the fusion protein comprises any of the aforesaid antigenic peptides and NusA.

The present invention further provides nucleic acids (including isolated nucleic acids) that encode the antigenic peptides and the corresponding fusion proteins of the present invention. The present invention also provides expression vectors that comprise these nucleic acids and host cells that comprise one or more expression vectors of the present invention.

In addition, the present invention includes pharmaceutical compositions comprising anti-canine PD-L1 antibodies or antigen binding fragments thereof of the present invention, antigenic peptides (including isolated antigenic peptides) from canine PD-L1, fusion proteins comprising the antigenic peptides from canine PD-L1 of the present invention, nucleic acids (including isolated nucleic acids) encoding the antigenic fragments and/or fusion proteins of the present invention, the expression vectors comprising such nucleic acids, or any combination thereof, and a pharmaceutically acceptable carrier or diluent.

In particular embodiments such pharmaceutical compositions further comprise an anti-canine PD-1 antibody or antigen binding fragment thereof. In more particular embodiments the anti-canine PD-1 antibody is a caninized murine anti-canine PD-1 antibody or a antigen binding fragment of the caninized murine anti-canine PD-1 antibody. In related embodiments, such pharmaceutical compositions further comprise an anti-canine CTLA-4 antibody or an antigen binding fragment thereof. In particular embodiments the anti-canine CTLA-4 antibody is a caninized murine anti-canine CTLA-4 antibody or an antigen binding fragment of a caninized murine anti-canine CTLA-4 antibody.

Accordingly, the present invention provides pharmaceutical compositions that comprise one, two, three, or more of the following: an anti-canine PD-L1 antibody, an anti-canine PD-1 antibody, an anti-canine CTLA-4 antibody, an antigen binding fragment of an anti-canine PD-L1 antibody, an antigen binding fragment of an anti-canine PD-1 antibody, or an antigen binding fragment of an anti-canine CTLA-4 antibody. In particular embodiments, such anti-canine protein (i.e., anti-canine PD-L1, PD-1, or CTLA-4) antibodies or the antigen binding fragments thereof are murine anti-canine protein antibodies. In other such anti-canine protein antibodies or the antigen binding fragments thereof are caninized anti-canine protein antibodies. In more particular embodiments the anti-canine protein antibodies or the antigen binding fragments thereof are caninized murine anti-canine protein antibodies.

In addition, the present invention provides methods of increasing the activity of an immune cell, comprising administering to a subject in need thereof a therapeutically effective amount of a pharmaceutical composition of the present invention. In certain embodiments the method is used for the treatment of cancer. In other embodiments, the method is used in the treatment of an infection or infectious disease. In still other embodiments, a caninized antibody of the present invention or antigen binding fragment thereof is used as a vaccine adjuvant. In particular embodiments a pharmaceutical composition comprising a caninized murine anti-canine PD-L1 antibody or antigen binding fragment thereof can be administered before, after or concurrently with a caninized murine anti-canine PD-1 antibody or antigen binding fragment thereof and/or a caninized murine anti-canine CTLA-4 antibody or antigen binding fragment thereof.

These and other aspects of the present invention will be better appreciated by reference to the following Brief Description of the Drawings and the Detailed Description.

BRIEF DESCRIPTION OF THE DRAWINGS

FIG. 1 shows the ELISA results for reactivity of two mouse anti-canine PD-L1 mAbs against canine PD-L1, as a function of OD 650/490 versus the log mAb (nM). Both mAbs, designated 4F9 and 5F12, demonstrate strong and dose-dependent binding to canine PD-L1.

FIG. 2 shows ligand blockade with mouse anti-canine PD-L1 mAbs. Two mAbs designated 4F9 and 5F12 were tested for their ability to inhibit binding of PD-L1 to PD-1 expressed on CHO cells. Both mAbs blocked the binding of PD-L1 to PD-1, although mAb 4F9 is a stronger inhibitor than 5F12.

DETAILED DESCRIPTION

Abbreviations

Throughout the detailed description and examples of the invention the following abbreviations will be used:

ADCC Antibody-dependent cellular cytotoxicity
CDC Complement-dependent cyotoxicity
CDR Complementarity determining region in the immunoglobulin variable regions, defined for human antibodies using the Kabat numbering system
CHO Chinese hamster ovary
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system for human antibodies pioneered by Elvin A. Kabat [*Sequences of Proteins of Immunological Interest*, 5th Ed. Public Health Service, National Institutes of Health, Bethesda, Md. (1991)]
mAb Monoclonal antibody (also Mab or MAb)
MES 2-(N-morpholino)ethanesulfonic acid
MOA Mechanism of action
NHS Normal human serum
PCR Polymerase chain reaction
PK Pharmacokinetics
SEB *Staphylococcus* Enterotoxin B
TT Tetanus toxoid
V region The segment of human IgG chains which is variable in sequence between different antibodies. It extends to Kabat residue 109 in the light chain and 113 in the heavy chain.
VH Immunoglobulin heavy chain variable region
VK Immunoglobulin kappa light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, e.g., a canine experimental subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell. "Treat" or "treating" means to administer a therapeutic agent, such as a composition containing an antibody or antigen binding fragment of the present invention, internally or externally to a veterinary subject (e.g., canine or feline) having one or more disease symptom, or being suspected of having a disease, for which the agent has therapeutic activity. Accordingly, "administration" and "treatment" also includes in vitro and ex vivo treatments, e.g., of a cell, by a reagent, diagnostic, binding compound, or by another cell.

Typically, the agent is administered in an amount effective to alleviate and/or ameliorate one or more disease symptom in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the subject (e.g., canine), and the ability of the pharmaceutical composition to elicit a desired response in the subject. Whether a disease symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the mammalian body (e.g., canine body) of cancerous cells, cells or tissues infected with pathogens, or invading pathogens.

The term "subject" includes any organism, preferably an animal, more preferably a mammal (e.g., canine, feline, or human) and most preferably a canine.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats, and wild or feral cats.

Canine PD-1 has been found to comprise the amino acid sequence of SEQ ID NO: 50 [U.S. provisional application No. 61/918,946, filed on Dec. 20, 2013, the contents of which are hereby incorporated herein in their entireties]. In a specific embodiment canine PD-1 is encoded by a nucleic acid that comprises the nucleotide sequence of SEQ ID NO: 49.

Canine PD-L1 has been found to comprise the amino acid sequence of SEQ ID NO: 56 [U.S. provisional application No. 61/918,946, filed on Dec. 20, 2013, supra]. In a specific embodiment canine PD-L1 is encoded by a nucleotide sequence comprising SEQ ID NO: 55.

As used herein, a "substitution of an amino acid residue" with another amino acid residue in an amino acid sequence of, for example an antibody, is equivalent to "replacing an amino acid residue" with another amino acid residue and denotes that a particular amino acid residue at a specific position in the amino acid sequence has been replaced by (or substituted for) by a different amino acid residue. For example, one such substitution (replacement) is denoted as P4A of an Fc region of an IgGB or IgGC amino acid sequence, in which case, the proline residue at amino acid position 4 of the amino acid sequence of the Fc region of an IgGB or the Fc region of an IgGC has been substituted for (replaced) by an alanine residue.

Accordingly, such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies.

Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

Sequence similarity includes identical residues and non-identical, biochemically related amino acids. Biochemically related amino acids that share similar properties and may be interchangeable are discussed below.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); *Natl. Biomed. Res.* Found., Washington, D.C.; Schwartz, R. M., et al., "Matrices for detecting distant relationships." in *Atlas of Protein Sequence and Structure*, vol. 5, suppl. 3." (1978), M. O. Dayhoff (ed.), pp. 353-358 (1978), *Natl. Biomed. Res. Found.*, Washington, DC; Altschul, S. F., *J. Mol. Biol.* 219:555-565 (1991); States, D. J., et al., *Methods* 3:66-70(1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, N.Y. (1997).

Caninized Anti-Canine Antigen Antibodies

As used herein, an antibody is said to bind specifically to a polypeptide comprising a given antigen sequence (in this case a portion of the amino acid sequence of a canine antigen, e.g., canine PD-L1) if it binds to polypeptides comprising that portion of the amino acid sequence of the canine antigen, e.g., canine PD-L1, but does not bind to other canine proteins lacking that portion of the sequence of the canine antigen, e.g., canine PD-L1. For example, an antibody that specifically binds to a polypeptide comprising canine PD-L1 may bind to a FLAG®-tagged form of canine PD-L1, but will not bind to other FLAG®-tagged canine proteins with specificity. An antibody, or binding compound derived from the antigen-binding site of an antibody, binds to its canine antigen, or a variant or mutein thereof, "with specificity" when it has an affinity for that canine antigen or a variant or mutein thereof which is at least ten-times greater, more preferably at least 20-times greater, and even more preferably at least 100-times greater than its affinity for any other canine antigen tested.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), caninized antibodies, fully canine antibodies, chimeric antibodies, and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antigen binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

A "fragment crystallizable" ("Fc") region contains two heavy chain fragments (i.e., two identical polypeptides) comprising the $C_H2$ and $C_H3$ domains of an antibody. The two heavy chain fragments are held together by two or more disulfide bonds and by hydrophobic interactions of the $C_H3$ domains. In the present invention, the amino acid sequence for each of the four canine IgG Fc fragments is based on the identified boundary of CH1 and CH2 domains as determined by Tang et al. [*Vet. Immunol. Immunopathol.* 80: 259-270 (2001)].

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. [See, Pluckthun, THE PHARMACOLOGY OF MONOCLONAL ANTIBODIES, vol. 113 Rosenburg and Moore eds., Springer-Verlag, New York, pp. 269-315 (1994); WO 88/01649; and U.S. Pat. Nos. 4,946,778 and 5,260,203.]

As used herein, the term "canonical structure" refers to the local conformation that can be adopted by each of the hypervariable regions of the heavy and light chain of an antibody within the framework that they reside. For each hypervariable region, there are a small number of canonical structures (generally denoted by simple integers such as 1 or 2 etc.), which can be predicted with great accuracy from the amino acid sequences of the corresponding hypervariable region (particularly within the context of the amino acid sequence of its framework, as provided below for the corresponding caninized murine anti-canine PD-L1 variable domains). These canonical structures can be determinative regarding whether a modification of the amino acid sequence of a given CDR will result in the retention or loss of the ability to bind to its antigen binding partner [See, Chothia and Lesk, *Canonical Structures for the hypervariable regions of immunoglobulins, J. Mol. Biol.* 196:901-917 (1987); Chothia et al., *Conformation of immunoglobulin hypervaribale regions, Nature,* 34:877-883(1989); and Al-Lazikani et al., *Standard Conformations for the canonical structures of immunoglobulins, J. Mol. Biol.* 273:927-948 (1997)].

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. [See, e.g., Muyldermans et al., *Trends Biochem. Sci.* 26:230 (2001); Reichmann et al., *J. Immunol. Methods* 231:25 (1999); WO 94/04678; WO 94/25591; U.S. Pat. No. 6,005,079]. In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. [See, EP 0 404 097 B1; WO 93/11161; and Holliger et al., *Proc. Natl. Acad. Sci. USA* 90: 6444-6448 (1993)]. For a review of engineered antibody variants generally see [Holliger and Hudson *Nat. Biotechnol.* 23:1126-1136 (2005)].

Typically, an antibody or antigen binding fragment of the invention retains at least 10% of its canine PD-L1 binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine antigen, (e.g., PD-L1) binding affinity as the parental antibody. It is also intended that a caninized antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, a "chimeric antibody" is an antibody having the variable domain from a first antibody and the constant domain from a second antibody, where the first and second antibodies are from different species. [U.S. Pat. No. 4,816,567; and Morrison et al., *Proc. Natl. Acad. Sci. USA* 81: 6851-6855 (1984)]. Typically the variable domains are obtained from an antibody from an experimental animal (the "parental antibody"), such as a rodent, and the constant domain sequences are obtained from the animal subject antibodies, e.g., canine, so that the resulting chimeric antibody will be less likely to elicit an adverse immune response in a canine subject, than the parental (e.g., rodent) antibody.

As used herein, the term "caninized antibody" refers to forms of antibodies that contain sequences from both canine and non-canine (e.g., murine) antibodies. In general, the caninized antibody will comprise substantially all of at least one, and typically two, variable domains, in which all or substantially all of the hypervariable loops correspond to those of a non-canine immunoglobulin (e.g., comprising 6 murine anti-canine PD-L1 CDRs as exemplified below), and all or substantially all of the canine frame.

The term "fully canine antibody" refers to an antibody that comprises canine immunoglobulin protein sequences only. A fully canine antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully canine antibody may contain rat carbohydrate chains if produced in a rat, in a rat cell, or in a hybridoma derived from a rat cell. Similarly, "rat antibody" refers to an antibody that comprises rat immunoglobulin sequences only.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually flanked by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain for human antibodies is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). [See Kabat et al. *Sequences of Proteins of Immunological Interest,* 5th Ed. Public Health Service, National Institutes of Health, Bethesda, Md. (1991), definining the CDR regions of a human antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

As used herein the term "canine frame" refers to the amino acid sequence of the heavy chain and light chain of a canine antibody other than the hypervariable region residues defined herein as CDR residues. In both chains, the amino acid sequences of the native canine CDRs are replaced with the corresponding foreign CDRs (e.g., those from a mouse antibody). Optionally the heavy and/or light chains of the canine antibody may contain some foreign non-CDR residues, e.g., so as to preserve the conformation of the foreign CDRs within the canine antibody, and/or to modify the Fc function, as exemplified below.

As used herein, an "anti-canine PD-L1 antibody" refers to an antibody that was raised against canine PD-L1 (e.g., in a mammal such as a mouse or rabbit) and that specifically binds to canine PD-L1. An antibody that "specifically binds to canine PD-L1," or an antibody that "specifically binds to a polypeptide comprising the amino acid sequence of SEQ ID NO: 56", is an antibody that exhibits preferential binding to canine PD-L1 as compared to other antigens, e.g., binds canine PD-L1 "with specificity". The binding does not require absolute binding specificity. An anti-canine PD-L1 antibody is considered "specific" for canine PD-L1 if its binding is determinative of the presence of canine PD-L1 in a sample, or if it is capable of altering the activity of canine PD-L1 without unduly interfering with the activity of other molecules in a canine sample, e.g., without producing undesired results such as false positives in a diagnostic context or side effects in a therapeutic context. The degree of specificity necessary for an anti-canine PD-L1 antibody may depend on the intended use of the antibody, and at any rate is defined by its suitability for use for an intended purpose. The antibody, or binding compound derived from the antigen-binding site of an antibody, of the contemplated method binds to its antigen, or a variant or mutein thereof, with an affinity that is at least two-fold greater, preferably at least ten-times greater, more preferably at least 20-times greater, and most preferably at least 100-times greater than the affinity with any other antigen.

Accordingly the present invention provides caninized anti-canine PD-L1 antibodies or antigen binding fragments thereof (including in isolated form) that bind canine PD-L1 (e.g., with specificity) and uses of such antibodies or fragments thereof. In specific embodiments murine anti-canine PD-L1 CDRs from murine anti-canine PD-L1 antibodies are provided that have been shown to both bind canine PD-L1 and to block the binding of canine PD-L1 to its receptor, e.g., canine PD-1. These CDRs can be inserted into a modified canine frame of the present invention to make a caninized murine anti-canine PD-L1 antibody, as exemplified herein.

More specifically, a "caninized murine anti-PD-L1 antibody" of the present invention refers to an antibody that comprises the three heavy chain CDRs and the three light chain CDRs from a murine anti-canine PD-L1 antibody together with a canine frame or a modified canine frame. A modified canine frame comprises one or more amino acids changes as exemplified herein that further optimize the effectiveness of the caninized antibody, e.g., to augment, reduce, or eliminate antibody effector functions, to increase its binding to the canine antigen, e.g., canine PD-L1, and/or increase its ability to block the binding of the canine antigen, e.g., canine PD-L1, to its natural binding partner, (e.g., canine PD-1 in the case where the antigen is canine PD-L1).

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. [*Nucleic Acids Res.* 33:D256-D261 (2005)].

Properties of Caninized Antibodies

In canine, there are four IgG heavy chains referred to as A, B, C, and D. These heavy chains represent four different subclasses of dog IgG, which are referred to as IgGA, IgGB, IgGC and IgGD. The DNA and amino acid sequences of these four heavy chains were first identified by Tang et al. [*Vet. Immunol. Immunopathol.* 80: 259-270 (2001)]. The amino acid and DNA sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example the kappa light chain amino acid sequence has accession number ABY 57289.1 and the lambda light chain has accession number ABY 55569.1. In the present invention, the amino acid sequence for each of the four canine IgG Fc fragments is based on the identified boundary of CH1 and CH2 domains as determined by Tang et al, supra.

The development of a therapeutic monoclonal antibody is a complex process that entails coordination of a complex set of activities to generate the desired antibody. These include optimization of the antibody specificity, affinity, functional activity, expression level in engineered cell lines, long-term stability, elimination or enhancement of effector functions and development of commercially viable manufacturing and purification methods. Considering the objectives of the present invention and aside from the capacity to activate cells of the immune systems, a caninized or canine monoclonal antibody against canine PD-L1 optimally has three additional attributes:
 1. lack of effector functions such as antibody-dependent cytotoxicity (ADCC) and complement-dependent cytotoxicity (CDC),
 2. relatively long half-life in vivo; and
 3. be readily purified on a large scale using industry standard technologies such as that based on protein A chromatography.

None of the naturally occurring canine IgG subclasses satisfy all these criteria. For example, IgGB can be purified using protein A, but has a high level of ADCC activity. IgGC also has considerable ADCC activity. On the other hand, IgGA binds weakly to protein A, but displays undesirable ADCC activity. Moreover, neither IgGC nor IgGD can be purified on protein A columns, although IgGD display no ADCC activity. Additionally IgGC has short serum half-life as it does not bind to the canine FcRn receptor. The present invention overcomes this difficulty by providing modified canine IgG antibodies specific to canine antigens, e.g., canine PD-L1; such antibodies lack effector functions such as ADCC and CDC, display relatively long half-life, and can be easily of purified using industry standard protein A chromatography.

Heretofore, genetically modified canine IgGs that lacked both ADCC and CDC effector functions and in addition, could be purified by protein A chromatography had not been previously described. As disclosed herein, a single substitution at a position in canine IgG that is analogous to that of human and mouse IgG, such as N297A or D265A, does not completely eliminate both ADCC and CDC effector functions in the corresponding canine antibody. For example, while each of the substitutions N297 and D265 in human or murine antibodies results in abrogation of binding to $Fc_\gamma$ receptor and C1q, neither substitution alone completely abrogated the binding of canine antibodies to C1q. Instead, as further disclosed below, in order to eliminate both ADCC and CDC in canine antibodies of IgGB or IgGC sub-classes, it proved necessary to make a double substitution in the Fc of the canine antibody combining both an asparagine-to-alanine and an aspartic acid-to-alanine substitution. Moreover, completely unexpectedly, one substitution that had been shown to reduce effector functions in human antibodies actually resulted in an increase in binding of corresponding canine IgG to $Fc_1R$ and C1q.

In order to generate variants of canine IgGB and IgGC that lack effector functions, modified canine IgGB or modified canine IgGC heavy chains can be generated. A total of seven amino acid residues which are present in both of these canine fragment crystallizable regions (cFcs) were identified for such possible substitution. These seven amino acid residues are: P4, D31, N63, G64, T65, A93, and P95 for both the amino acid sequence of SEQ ID NO: 66 for the Fc of canine IgGB; and the amino acid sequence of SEQ ID NO: 68 for the Fc of canine IgGC. Accordingly, the amino acid sequence of SEQ ID NO: 2 differs from that of SEQ ID NO: 66 by having the amino acid residues at positions: 4, 31, 63, 64, 65, 93, and 95, which are proline (P), aspartic acid (D), asparagine (N), glycine (G), threonine (T), alanine (A), and proline (P), respectively, in the amino acid sequence of SEQ ID NO: 66 as "X" (or "Xaa" in the three letter code) for all seven positions, signifying that these seven amino acid positions can be any of the twenty natural amino acids (see list in column 1 of Table 1 below). Similarly, the amino acid sequence of SEQ ID NO: 4 differs from that of SEQ ID NO: 68 by having the amino acid residues at positions 4, 31, 63, 64, 65, 93, and 95 are listed as "X" (or "Xaa" in the three letter code) for all seven positions, signifying that these seven amino acid positions can be any of the twenty natural amino acids. The amino acid sequence of SEQ ID NO: 2 is encoded by the nucleotide sequence of SEQ ID NO: 1, whereas the amino acid sequence of SEQ ID NO: 4 is encoded by the nucleotide sequence of SEQ ID NO: 3.

In one embodiment, the cFc comprises the amino acid sequence of SEQ ID NO: 66 with the following substitutions P4(A, G, or S) D31(A, G, or S) N63(A, G, or S), G64(A or P), T65(A, G, or S), A93(G or S), and P95(A, G, or S); in which P4 (A G, or S) signifies that the proline residue at position 4 is replaced by either an alanine, glycine, or serine residue, and similarly G64(P or A) signifies that the glycine residue at position 64 is replaced by either a proline or an alanine residue, etc.). In a particular embodiment, the cFc comprises the amino acid sequence of SEQ ID NO: 66 with the following substitutions: P4A, D31A, N63A, G64P, T65A, A93G, and P95A, In a related embodiment, the cFc comprises the amino acid sequence of SEQ ID NO: 4, which contains 7 amino acids designated as Xaa, with the following amino acid residues: A4, A31, A63, G64, T65, G93, and A95, i.e., the amino acid sequence of SEQ ID NO: 68 with the following five (5) amino acid residue changes: P4A, D31A, N63A, A93G, and P95A and the remaining two amino acid residues of the seven, G64 and T65, being retained from the amino acid sequence of SEQ ID NO: 68.

The amino acid sequences of SEQ ID NO: 26, SEQ ID NO: 28, SEQ ID NO: 30, and SEQ ID NO: 32 all contain "X" (or "Xaa" in the three letter code) at seven amino acid positions, signifying that these seven amino acid positions can be any of the twenty natural amino acids listed in column 1 of Table 1 below. Notably SEQ ID NO: 26, SEQ ID NO: 28, SEQ ID NO: 30, and SEQ ID NO: 32 comprise either the amino acid sequence of SEQ ID NO: 2 or that of SEQ ID NO: 4 within their respective sequences. Specific examples of the amino acid residues at one or more of these seven positions of the amino acid sequences are delineated above and below, and are therefore included within the genus of the individual amino acid sequences of SEQ ID NO: 2, SEQ ID NO: 4, SEQ ID NO: 26, SEQ ID NO: 28, SEQ ID NO: 30, and SEQ ID NO: 32, as well as within the caninized antibodies that comprise these sequences.

Table 10 provided below, specifically correlates the seven amino acid positions that can be replaced, as disclosed herein, of the cIgGB Fc (SEQ ID NO: 66 and SEQ ID NO: 2) and the cIgGC Fc (SEQ ID NO: 68 and SEQ ID NO: 4) with that of the full length canine heavy chains that comprises these cFc amino acid sequences, i.e., SEQ ID NO: 26, SEQ ID NO: 28, SEQ ID NO: 30, and SEQ ID NO: 32. Accordingly, the actual position in the full length sequence IgGB or IgGC can be readily coordinated with that of the cFc that it comprises through the use of Table 10 below.

In particular embodiments, the heavy chain of an antibody comprises the amino acid sequence of SEQ ID NO: 26 comprising (i) P, A, G, or S at position 242, (ii) D, A, G, or S at position 269, (iii) N, A, G, or S at position 301, (iv) G, P, or A at position 302, (v) T, A, G, or S at position 303, (vi) A, G, or S at position 331, and (vii) P, A, G, or S at position 333. In other embodiments, the heavy chain of an antibody comprises the amino acid sequence of SEQ ID NO: 28 or 30 comprising (i) P, A, G, or S at position 240, (ii) D, A, G, or S at position 267, (iii) N, A, G, or S at position 299, (iv) G, P, or A at position 300, (v) T, A, G, or S at position 301, (vi) A, G, or S at position 329, and (vii) P, A, G, or S at position 331. In other embodiments, the heavy chain of an antibody comprises the amino acid sequence of SEQ ID NO: 31 comprising (i) P, A, G, or S at position 238, (ii) D, A, G, or S at position 265, (iii) N, A, G, or S at position 297, (iv) G, P, or A at position 298, (v) T, A, G, or S at position 299, (vi) A, G, or S at position 327, and (vii) P, A, G, or S at position 329.

The present invention also provides modified canine IgGDs which comprise a hinge region from either IgGA, IgGB, or IgGC in place of its natural IgGD hinge region. Alternatively, the IgGD hinge region can be genetically modified by replacing a serine residue with a proline residue as shown in Table 5. Such modifications can lead to a canine IgGD lacking fab arm exchange. The modified canine IgGDs can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgGD can be modified so that it encodes the modified IgGDs. The modified nucleic acid sequences are then cloned into expression plasmids for protein expression. The nucleic acids encoding the canine IgGD Fcs with the substitute hinge region are exemplified by nucleotide sequences of SEQ ID NOs: 7, 9, and 11 which encode the amino acid sequences of SEQ ID NOs: 8, 10, and 12. A nucleic acid encoding a canine IgGD Fc with a modified IgGD hinge region comprises the nucleotide sequence of SEQ ID NO: 5 which encodes the amino acid sequence of SEQ ID NO: 6.

The present invention further provides full length canine heavy chains that can be matched with corresponding light chains to make a caninized antibody. Accordingly, the present invention further provides caninized murine anti-canine antigen antibodies (including isolated caninized murine anti-canine PD-L1 antibodies) and methods of use of the antibodies or antigen binding fragments thereof in the treatment of disease e.g., the treatment of cancer in canines.

Moreover, the present invention provides caninized murine anti-canine PD-L1 antibodies or antigen binding fragments that bind to canine PD-L1 and block the binding of canine PD-1 to canine PD-L1. In certain embodiments the caninized murine anti-canine PD-L1 antibodies comprise a modified canine IgGB Fc, modified canine IgGC Fc, or a modified canine IgGD lacking fab arm exchange as described herein.

The antibody or antigen binding fragment thereof that binds the canine antigen, e.g., canine PD-L1, can comprise one, two, three, four, five, or six of the complementarity determining regions (CDRs) of the murine anti-canine antibody as described herein. The one, two, three, four, five, or six CDRs may be independently selected from the CDR sequences of those provided below. In a further embodiment, the antibody or antigen-binding fragment thereof that binds canine PD-L1 comprises a canine antibody kappa light chain comprising a murine light chain CDR-1, CDR-2 and/or CDR-3 and a canine antibody heavy chain IgG comprising a murine heavy chain CDR-1, CDR-2 and/or CDR-3. Accordingly, the present invention further provides full length canine heavy chains then can be matched e.g., with the corresponding light chains to make a caninized antibody [see Table 2 below, in which the sequences of two sets of CDRs of murine anti-canine PD-L1, e.g., 4F9 and 5F12 are provided].

In other embodiments, the invention provides antibodies or antigen binding fragments thereof that bind PD-L1 with specificity and have canine antibody kappa light chains comprising one to six different CDRs comprising at least 80%, 85%, 90%, 95%, 98% or 99% sequence identity with the amino acid sequences of SEQ ID NOs: 16, 17, 18, 22, 23, and/or 24 and canine antibody heavy chain IgG comprising one to six different CDRs comprising at least 80%, 85%, 90%, 95%, 98% or 99% sequence identity with the amino acid sequences of SEQ ID NOs: 13, 14, 15, 19, 20, and/or 21, while still exhibiting the desired binding and functional properties. In another embodiment the antibody or antigen binding fragment of the present invention comprises a canine frame comprising of a combination of IgG heavy chain sequence with a kappa light chain having one or more of the above-mentioned CDR amino acid sequences with 0, 1, 2, 3, 4, or 5 conservative or non-conservative amino acid substitutions, while still exhibiting the desired binding and functional properties.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Exemplary conservative substitutions are set forth in Table I directly below.

TABLE 1

EXEMPLARY CONSERVATIVE AMINO ACID SUBSTITUTIONS

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |

TABLE 1-continued

EXEMPLARY CONSERVATIVE AMINO ACID SUBSTITUTIONS

| Original residue | Conservative substitution |
|---|---|
| Lys (K) | Arg; His |
| Met (M) | Leu; Ile; Tyr |
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table I above.

Nucleic Acids

The present invention further comprises the nucleic acids encoding the immunoglobulin chains of caninized murine anti-canine PD-L1 antibodies and antigen binding fragments thereof disclosed herein (see Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the CDRs and/or canine cFc's and/or antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences.

This present invention also provides expression vectors comprising the nucleic acids (including isolated nucleic acids) of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

A caninized murine anti-canine PD-L1 antibody for example, can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse, and hamster cells. Cell lines of particular preference are selected through determining which cell lines have high expression levels.

Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

The present invention further includes antibody fragments of the caninized murine anti-canine PD-L1 antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$-$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_V$ fragment is a $V_L$ or $V_H$ region.

In one embodiment, the antibody or antigen binding fragment comprises a heavy chain constant region, e.g., a canine constant region, such as IgGA, IgGB, IgGC and IgGD canine heavy chain constant region or a variant thereof. In another embodiment, the antibody or antigen binding fragment comprises a light chain constant region, e.g., a canine light chain constant region, such as lambda or kappa canine light chain region or variant thereof. By way of example, and not limitation the canine heavy chain constant region can be from IgGB and the canine light chain constant region can be from kappa.

Antibody Engineering

Caninized murine anti-canine PD-L1 antibodies of the present invention can be engineered to include modifications in the canine frame of a parental (i.e., canine) monoclonal antibody, e.g. to improve the properties of the antibody, as detailed below.

Cross-Blocking Antibodies and Epitope Binding

Cross-blocking antibodies and antigen-binding fragments thereof that cross-compete with 4F9 and/or 5F12, including caninized cross-blocking antibodies and antigen-binding fragments thereof, are part of the present invention. In addition, antibodies and antigen-binding fragments thereof that bind to the same epitope as any of the anti-canine PD-L1 antibodies or fragments thereof of the present invention also form part of the present invention. Cross-blocking antibodies and antigen-binding fragments can be identified based on their ability to cross-compete with 4F9 and/or 5F12 in standard binding assays (e.g., BIACore®, ELISA, or flow cytometry). For example, standard ELISA assays can be used in which a recombinant canine PD-L1 protein is immobilized on the plate, one of the antibodies is fluorescently labeled and the ability of non-labeled antibodies to compete off the binding of the labeled antibody is evaluated. Additionally or alternatively, BIAcore® analysis can be used to assess the ability of the antibodies to cross-compete. The ability of a test antibody to inhibit the binding of, for example, 4F9 and/or 5F12 to canine PD-L1 demonstrates that the test antibody can compete with 4F9 and/or 5F12 for binding to canine PD-L1 and thus, may, in some cases, bind to the same epitope on canine PD-L1 as 4F9 and/or 5F12. In more particular embodiments, cross-blocking antibodies and antigen-binding fragments thereof that cross-compete with 4F9 and/or 5F12 and also bind to the same epitope on canine PD-L1 as 4F9 and/or 5F12 are also part of the present invention.

Peptide and Fusion Protein Vaccines

Peptides comprising epitopes (or portions thereof) recognized by anti-canine PD-L1 mAbs and fusion proteins comprising such peptides may be used as vaccines to elicit antibodies that block the binding of PD-L1 to PD-1 and result in T cell activation and enhancement of the immune response. Such vaccines may be useful as therapeutic vaccines for diseases such as cancer or to act as enhancers of the immune response to other vaccines. In order to use these peptides as vaccines, one or more of these peptides may be coupled chemically or through the techniques of recombinant DNA technology to a carrier protein in order to enhance the immunogenicity of these peptides and elicit peptide-specific antibodies. Techniques for coupling peptides to carrier proteins are known to those skilled in the art. Peptide (and corresponding fusion protein) vaccines may be used to vaccinate animals by e.g., intramuscular (IM), subcutaneous (S/C), oral, spray or in ovo routes (see below too). Such vaccines may be used as subunit proteins expressed from bacterial, viral, yeast or baculovirus virus systems. Alternatively such peptide (or fusion protein) vaccines may be delivered following administration of a variety of viral or bacterial vectors that express such peptide or fusion proteins as can be practiced by methods known to those skilled in the art. The peptide or fusion protein vaccines may be administered in doses from 1-1000 µg and may optionally contain an adjuvant and an acceptable pharmaceutical carrier Pharmaceutical Compositions and Administration To prepare pharmaceutical or sterile compositions of a caninized murine anti-canine PD-L1 antibody or antigen binding fragment thereof it can be admixed with a pharmaceutically acceptable carrier or excipient. [See, e.g., *Remington's Pharmaceutical Sciences* and *U.S. Pharmacopeia: National Formulary*, Mack Publishing Company, Easton, Pa. (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) Goodman and Gilman's *The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.]. In one embodiment, anti-PD-L1 antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the caninized murine anti-canine PD-L1 antibody or antigen binding fragment thereof can be administered by an invasive route such as by injection. In further embodiments of the invention, a murine anti-canine PD-L1 antibody or antigen binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer a caninized murine anti-canine PD-L1 antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis*, Marcel Dekker, New York, N.Y. (1991); Bach (ed.) *Monoclonal Antibodies and Peptide Therapy in Autoimmune Diseases*, Marcel Dekker, New York, N.Y. (1993); Baert, et al. *New Engl. J. Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veteranarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Antibodies or antigen binding fragments thereof disclosed herein may be provided by continuous infusion, or by doses administered, e.g., daily, 1-7 times per week, weekly, biweekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of a caninized murine anti-canine PD-L1 antibody in the subject's serum, such as 0.1, 0.3, 1, 3, 10, 30, 100, 300 µg/ml or more. In other embodiments, a caninized murine anti-canine PD-L1 antibody of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of a caninized murine anti-canine PD-L1 antibody or antigen binding fragment thereof of the present invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%; and most preferably by at least 50%. An effective amount can also result in an improvement in a subjective measure in cases where subjective measures are used to assess disease severity.

Other Combination Therapies

As previously described, a caninized murine anti-canine PD-L1 antibody or antigen binding fragment thereof may be coadministered with one or other more therapeutic agents (such as a chemotherapeutic agent). The antibody may be linked to the agent (as an immunocomplex) or can be administered separately from the agent. In the latter case (separate administration), the antibody can be administered before, after or concurrently with the agent or can be co-administered with other known therapies.

In particular combination therapies, a caninized murine anti-canine PD-L1 antibody or antigen binding fragment thereof may be coadministered with a caninized murine anti-canine PD-1 antibody or antigen binding fragment thereof [e.g., as disclosed in U.S. Provisional Application Ser. No. 61/918,946, filed on Dec. 20, 2013, and U.S. Provisional Application Ser. No. 62/030,812, filed on Jul. 30, 2014, Provisional Application Ser. No. 62/092,496, filed Dec. 16, 2014, PCT/EP2014/078655 (WO2015091911), and PCTEP2014/078653 (WO2015/091910), the contents of which are all hereby incorporated by reference in their entireties] and/or a caninized murine anti-canine cytotoxic T-lymphocyte associated protein-4 (CTLA-4) antibody, or antigen binding fragment thereof. Accordingly, any combination of these three caninized murine anti-canine protein (i.e., anti-canine PD-L1, PD-1, or CTLA-4) antibodies or antigen binding fragments thereof can be co-administered. For example, the caninized murine anti-canine PD-L1 antibody or antigen binding fragment thereof can be administered before, after, or concurrently with a caninized murine anti-canine PD-1 antibody or antigen binding fragment thereof and/or with a caninized murine CTLA-4 antibody or antigen binding fragment thereof. In addition, the combination of the caninized murine anti-canine PD-L1 antibody or antigen binding fragment thereof with the caninized murine anti-canine PD-1 antibody or antigen binding fragment thereof, and/or the caninized murine CTLA-4 antibody or antigen binding fragment thereof also can be co-administered with other known therapies, i.e., before, after, or concurrently.

Kits

Further provided are kits comprising one or more components that include, but are not limited to, an antibody or antigen binding fragment, as discussed herein, which specifically binds PD-L1 (e.g., a caninized murine anti-canine PD-L1 antibody or antigen binding fragment thereof) in association with one or more additional components including, but not limited to a caninized murine anti-canine PD-1 antibody or antigen binding fragment thereof, and/or a caninized murine anti-canine CTLA-4 antibody or antigen binding fragment thereof, a pharmaceutically acceptable carrier and/or a chemotherapeutic agent, as discussed herein. In alternative embodiments, the kit can comprise one or more peptide comprising an epitope or portion thereof (or a fusion protein comprising the epitope or portion thereof) recognized by anti-canine PD-L1 mAbs as discussed above. The binding composition and/or the chemotherapeutic agent or the peptide comprising an epitope or portion thereof (or a fusion protein comprising the epitope or portion thereof) can be formulated as a pure composition or in combination with a pharmaceutically acceptable carrier, in a pharmaceutical composition.

In one embodiment, the kit includes a binding composition of the present invention, e.g., a caninized murine anti-canine PD-L1 (or antigen binding fragment thereof) or a pharmaceutical composition thereof in one container (e.g., in a sterile glass or plastic vial) and/or a pharmaceutical composition thereof and/or a chemotherapeutic agent in another container (e.g., in a sterile glass or plastic vial) and/or a caninized murine anti-canine PD-1 (or antigen binding fragment thereof) and/or a caninized murine anti-canine CTLA-4 (or antigen binding fragment thereof) or a pharmaceutical composition thereof in one or more other containers (e.g., in a sterile glass or plastic vial).

If the kit includes a pharmaceutical composition for parenteral administration to a subject, the kit can also include a device for performing such administration. For example, the kit can include one or more hypodermic needles or other injection devices as discussed above. The kit can also include a package insert including information concerning the pharmaceutical compositions and dosage forms in the kit. Generally, such information aids pet owners and veterinarians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

Example 1

Canine PD-1 and PD-L1

Canine PD-1 and PD-L1 Sequences:

U.S. provisional application No. 61/918,946, filed on Dec. 20, 2013 and 62/030,812, filed on Jul. 30, 2014, hereby incorporated by reference in their entireties, provides: the full length nucleotide sequence for canine PD-1 (cPD-1) of SEQ ID NO: 49 [SEQ ID NO: 69 includes the signal sequence]; the corresponding translated amino acid sequence of SEQ ID NO: 50 [SEQ ID NO: 70 includes the signal sequence]; the nucleotide sequence encoding the extra-cellular domain (ECD) of canine PD-1, SEQ ID NO: 51; the amino acid sequence of the ECD of canine PD-1, SEQ ID NO: 52; the nucleotide sequence of canine PD-1 ECD plus a GT linker and the Fc part of human IgG1 Fc gene, SEQ ID NO: 53; and the amino acid sequence of the canine PD-1 ECD plus a GT linker and the Fc part of human IgG1 Fc gene, SEQ ID NO: 54 [SEQ ID NO: 81 includes the signal sequence].

U.S. provisional application No. 61/918,946, filed on Dec. 20, 2013 and 62/030,812, filed on Jul. 30, 2014, hereby incorporated by reference in their entireties further provide: the full length nucleotide sequence for canine PD-L1 (cPD-L1) of SEQ ID NO: 55 [SEQ ID NO: 71 includes the signal sequence]; the corresponding translated amino acid sequence of SEQ ID NO: 56 [SEQ ID NO: 72 includes the signal sequence]; the nucleotide sequence encoding the extra-cellular domain (ECD) of canine PD-L1, SEQ ID NO: 57; the amino acid sequence of the ECD of canine PD-L1, SEQ ID NO: 58; the nucleotide sequence of canine PD-L1 ECD plus a GT linker and the Fc part of human IgG1 Fc gene, of SEQ ID NO: 59; and the amino acid sequence of the PD-L1 ECD plus a GT linker and the Fc part of human IgG1 Fc gene, SEQ ID NO: 60.

Identification and Cloning of Canine PD-1:

A nucleic acid encoding a full length canine PD-1 (cPD-1) was identified through a search of the NCBI gene bank data bases (accession number XM_543338.4). The translated amino acid sequence (accession number XP_543338.3) corresponded to a putative canine PD-1 protein which was further identified through searching the gene bank (NCBI) protein databases and aligning the identified amino acid sequence with murine, feline, and human PD-1 amino acid sequences. The DNA sequence corresponding to the full length canine PD-1 gene that was codon optimized for CHO cells was synthesized and cloned into a plasmid designated p96793. Comparison of DNA and protein sequences of predicted canine PD-1 with known PD-1 DNA and protein sequences led to the identification of the DNA sequences encoding the extra-cellular domain (ECD) of canine PD-1 and the amino acid sequence of the ECD of canine PD-1.

A DNA sequence encoding the ECD of canine PD-1 in addition to a GT linker and 8 histidine residues was synthesized and cloned into a plasmid designated LPD2726. A nucleic acid sequence corresponding to the canine PD-1 ECD plus a GT linker and the Fc part of human IgG1 Fc gene was chemically synthesized and cloned into a plasmid designated LPD2727. Canine PD-1 ECD and the Fc part of human IgG1 Fc comprises the amino acid sequence of SEQ ID NO: 81 (including the signal sequence).

Identification and Cloning of Canine PD-L1:

A nucleic acid encoding a full length canine PD-L1 was identified through a search of the NCBI gene bank data bases (accession number XM_541302.4). The translated amino acid sequence (accession number XP-541302.4) corresponding to the putative canine PD-L1 protein was identified by searching the gene bank (NCBI) protein databases and alignment of the identified sequence with known PD-L1 mouse and human sequences.

Comparison of DNA encoding canine PD-L1 with known PD-L1 sequences identified the DNA sequence corresponding to the ECD domain of canine PD-L1 (which was codon optimized for CHO cells). The predicted amino acid sequence of the ECD of canine PD-L1 is SEQ ID NO: 58. DNA encoding PD-L1 ECD plus GT linker and 8 histidine residues was synthesized and cloned into a plasmid designated LPD2695.

A DNA sequence encoding the amino acid sequence of canine PD-L1 ECD plus GT linker and the Fc part of human IgG1 Fc was chemically synthesized and cloned into a plasmid designated LPD2697. Canine PD-L1 ECD plus GT linker and the Fc part of human IgG1 comprises the amino acid sequence of SEQ ID NO:60.

Expression of PD-1 and PD-L1 Proteins:

Expression plasmids encoding the PD-1ECD-HIS, PD-1ECD-Fc, PD-L1 ECD-HIS, and PD-L1ECD-Fc proteins were transfected into HEK 293 cells and the proteins were purified from the supernatant of transfected cells using Protein A for Fc fusion proteins or Nickel ($Ni^{2+}$) column chromatography for HIS-tagged proteins. Purified proteins were used for: ELISA or binding assays as detailed below. Expressed proteins were analyzed by SDS-PAGE gels.

```
Full length canine PD-1 DNA sequence: signal sequence underlined and in bold
Nucleotide sequence SEQ ID NO: 49, is without the signal sequence.
atggggagccggcgggggccctggccgctcgtctgggccgtgctgcagctgggctggtggccagg
``` atggctcctagactcccctgacaggccctggagcccgctcaccttctccccggcgcagctcacgg tgcaggagggagagaacgccacgttcacctgcagcctggccgacatccccgacagcttcgtgctc aactggtaccgcctgagccccgcaaccagacggacaagctggccgccttccaggaggaccgcat cgagccgggccgggacaggcgcttccgcgtcatgcggctgcccaacgggcgggacttccacatga gcatcgtcgctgcgcgcctcaacgacagcggcatctacctgtgcggggccatctacctgccccc aacacacagatcaacgagagtccccgcgcagagctctccgtgacggagagaaccctggagccccc cacacagagcccagccccccacccagactcagcggccagttgcagggctggtcatcggcgtca cgagcgtgctggtgggtgtcctgctactgctgctgctgacctgggtcctggccgctgtcttcccc agggccaccgaggtgcctgtgtgtgcgggagcgaggacgagcctctgaaggagggccccgatgc agcgcccgtcttcaccctggactacggggagctggacttccagtggcgagagaagacgccggagc ccccggcgccctgtgccccggagcagaccgagtatgccaccatcgtcttcccgggcaggccggcg tccccgggccgcagggcctcggccagcagcctgcagggagcccagcctccgagccccgaggacgg acccggcctgtggcccctctga Full length canine PD-1 Amino acid sequence: signal sequence underlined and in bold
Amino acid sequence SEQ ID NO: 50 is without the signal sequence.
MGSRRGPWPLVWAVLQLGWWPGWLLDSPDRPWSPLTFSPAQLTVQEGENATFTCSLADIPDSFVL

NWYRLSPRNQTDKLAAFQEDRIEPGRDRRFRVMRLPNGRDFHMSIVAARLNDSGIYLCGAIYLPP

NTQINESPRAELSVTERTLEPPTQSPSPPPRLSGQLQGLVIGVTSVLVGVLLLLLLTWVLAAVFP

RATRGACVCGSEDEPLKEGPDAAPVFTLDYGELDFQWREKTPEPPAPCAPEQTEYATIVFPGRPA

SPGRRASASSLQGAQPPSPEDGPGLWPL

Canine PD-1 extracellular domain DNA sequence: SEQ ID NO: 51 (Codon optimized
for expression in CHO cells)
ctggattccccgacagaccctggagccctctcaccttctccctgcccagctgaccgtccagga aggcgagaatgccaccttcacctgcagcctcgccgacatccccgacagcttcgtgctgaactggt acagactgagccccaggaaccagaccgacaagctggccgcttttccaggaggacaggatcgaaccc ggcagggacaggaggtttagggtcatgaggctgcccaacggcagggacttccacatgtccatcgt ggccgccagactgaacgactccggcatctacctgtgcggcgctatctacctgccccccaacaccc agatcaacgagagcccagggccgaactgagcgtgacagagagaaccctggaacctccacccag agcccttcccctcctcctagactgagcggacagctgcagggcctggtg Canine PD-1 extracellular domain:
                                                                    SEQ ID NO: 52
LDSPDRPWSPLTFSPAQLTVQEGENATFTCSLADIPDSFVLNWYRLSPRNQTDKLAAFQEDRIEP
GRDRRFRVMRLPNGRDFHMSIVAARLNDSGIYLCGAIYLPPNTQINESPRAELSVTERTLEPPTQ
SPSPPPRLSGQLQGLV Canine PD-1 extracellular domain-human IgG1 Fc DNA sequence:
(Codon optimized for expression in HEK-293 cells)
                                                                    SEQ ID NO: 53
ctggattccccgacagaccctggagccctctcaccttctccctgcccagctgaccgtccagga aggcgagaatgccaccttcacctgcagcctcgccgacatccccgacagcttcgtgctgaactggt acagactgagccccaggaaccagaccgacaagctggccgcttttccaggaggacaggatcgaaccc ggcagggacaggaggtttagggtcatgaggctgcccaacggcagggacttccacatgtccatcgt ggccgccagactgaacgactccggcatctacctgtgcggcgctatctacctgccccccaacaccc agatcaacgagagcccagggccgaactgagcgtgacagagagaaccctggaacctccacccag agcccttcccctcctcctagactgagcggacagctgcagggcctggtgggtaccgacaaaactca cacatgcccaccgtgcccagcacctgaactcctggggggaccgtcagtcttcctcttccccccaa aacccaaggacaccctcatgatctcccggacccctgaggtcacatgcgtggtggtggacgtgagc

```
cacgaagaccctgaggtcaagttcaactggtacgtggacggcgtggaggtgcataatgccaagac aaagccgcgggaggagcagtacaacagcacgtaccgtgtggtcagcgtcctcaccgtcctgcacc aggactggctgaatggcaaggagtacaagtgcaaggtctccaacaaagccctcccagccccatc gagaaaccatctccaaagccaaagggcagccccgagaaccacaggtgtacaccctgccccatc ccgggatgagctgaccaagaaccaggtcagcctgacctgcctggtcaaaggcttctatcccagcg acatcgccgtggagtgggagagcaatgggcagccggagaacaactacaagaccacgcctcccgtg ctggactccgacggctccttcttcctctacagcaagctcaccgtggacaagagcaggtggcagca ggggaacgtcttctcatgctccgtgatgcatgaggctctgcacaaccactacacgcagaagagcc tctccctgtctccgggtaaatga
```

Canine PD-1 extracellular domain-human IgG1 Fc fusion protein: signal sequence
underlined and in bold: amino acid SEQ ID NO: 54 is without the signal sequence.
MNFLLSWVHWSLALLLYLHHAKWSQALDSPDRPWSPLTFSPAQLTVQEGENATFTCSLADIPDSF

VLNWYRLSPRNQTDKLAAFQEDRIEPGRDRRFRVMRLPNGRDFHMSIVAARLNDSGIYLCGAIYL

PPNTQINESPRAELSVTERTLEPPTQSPSPPPRLSGQLQGLVGTDKTHTCPPCPAPELLGGPSVF

LFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHY

TQKSLSLSPGK

Full length canine PD-L1 DNA sequence: signal sequence underlined and in
bold Nucleotide sequence SEQ ID NO: 55 is without the signal sequence.
atgagaatgtttagtgtctttacattcatggcctactgccatttgctaaaagcatttacgatcac agtttctaaggacctgtatgtggtagagtatggtggcaatgtgacaatggaatgcaaattcccgg tggaaaaacagttaaacttgtttgcactaatcgtctactgggaaatggaggataaaaaaattata caatttgtgaatggaaaggaagacctgaaagttcagcacagcagctacagccagagggctcagct attgaaggaccagctcttcttggggaaggctgcgcttcagatcacagatgtgagattgcaggatg caggggtttactgctgcttgatcggctatggcggtgctgactacaagcggattactttgaaagtt catgccccgtaccgcaacatcagccaaagaatttctgtggatcctgtcacctctgaacatgaact aatgtgtcaggctgagggttaccctgaggctgaagtcatctggacaagcagtgaccaccgagtcc tgagtggcaaaaccaccatcactaattccaatagggaagagaagcttttcaatgtgaccagcacg ctgaacatcaatgcaacagctaatgagattttctactgcacttttcaaagatcaggtcctgagga aaacaatactgccgagttggtcatcccagaacgactgcccgttccagcaagtgagaggactcatt tcatgattctgggaccttcctgttgcttcttggtgtagtcctggcagtcactttctgtctaaaa aaacatgggagaatgatggatgtggaaaaatgttgcacccgagataggaactcaaagaaacgaaa tgatatacaatttgaagagacataa Full length canine PD-L1: signal sequence underlined and in bold Amino acid sequence
SEQ ID NO: 56 is without the signal sequence.
MRMFSVFTFMAYCHLLKAFTITVSKDLYVVEYGGNVTMECKFPVEKQLNLFALIVYWEMEDKKII

QFVNGKEDLKVQHSSYSQRAQLLKDQLFLGKAALQITDVRLQDAGVYCCLIGYGGADYKRITLKV

HAPYRNISQRISVDPVTSEHELMCQAEGYPEAEVIWTSSDHRVLSGKTTITNSNREEKLFNVTST

LNINATANEIFYCTFQRSGPEENNTAELVIPERLPVPASERTHFMILGPFLLLLGVVLAVTFCLK

KHGRMMDVEKCCTRDRNSKKRNDIQFEET

Canine PD-L1 extracellular domain DNA sequence: SEQ ID NO: 57 (Codon optimized
for expression in CHO cells)
tttaccatcaccgtgtccaaggacctgtacgtggtcgagtacggcggcaatgtgaccatggagtg caagttccccgtggagaagcagctgaacctgttcgcccctcatcgtgtactgggagatggaggaca -continued agaagatcatccagttcgtgaacggcaaggaggacctgaaggtgcagcactccagctactcccag agagcccagctgctgaaggaccagctgttcctgggcaaggccgccctgcagatcaccgacgtgag actgcaggacgccggcgtgtattgctgcctgatcggctacggaggcgccgactacaagaggatca ccctgaaggtgcatgcaccctacaggaacatcagccagaggatcagcgtcgatcccgtgaccagc gagcacgagctgatgtgccaagccgagggctatcccgaggccgaagtgatctggaccagcagcga ccacagggtcctgagcggcaagaccaccatcaccaacagcaacagggaggagaagctgttcaacg tgaccagcaccctcaacatcaacgccaccgccaacgagatcttctactgcaccttccagaggagc ggccccgaagagaacaacaccgccgagctggtgatccccgagagactgcctgtgcctgccagcga gaggacccac Canine PD-L1 extracellular domain protein:

SEQ ID NO: 58

FTITVSKDLYVVEYGGNVTMECKFPVEKQLNLFALIVYWEMEDKKIIQFVNGKEDLKVQHSSYSQ

RAQLLKDQLFLGKAALQITDVRLQDAGVYCCLIGYGGADYKRITLKVHAPYRNISQRISVDPVTS

EHELMCQAEGYPEAEVIWTSSDHRVLSGKTTITNSNREEKLFNVTSTLNINATANEIFYCTFQRS

GPEENNTAELVIPERLPVPASERTH

Canine PD-L1 extracellular domain-human IgG1 Fc DNA sequence:
(Codon optimized for expression in HEK-293 cells)

SEQ ID NO: 59 tttaccatcaccgtgtccaaggacctgtacgtggtcgagtacggcggcaatgtgaccatggagtg caagttccccgtggagaagcagctgaacctgttcgccctcatcgtgtactgggagatggaggaca agaagatcatccagttcgtgaacggcaaggaggacctgaaggtgcagcactccagctactcccag agagcccagctgctgaaggaccagctgttcctgggcaaggccgccctgcagatcaccgacgtgag actgcaggacgccggcgtgtattgctgcctgatcggctacggaggcgccgactacaagaggatca ccctgaaggtgcatgcaccctacaggaacatcagccagaggatcagcgtcgatcccgtgaccagc gagcacgagctgatgtgccaagccgagggctatcccgaggccgaagtgatctggaccagcagcga ccacagggtcctgagcggcaagaccaccatcaccaacagcaacagggaggagaagctgttcaacg tgaccagcaccctcaacatcaacgccaccgccaacgagatcttctactgcaccttccagaggagc ggccccgaagagaacaacaccgccgagctggtgatccccgagagactgcctgtgcctgccagcga gaggacccacggtaccgacaaaactcacacatgcccaccgtgcccagcacctgaactcctggggg gaccgtcagtcttcctcttccccccaaaacccaaggacaccctcatgatctcccggacccctgag gtcacatgcgtggtggtggacgtgagccacgaagaccctgaggtcaagttcaactggtacgtgga cggcgtggaggtgcataatgccaagacaaagccgcgggaggagcagtacaacagcacgtaccgtg tggtcagcgtcctcaccgtcctgcaccaggactggctgaatggcaaggagtacaagtgcaaggtc tccaacaaagccctcccagcccccatcgagaaaaccatctccaaagccaaagggcagccccgaga accacaggtgtacaccctgcccccatcccgggatgagctgaccaagaaccaggtcagcctgacct gcctggtcaaaggcttctatcccagcgacatcgccgtggagtgggagagcaatgggcagccggag aacaactacaagaccacgcctcccgtgctggactccgacggctccttcttcctctacagcaagct caccgtggacaagagcaggtggcagcaggggaacgtcttctcatgctccgtgatgcatgaggctc tgcacaaccactacacgcagaagagcctctccctgtctccgggtaaatga Canine PD-L1 extracellular domain-human IgG1 Fc fusion protein:

SEQ ID NO: 60

FTITVSKDLYVVEYGGNVTMECKFPVEKQLNLFALIVYWEMEDKKIIQFVNGKEDLKVQHSSYSQ

RAQLLKDQLFLGKAALQITDVRLQDAGVYCCLIGYGGADYKRITLKVHAPYRNISQRISVDPVTS

EHELMCQAEGYPEAEVIWTSSDHRVLSGKTTITNSNREEKLFNVTSTLNINATANEIFYCTFQRS

```
GPEENNTAELVIPERLPVPASERTHGTDKTHTCPPCPAPELLGGPSVFLFPPKPKDTLMISRTPE

VTCVVVDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPGK
```

Example 2

Murine Anti-Canine Pd-L1 Antibodies

Generation of Anti-Canine PD-L1 Monoclonal Antibodies:

A total of three Balb/c mice were immunized multiple times (with 10 µg each time) over a 17 day period. The immunizing antigen was the canine PD-L1 ECD-Fc fusion protein. Following immunization, serum was collected from each mouse and tested for reactivity with canine PD-L1 ECD-HIS tagged protein. The spleen cells of the mouse with the highest serum anti-PD-L1 ECD-HIS titer were fused to the myeloma P3X63Ag8.653 cell line. Approximately 2 weeks following fusion, supernatant from putative hybridoma cells were tested by ELISA for their reactivity to the PD-L1 ECD-HIS tagged protein. Hybridomas producing strong positive signals in the ELISA were subcloned by limiting dilution and tested again for reactivity to canine PD-L1 ECD-HIS tagged protein.

Confirmation of Monoclonal Antibodies Reactivity Against Canine PD-L1:

The reactivity of antibodies secreted by hybridomas to ECD of canine PD-L1 was confirmed by ELISA. Hybridoma cells were cultured using CELLine bioreactors (Integra-biosciences) for 10-30 days. Cells were initially maintained in DMEM supplemented with 4 mM L-glutamine and 10% Ultra Low IgG fetal bovine serum (FBS) from Gibco. Hybridoma cells were seeded in CELLine bioreactor cell chambers at a cell density of approximately $2\times10^6$ cells/mL in 15 mL of the same medium with the FBS concentration increased to 20%. The outer chamber was filled with 1 L of nutrient medium (DMEM with 4 mM L-glutamine and 2% standard FBS). Hybridoma cells in the cell chamber were expanded to approximately $2.5\times10^7$ cells/mL over 3-7 days. Then, 10 mL of cell suspension was harvested from the cell chamber and replaced with fresh media to allow for re-expansion of cells and subsequent harvests. This procedure was repeated as necessary to obtain adequate amounts of mAb from each hybridoma clone. Harvested cell suspensions were centrifuged and the supernatants were filtered through 0.2 micron filter membranes. For antibody purification, each clone's supernatant was purified using a Protein G Sepharose 4 Fast flow 5 mL column (GE Healthcare) by gravity flow. After washing with Tris-EDTA (TE) buffer pH 8.0, bound antibodies were eluted using 0.1 M glycine buffer, pH 2.7, followed by pH neutralization using 1 M Tris, pH 8.0. Antibodies were concentrated and buffer exchanged into phosphate-buffered saline (PBS) using Centriprep YM-10.10 kDa NMWL centrifugal filter units (Millipore). Antibody concentrations were quantified using spectrophotometry. Purified anti-canine PD-L1 mAbs were tested for reactivity with canine PD-L1-hFc fusion protein by ELISA as follows: Canine PD-L1-hFc fusion protein is diluted to 10 µg/mL in coating buffer (Carbonate/Bicarbonate pH 9.0) and dispensed at 100 µl/well in 96-well flat bottomed ELISA plates (NUNC). The plates are incubated at 4° C. overnight. The plates are then washed three times with phosphate buffered saline containing 0.05% Tween-20 (PBST). Next, 200 µl of blocking buffer (5% skim milk in PBST) is added to each well and the plates are incubated at 37° C. for 60 minutes. The plates are then washed three times with PBST. Next, 100 µl of test mAbs diluted in blocking buffer is added to the first wells of the appropriate columns. Test mAbs are then diluted two-fold to the appropriate plate position. Following incubation of the plates at 37° C. for 60 minutes, the plates are washed three times with PBST. Next, 100 µl per well of a 1:2,000 dilution of a horseradish peroxidase conjugated goat anti-mouse IgG (KPL) is added to the plates, which are then incubated at 37° C. for 60 minutes. Then the plates are washed three times with PBST, and 100 µl/well of 3,3',5,5' tetramethyl benzidine, (TMB) substrate (from KPL) is added to the plates. The color reaction is allowed to develop for 5-20 minutes at 37° C. prior to measuring absorbance at 650 nm.

CHO Cells Expressing Canine PD-1 Protein:

The full length canine PD-1 gene was cloned into plasmid p96793. In this plasmid the expression of the PD-1 protein is driven by an hCMV promoter. CHO DXB11 cells (dhfr-) were maintained in MEM-alpha (Gibco) supplemented with 10% fetal bovine serum. Transfection of CHO cells with plasmid p96793 was carried out in 75 cm² flasks containing approximately $6\times10^6$ cells by liposome-mediated gene delivery using Lipofectamine (Invitrogen). After 48 hours, cells were passaged into MEM-alpha medium without nucleosides, supplemented with 10% FBS and 400 µg/mL hygromycin B (selective medium). Limited-dilution cloning was performed on the pool of dhfr+, hygromycin resistant cells. Clones were assessed for expression of canine PD-1 by immunofluorescence assay. Briefly, cell monolayers were fixed in 96 well plates with 80% acetone. Fixed and dried cell monolayers were then incubated for 1 hour with a polyclonal goat anti-human PD-1 antibody (R&D Systems). Plates were washed with PBS, and then incubated for 1 hour with a fluorescein-labeled rabbit anti-goat IgG antibody (KPL). Plates were washed with PBS. Clones exhibiting fluorescence were expanded and cell stocks were established.

Ligand Blockade by Mouse Anti-PD-L1 mAbs:

A cell-based ELISA (CELISA) assay based on the CHO cell line expressing canine PD-1 was used to demonstrate the ability of mouse anti-canine PD-L1 antibodies to block the interaction between (e.g., block the binding of) canine PD-L1 and its receptor canine PD-1. Ligand blockade was confirmed using this assay in conjunction with canine PD-L1/h Fc protein as follows:

1. Seed cPD-1 CHO cells in 96-well plates and grow the cells to 95-100% confluent.
    General guidelines for plating CHO cells,
        on day −3: $1\times10^3$ c/well ($1\times10^5$ c/mL)
            −2: $2\times10^4$ c/well ($2\times10^5$ c/mL)
            1: $−4\times10^4$ c/well ($4\times10^5$ c/mL)
2. 3-fold dilute anti-cPDL1 mAbs in CHO media, starting at 30 µg/mL, 100 µL/well. Add cPD-L1-hFc to 4 µg/ml in CHO media, 100 μL/well, co-incubate in a dilution plate at 37° C., 5% $CO_2$ with shaking for 60 min.

3. Aspirate cell culture media from the cell coated plates, wash the plates 3×PBS+0.05% Tween20 and 1×CHO media.
4. Add the co-incubated cPD-L1 mAbs/PD-L1 Fc from the dilution plate to the cell coated plate. 100 uL/well. Incubate at 37° C., 5% $CO_2$ with shaking for 60 min.
5. Wash the plates 6×PBS+0.05% Tween 20 (using manual wash protocol).
6. Add Anti-Human Fc-HRP (Calbiochem) (1:2500) in CHO media, 100 ul/well, incubate 30-60 min at 37° C./5% $CO_2$.
7. Wash the plates 5×PBS+0.05% Tween20 (using manual wash protocol).
8. Add 100 μl/well TMB mircowell substrate. Incubate at room temp for 10 minutes. Use one step substrate from Pierce.
9. Stop with 100 μl/well 1.5M Phosphoric acid.
10. Measure A450-A620 on the ELISA reader.

Cloning and Identification of DNA Sequences Corresponding to Mouse Anti-Canine PD-L1 mAbs Variable Regions:

The DNA sequence of mouse VH and VL chains and the DNA sequences encoding their CDRs are identified following isolation of mRNA from each hybridoma using standard molecular biology methods. The sequences of the variable regions of heavy and light chains of the two antibodies exemplified herein are provided in Table 12 below. The SEQ ID NOs. of predicted amino acid sequences of the CDRs from these hybridomas are listed in Table 2 below:

TABLE 2

AMINO ACID SEQUENCES OF THE CDRs

|  |  | SEQ ID NO. |
|---|---|---|
| 4F9 | | |
| VH CDR1 | SYAMS | 13 |
| VH CDR2 | TISDGGSYTHYPDNLMG | 14 |
| VH CDR3 | ESYDGYYVAN | 15 |
| VL CDR1 | RASQSISNNLH | 16 |
| VL CDR2 | YASQSIS | 17 |
| VL CDR3 | QQSNSWPQT | 18 |
| 5F12 | | |
| VH CDR1 | DYYMN | 19 |
| VH CDR2 | WIFPGSGATYYNERFMG | 20 |
| VH CDR3 | SDWDVGDF | 21 |
| VL CDR1 | RSSRSLLHTNGITYLS | 22 |
| VL CDR2 | QMSNLAS | 23 |
| VL CDR3 | AQTLGLPRT | 24 |

Canonical structures (classes) for VH chain CDRs mAbs: 4F9:   CDR1: H1-1;   CDR2: H2-3B;   CDR3: H3-10
mAb: 5F12:   CDR1: H1-1;   CDR2: H2-3B;   CDR3: H3-8

TABLE 2-continued

AMINO ACID SEQUENCES OF THE CDRs

Canonical structures (classes) for VL chain CDRs mAbs: 4F9:   CDR1: L1-2;   CDR2: L2-1;   CDR3: L3-1
mAbs: 5F12:  CDR1: L1-3;   CDR2: L2-1;   CDR3: L3-1

Example 3

Caninization and Characterization of Caninized Antibodies

In order to produce caninized antibodies it was necessary to identify the DNA sequence encoding the heavy and light chains of canine IgG. The nucleotide and amino acid sequences of the canine heavy chain can be obtained from the NCBI gene and protein databases. There are four known IgG subclasses of canine IgG: IgGA, IgGB, IgGC, and IgGD and two types of light chains: kappa and lambda. Table 7 lists the amino acid and nucleotide SEQ ID NOs of the unmodified canine Fc fragments.

Without being bound by any specific approach, the process of producing variants of anti-PD-L1 monoclonal antibodies with various contents of canine and mouse sequences involved the general following scheme:

i) Determine the nucleotide sequence of VH and VL chains of mouse mAbs;
ii) Identify the H and L chain CDRs of mouse mAbs;
iii) Identify a suitable H and L chain of canine IgG;
iv) Determine the nucleotide sequence of canine IgG H and L chains;
v) Replace the nucleotide sequence encoding endogenous canine H and L chain CDRs with nucleotide sequences encoding the respective mouse CDRs. Also, optionally replace some canine framework residues with selected residues from the mouse framework regions;
vi) Synthesize the nucleotide from step (v) and insert it into a suitable expression plasmid; Transfect plasmids into appropriate cells, e.g., HEK 293 cells;
vii) Purify the expressed antibody from HEK 293 supernatent; and
viii) Test purified antibody for binding to canine PD-L1.

Example 4

Genetically Modified Canine IgGs

In order to generate variants of canine IgG that lack effector functions, a number of mutant canine IgGB heavy chains were generated [see, U.S. provisional application No. 62/030,812, filed on Jul. 30, 2014, hereby incorporated by reference in its entirety]. These variants may include one of the following single or combined substitutions in the Fc portion of the heavy chain amino acid sequence: P4A, D31A, N63A, G64P, T65A, A93G, and P95A. Variant heavy chains (i.e., containing such amino acid substitutions) were cloned into expression plasmids and transfected into HEK 293 cells along with a plasmid containing the gene encoding a light chain. Intact antibodies expressed and purified from HEK 293 cells were evaluated for binding to $Fc_1RI$ and Clq to assess their potential for mediation of immune effector functions. Table 3 lists examples of the plasmids encoding the genetically modified caninized heavy chains, the caninized heavy chains; and the genetic modifications in these heavy chains. The variant heavy chains were used for assessment of effector function in the genetically modified mAbs. All of the heavy chains comprised the CDRs from murine anti-canine PD-1 antibodies. [See, U.S. provisional application No. 62/030,812, supra]

TABLE 3

| Plasmid | Heavy chain | Modification | AA position in native Fc |
|---|---|---|---|
| YZZ1057/Mut-1 | can2H9VH4 | D31 to A | D31 |
| YZZ1058/Mut-2 | can2H9VH4 | N63 to A | N63 |
| YZZ1062 | can2H9VH4 | D31 to A + N63 to A | D31 and N63 |
| YZZ1059 | can2H9VH4 | P4 to A | P4 |
| YZZ1060 | can2H9VH4 | A93 to G | A93 |
| YZZ1061 | can2H9VH4 | P95 to A | P95 |
| YZZ1068 | can2H9VH4 | D31 to A, N63 to A, P4 to A, A93 to G, and P95 to A | D31, N63, P4, A93, P95 |

TABLE 4

MODIFIED cFc or NATIVE cFc WITH HINGE SEQUENCES

| # | N. | A. | Modified Fcs |
|---|---|---|---|
| 1* | ✓ |  | Modified Fc -cIgGB |
| 2* |  | ✓ | Modified Fc -cIgGB |
| 3* | ✓ |  | Modified Fc -cIgGC |
| 4* |  | ✓ | Modified Fc -cIgGC |
| 5# | ✓ |  | cIgGD Fc with S of cIgGD hinge to P |
| 6# |  | ✓ | cIgGD Fc with S of cIgGD hinge to P |
| 7 | ✓ |  | cIgGD Fc with A hinge |
| 8 |  | ✓ | cIgGD Fc with A hinge |
| 9 | ✓ |  | cIgGD Fc with B hinge |
| 10 |  | ✓ | cIgGD Fc with B hinge |
| 11 | ✓ |  | cIgGD Fc with C hinge |
| 12 |  | ✓ | cIgGD Fc with C hinge |

*The substitutions are at P4, D31, N63, G64, T65, A93, and P95 of amino acid sequences SEQ ID NOs: 2 and 4; or at the nucleotides that encode those amino acids for nucleotide sequences SEQ ID NOs: 1 and 3.
Single amino acid substitution as shown in Table 5 below in hinge region of IgGD.

TABLE 5

HINGE REGION SEQUENCES

| # | A.A. | Hinge | Sequence |
|---|---|---|---|
| 45 | ✓ | IgGA | FNECRCTDTPPCPVPEP |
| 46 | ✓ | IgGB | PKRENGRVPRPPDCPKCPAPEM |
| 47 | ✓ | IgGC | AKECECKCNCNNCPCPGCGL |
| 48 | ✓ | IgGD# | PKESTCKCIPPCPVPES |

Single amino acid substitution of a serine to a proline as in bold and underlined.

TABLE 6

CANINE PD-1/PD-L1 SEQUENCES

| # | N. | A. | PD-1 Description | # | N. | A. | PD-L1 Description |
|---|---|---|---|---|---|---|---|
| 49 | ✓ |  | Full Length | 55 | ✓ |  | Full Length |
| 50 |  | ✓ | Full Length | 56 |  | ✓ | Full Length |
| 51 | ✓ |  | ECD | 57 | ✓ |  | ECD |
| 52 |  | ✓ | ECD | 58 |  | ✓ | ECD |
| 53 | ✓ |  | cECD-hIgG1 | 59 | ✓ |  | cECD-hIgG1 |
| 54 |  | ✓ | cECD-hIgG1 | 60 |  | ✓ | cECD-hIgG1 |

TABLE 6-continued

CANINE PD-1/PD-L1 SEQUENCES

| # | N. | A. | PD-1 Description | # | N. | A. | PD-L1 Description |
|---|---|---|---|---|---|---|---|
| 69 | ✓ |  | +signal seq. | 71 | ✓ |  | +signal seq. |
| 70 |  | ✓ | +signal seq. | 72 |  | ✓ | +signal seq. |
| 81 | ✓ |  | +signal seq. |  |  |  |  |

TABLE 7

NATIVE cFc SEQUENCES

| # | N. | A. |  |
|---|---|---|---|
| 61 | ✓ |  | Fc-cIgGA |
| 62 |  | ✓ | Fc-cIgGA |
| 63 | ✓ |  | Fc-cIgGD |
| 64 |  | ✓ | Fc-cIgGD |
| 65 | ✓ |  | Fc-cIgGB |
| 66 |  | ✓ | Fc-cIgGB |
| 67 | ✓ |  | Fc-cIgGC |
| 68 |  | ✓ | Fc-cIgGC |

TABLE 8

CDR AMINO ACID SEQUENCES

| # | A.A. | CDR |
|---|---|---|
| 13 | ✓ | VH CDR1 4F9 |
| 14 | ✓ | VH CDR2 4F9 |
| 15 | ✓ | VH CDR3 4F9 |
| 16 | ✓ | VL CDR1 4F9 |
| 17 | ✓ | VL CDR2 4F9 |
| 18 | ✓ | VL CDR3 4F9 |
| 19 | ✓ | VH CDR1 5F12 |
| 20 | ✓ | VH CDR2 5F12 |
| 21 | ✓ | VH CDR3 5F12 |
| 22 | ✓ | VL CDR1 5F12 |
| 23 | ✓ | VL CDR2 5F12 |
| 24 | ✓ | VL CDR3 5F12 |

TABLE 9

INDIVIDUAL SUBSTITUTED CANINIZED HEAVY CHAINS

| # | N. | A. |  |
|---|---|---|---|
| 25 | ✓ |  | 4F6- VH3-CH1-hinge-FC -cIgGB Fc |
| 26 |  | ✓ | 4F6- VH3-CH1-hinge-FC -cIgGB Fc |
| 27 | ✓ |  | 4F6- VH3-CH1-hinge-FC -cIgGC Fc |
| 28 |  | ✓ | 4F6- VH3-CH1-hinge-FC -cIgGC Fc |
| 29 | ✓ |  | 5F12- VH3-CH1-hinge-FC -cIgGB Fc |
| 30 |  | ✓ | 5F12- VH3-CH1-hinge-FC -cIgGB Fc |
| 31 | ✓ |  | 5F12- VH3-CH1-hinge-FC -cIgGC Fc |
| 32 |  | ✓ | 5F12- VH3-CH1-hinge-FC -cIgGC Fc |

The potential specific substitutions are at P4, D31, N63, G64, T65, A93, and P95

TABLE 10

CORRELATION OF AMINO ACID RESIDUE POSITIONS #

| 66/68 | P4 | D31 | N63 | G64 | T65 | A93 | P95 |
|---|---|---|---|---|---|---|---|
| 2/4 | 4 | 31 | 63 | 64 | 65 | 93 | 95 |
| 26 | 242 | 269 | 301 | 302 | 303 | 331 | 333 |
| 28 | 240 | 267 | 299 | 300 | 301 | 329 | 331 |

TABLE 10-continued

CORRELATION OF AMINO ACID RESIDUE POSITIONS [#]

| 66/68 | P4 | D31 | N63 | G64 | T65 | A93 | P95 |
|---|---|---|---|---|---|---|---|
| 30 | 240 | 267 | 299 | 300 | 301 | 329 | 331 |
| 32 | 238 | 265 | 297 | 298 | 299 | 327 | 329 |

[#] The correlation of amino acid residue positions of native and substituted cFcs with that of the corresponding substituted canine heavy chains. First Column lists SEQ ID NOs.; remaining columns list corresponding amino acid positions. For the two native amino acid sequences (SEQ ID NOs. 66 and 68), the one letter code for the natural amino acid residues are also provided.

TABLE 11

INDIVIDUAL UNSUBSTITUTED CANINIZED HEAVY AND LIGHT CHAINS

| # | N. | A. | |
|---|---|---|---|
| 33 | ✓ | | 4F9- VH3-CH1-hinge-FC -cIgGA Fc |
| 34 | | ✓ | 4F9- VH3-CH1-hinge-FC -cIgGA Fc |
| 35 | ✓ | | 4F9- VH3-CH1-hinge-FC -cIgGD Fc |
| 36 | | ✓ | 4F9- VH3-CH1-hinge-FC -cIgGD Fc |
| 37 | ✓ | | 4F9- VL3-CL-Kappa |
| 38 | | ✓ | 4F9- VL3-CL-Kappa |
| 39 | ✓ | | 5F12- VH3-CH1-hinge-FC -cIgGA Fc |
| 40 | | ✓ | 5F12- VH3-CH1-hinge-FC -cIgGA Fc |

TABLE 11-continued

INDIVIDUAL UNSUBSTITUTED CANINIZED HEAVY AND LIGHT CHAINS

| # | N. | A. | |
|---|---|---|---|
| 41 | ✓ | | 5F12-VH3-CH1-hinge-FC-cIgGD Fc |
| 42 | | ✓ | 5F12-VH3-CH1-hinge-FC -cIgGD Fc |
| 43 | ✓ | | 5F12-VL3-CL-Kappa |
| 44 | | ✓ | 5F12-VL3-CL-Kappa |

TABLE 12

VARIABLE REGIONS OF HEAVY AND LIGHT CHAINS

| # | N. | A. | Antibody |
|---|---|---|---|
| 73 | ✓ | | 4F9-Heavy |
| 74 | | ✓ | 4F9-Heavy |
| 75 | ✓ | | 4F9-Light |
| 76 | | ✓ | 4F9-Light |
| 77 | ✓ | | 5F12-Heavy |
| 78 | | ✓ | 5F12-Heavy |
| 79 | ✓ | | 5F12-Light |
| 80 | | ✓ | 5F12-Light |

```
Modified Fc
cIgGB Fc
                                                          [SEQ ID NO: 2]
LGGXSVFIFPPKPKDTLLIARTPEVTCVVVXLDPEDPEVQISWFVDGKQMQTAKTQPREEQF

XXXYRVVSVLPIGHQDWLKGKQFTCKVNNKXLXSPIERTISKARGQAHQPSVYVLPPSREEL

SKNTVSLTCLIKDFFPPDIDVEWQSNGQQEPESKYRTTPPQLDEDGSYFLYSKLSVDKSRWQ

RGDTFICAVMHEALHNHYTQESLSHSPGK cIgGB Fc
                                                          [SEQ ID NO: 1]
ctgggcggcnnnagcgtgtttattttccgccgaaaccgaaagatacctgctgattgcgcg caccccggaagtgacctgcgtggtggtgnnnctggatccggaagatccggaagtgcagatta gctggtttgtggatggcaaacagatgcagaccgcgaaaacccagccgcgcgaagaacagttt nnnnnnnnntatcgcgtggtgagcgtgctgccgattggccatcaggattggctgaaaggcaa acagtttacctgcaaagtgaacaacaaannnctgnnnagcccgattgaacgcaccattagca aagcgcgcggccaggcgcatcagccgagcgtgtatgtgctgccgccgagccgcgaagaactg agcaaaaacaccgtgagcctgacctgcctgattaaagatttttttccgccggatattgatgt ggaatggcagagcaacggccagcaggaaccggaaagcaaatatcgcaccaccccgccgcagc tggatgaagatggcagctattttctgtatagcaaactgagcgtggataaaagccgctggcag cgcggcgataccctttatttgcgcggtgatgcatgaagcgctgcataaccattatacccagga aagcctgagccatagcccgggcaaa cIgGC Fc
                                                          [SEQ ID NO: 4]
LGGXSVFIFPPKPKDILVTARTPTVTCVVVXLDPENPEVQISWFVDSKQVQTANTQPREEQS

XXXYRVVSVLPIGHQDWLSGKQFKCKVNNKXLXSPIEEIISKTPGQAHQPNVYVLPPSRDEM

SKNTVTLTCLVKDFFPPEIDVEWQSNGQQEPESKYRMTPPQLDEDGSYFLYSKLSVDKSRWQ

RGDTFICAVMHEALHNHYTQISLSHSPGK
```

-continued cIgGC Fc
[SEQ ID NO: 3]

ctgggcggcnnnagcgtgtttattttccgccgaaaccgaaagatattctggtgaccgcgcg caccccgaccgtgacctgcgtggtggtgnnnctggatccggaaaacccggaagtgcagatta gctggtttgtggatagcaaacaggtgcagaccgcgaacacccagccgcgcgaagaacagagc nnnnnnnnntatcgcgtggtgagcgtgctgccgattggccatcaggattggctgagcggcaa acagtttaaatgcaaagtgaacaacaaannnctgnnnagcccgattgaagaaattattagca aaaccccgggccaggcgcatcagccgaacgtgtatgtgctgccgccgagccgcgatgaaatg agcaaaaacaccgtgaccctgacctgcctggtgaaagattttttttccgccggaaattgatgt ggaatggcagagcaacggccagcaggaaccggaaagcaaatatcgcatgaccccgccgcagc tggatgaagatggcagctattttctgtatagcaaactgagcgtggataaaagccgctggcag cgcggcgatacctttatttgcgcggtgatgcatgaagcgctgcataaccattatcccagat tagcctgagccatagcccgggcaaa cIgGD Fc (S→22P in D hinge) fab arm exchange
[SEQ ID NO: 6]

PKESTCKCIPPCPVPESLGGPSVFIFPPKPKDILRITRTPEITCVVLDLGREDPEVQISWFV

DGKEVHTAKTQPREQQFNSTYRVVSVLPIEHQDWLTGKEFKCRVNHIGLPSPIERTISKARG

QAHQPSVYVLPPSPKELSSSDTVTLTCLIKDFFPPEIDVEWQSNGQPEPESKYHTTAPQLDE

DGSYFLYSKLSVDKSRWQQGDTFTCAVMHEALQNHYTDLSLSHSPGK cIgGD Fc (S→22P in D hinge) fab arm exchange
[SEQ ID NO: 5]

ccgaaagaaagcacctgcaaatgcattccgccgtgcccggtgccggaaagcctgggcggccc gagcgtgtttattttccgccgaaaccgaaagatattctgcgcattacccgcacccggaaa ttacctgcgtggtgctggatctgggccgcgaagatccggaagtgcagattagctggtttgtg gatggcaaagaagtgcataccgcgaaaacccagccgcgcgaacagcagtttaacagcaccta tcgcgtggtgagcgtgctgccgattgaacatcaggattggctgaccggcaaagaatttaaat gccgcgtgaaccatattggcctgccgagcccgattgaacgcaccattagcaaagcgcgcggc caggcgcatcagccgagcgtgtatgtgctgccgccgagcccgaaagaactgagcagcagcga taccgtgaccctgacctgcctgattaaagattttttttccgccggaaattgatgtggaatggc agagcaacggccagccggaaccggaaagcaaatatcataccaccgcgccgcagctggatgaa gatggcagctattttctgtatagcaaactgagcgtggataaaagccgctggcagcagggcga tacctttacctgcgcggtgatgcatgaagcgctgcagaaccattataccgatctgagcctga gccatagcccgggcaaa cIgGD Fc (k hinge) fab arm exchange
[SEQ ID NO: 8]

FNECRCTDTPPCPVPEPLGGPSVFIFPPKPKDILRITRTPEITCVVLDLGREDPEVQISWFV

DGKEVHTAKTQPREQQFNSTYRVVSVLPIEHQDWLTGKEFKCRVNHIGLPSPIERTISKARG

QAHQPSVYVLPPSPKELSSSDTVTLTCLIKDFFPPEIDVEWQSNGQPEPESKYHTTAPQLDE

DGSYFLYSKLSVDKSRWQQGDTFTCAVMHEALQNHYTDLSLSHSPGK cIgGD Fc (k hinge) fab arm exchange
[SEQ ID NO: 7]

tttaacgaatgccgctgcaccgataccccgccgtgcccggtgccggaaccgctgggcggc ccgagcgtgtttattttccgccgaaaccgaaagatattctgcgcattacccgcacccog gaaattacctgcgtggtgctggatctgggccgcgaagatccggaagtgcagattagctgg tttgtggatggcaaagaagtgcataccgcgaaaacccagccgcgcgaacagcagtttaac -continued agcacctatcgcgtggtgagcgtgctgccgattgaacatcaggattggctgaccggcaaa gaatttaaatgccgcgtgaaccatattggcctgccgagcccgattgaacgcaccattagc aaagcgcgcggccaggcgcatcagccgagcgtgtatgtgctgccgccgagcccgaaagaa ctgagcagcagcgataccgtgaccctgacctgcctgattaaagattttttccgccggaa attgatgtggaatggcagagcaacggccagccggaaccggaaagcaaatatcataccacc gcgccgcagctggatgaagatggcagctattttctgtatagcaaactgagcgtggataaa agccgctggcagcagggcgatacctttacctgcgcggtgatgcatgaagcgctgcagaac cattataccgatctgagcctgagccatagcccgggcaaa cIgGD Fc (B hinge) fab arm exchange [SEQ ID NO: 10]

PKRENGRVPRPPDCPKCPAPEMLGGPSVFIFPPKPKDILRITRTPEITCVVLDLGREDPEVQ

ISWFVDGKEVHTAKTQPREQQFNSTYRVVSVLPIEHQDWLTGKEFKCRVNHIGLPSPIERTI

SKARGQAHQPSVYVLPPSPKELSSSDTVTLTCLIKDFFPPEIDVEWQSNGQPEPESKYHTTA

PQLDEDGSYFLYSKLSVDKSRWQQGDTFTCAVMHEALQNHYTDLSLSHSPGK cIgGD Fc (B hinge) fab arm exchange [SEQ ID NO: 9]

ccgaaacgcgaaaacggccgcgtgccgcgcccgccggattgcccgaaatgcccggcgccg gaaatgctgggcggcccgagcgtgtttatttttccgccgaaaccgaaagatattctgcgc attacccgcacccggaaattacctgcgtggtgctggatctgggccgcgaagatccggaa gtgcagattagctggtttgtggatggcaaagaagtgcataccgcgaaaacccagccgcgc gaacagcagtttaacagcacctatcgcgtggtgagcgtgctgccgattgaacatcaggat tggctgaccggcaaagaatttaaatgccgcgtgaaccatattggcctgccgagcccgatt gaacgcaccattagcaaagcgcgcggccaggcgcatcagccgagcgtgtatgtgctgccg ccgagcccgaaagaactgagcagcagcgataccgtgaccctgacctgcctgattaaagat ttttttccgccggaaattgatgtggaatggcagagcaacggccagccggaaccggaaagc aaatatcataccaccgcgccgcagctggatgaagatggcagctattttctgtatagcaaa ctgagcgtggataaaagccgctggcagcagggcgataccttacctgcgcggtgatgcat gaagcgctgcagaaccattataccgatctgagcctgagccatagcccgggcaaa cIgGD Fc (C hinge) fab arm exchange [SEQ ID NO: 12]

AKECECKCNCNNCPCPGCGLLGGPSVFIFPPKPKDILRITRTPEITCVVLDLGREDPEVQIS

WFVDGKEVHTAKTQPREQQFNSTYRVVSVLPIEHQDWLTGKEFKCRVNHIGLPSPIERTISK

ARGQAHQPSVYVLPPSPKELSSSDTVTLTCLIKDFFPPEIDVEWQSNGQPEPESKYHTTAPQ

LDEDGSYFLYSKLSVDKSRWQQGDTFTCAVMHEALQNHYTDLSLSHSPGK cIgGD Fc (C hinge) fab arm exchange [SEQ ID NO: 11]

gccaaggagtgcgagtgcaagtgcaactgcaacaactgcccctgccccggctgcggcctg ctgggcggccccagcgtgttcatcttcccccccaagcccaaggacatcctgagaatcacc agaaccccccgagatcacctgcgtggtgctggacctgggcagagaggaccccgaggtgcag atcagctggttcgtggacggcaaggaggtgcacaccgccaagacccagcccagagagcag cagttcaacagcacctacagagtggtgagcgtgctgcccatcgagcaccaggactggctg accggcaaggagttcaagtgcagagtgaaccacatcggcctgcccagccccatcgagaga accatcagcaaggccagaggccaggcccaccagcccagcgtgtacgtgctgccccccagc cccaaggagctgagcagcagcgacaccgtgaccctgacctgcctgatcaaggacttcttc cccccgagatcgacgtggagtggcagagcaacggccagcccgagcccgagagcaagtac

```
cacaccaccgccccccagctggacgaggacggcagctacttcctgtacagcaagctgagc gtggacaagagcagatggcagcagggcgacaccttcacctgcgccgtgatgcacgaggcc ctgcagaaccactacaccgacctgagcctgagccacagccccggcaag
```

```
Native Fc
cIgGA Fc                                                            [SEQ ID NO: 62]
LGGPSVLIFPPKPKDILRITRTPEVTCVVLDLGREDPEVQISWFVDGKEVHTAKTQSREQQF

NGTYRVVSVLPIEHQDWLTGKEFKCRVNHIDLPSPIERTISKARGRAHKPSVYVLPPSPKEL

SSSDTVSITCLIKDFYPPDIDVEWQSNGQQEPERKHRMTPPQLDEDGSYFLYSKLSVDKSRW

QQGDPFTCAVMHETLQNHYTDLSLSHSPGK cIgGA Fc                                                            [SEQ ID NO: 61]
ctgggcggccccagcgtgctgatcttccccccaagcccaaggacatcctgagaatcacc agaaccccgaggtgacctgcgtggtgctggacctgggcagagaggaccccgaggtgcag atcagctggttcgtggacggcaaggaggtgcacaccgccaagacccagagcagagagcag cagttcaacggcacctacagagtggtgagcgtgctgcccatcgagcaccaggactggctg accggcaaggagttcaagtgcagagtgaaccacatcgacctgccagcccccatcgagaga accatcagcaaggccagaggcagagcccacaagcccagcgtgtacgtgctgcccccagc cccaaggagctgagcagcagcgacaccgtgagcatcacctgcctgatcaaggacttctac cccccgacatcgacgtggagtggcagagcaacggccagcaggagcccgagagaaagcac agaatgacccccccagctggacgaggacggcagctacttcctgtacagcaagctgagc gtggacaagagcagatggcagcagggcgaccccttcacctgcgccgtgatgcacgagacc ctgcagaaccactacaccgacctgagcctgagccacagccccggcaag cIgGD Fc                                                            [SEQ ID NO: 64]
LGGPSVFIFPPKPKDILRITRTPEITCVVLDLGREDPEVQISWFVDGKEVHTAKTQPREQQF

NSTYRVVSVLPIEHQDWLTGKEFKCRVNHIGLPSPIERTISKARGQAHQPSVYVLPPSPKEL

SSSDTVTLTCLIKDFFPPEIDVEWQSNGQPEPESKYHTTAPQLDEDGSYFLYSKLSVDKSRW

QQGDTFTCAVMHEALQNHYTDLSLSHSPGK cIgGD Fc                                                            [SEQ ID NO: 63]
ctgggcggccccagcgtgttcatcttccccccaagcccaaggacatcctgagaatcacc agaaccccgagatcacctgcgtggtgctggacctgggcagagaggaccccgaggtgcag atcagctggttcgtggacggcaaggaggtgcacaccgccaagacccagcccagagagcag cagttcaacagcacctacagagtggtgagcgtgctgcccatcgagcaccaggactggctg accggcaaggagttcaagtgcagagtgaaccacatcggcctgccagcccccatcgagaga accatcagcaaggccagaggccaggcccaccagcccagcgtgtacgtgctgcccccagc cccaaggagctgagcagcagcgacaccgtgaccctgacctgcctgatcaaggacttcttc cccccgagatcgacgtggagtggcagagcaacggccagcccgagcccgagagcaagtac cacaccaccgccccccagctggacgaggacggcagctacttcctgtacagcaagctgagc gtggacaagagcagatggcagcagggcgacaccttcacctgcgccgtgatgcacgaggcc ctgcagaaccactacaccgacctgagcctgagccacagccccggcaag
```

```
cIgGB Fc
                                                                    [SEQ ID NO: 66]
LGGPSVFIFPPKPKDTLLIARTPEVTCVVVDLDPEDPEVQISWFVDGKQMQTAKTQPREEQFNGTYRVVSVL

PIGHQDWLKGKQFTCKVNNKALPSPIERTISKARGQAHQPSVYVLPPSREELSKNTVSLTCLIKDFFPPDID

VEWQSNGQQEPESKYRTTPPQLDEDGSYFLYSKLSVDKSRWQRGDTFICAVMHEALHNHYTQESLSHSPGK cIgGB Fc
                                                                    [SEQ ID NO: 65]
ctgggcggccccagcgtgttcatcttccccccaagcccaaggacaccctgctgatcgcc agaaccccgaggtgacctgcgtggtggtggacctggaccccgaggaccccgaggtgcag atcagctggttcgtggacggcaagcagatgcagaccgccaagacccagcccagagaggag cagttcaacggcacctacagagtggtgagcgtgctgcccatcggccaccaggactggctg aagggcaagcagttcacctgcaaggtgaacaacaaggccctgcccagccccatcgagaga accatcagcaaggccagaggccaggcccaccagcccagcgtgtacgtgctgccccccagc agagaggagctgagcaagaacaccgtgagcctgacctgcctgatcaaggacttcttcccc cccgacatcgacgtggagtggcagagcaacggccagcaggagcccgagagcaagtacaga accacccccccagctggacgaggacggcagctacttcctgtacagcaagctgagcgtg gacaagagcagatggcagagaggcgacaccttcatctgcgccgtgatgcacgaggccctg cacaaccactacacccaggagagcctgagccacagccccggcaag cIgGC Fc
                                                                    [SEQ ID NO: 68]
LGGPSVFIFPPKPKDILVTARTPTVTCVVVDLDPENPEVQISWFVDSKQVQTANTQPREEQS

NGTYRVVSVLPIGHQDWLSGKQFKCKVNNKALPSPIEEIISKTPGQAHQPNVYVLPPSRDEM

SKNTVTLTCLVKDFFPPEIDVEWQSNGQQEPESKYRMTPPQLDEDGSYFLYSKLSVDKSRWQ

RGDTFICAVMHEALHNHYTQISLSHSPGK cIgGC Fc
                                                                    [SEQ ID NO: 67]
ctgggcggccccagcgtgttcatcttccccccaagcccaaggacatcctggtgaccgcc agaaccccaccgtgacctgcgtggtggtggacctggaccccgagaaccccgaggtgcag atcagctggttcgtggacagcaagcaggtgcagaccgccaacacccagcccagagaggag cagagcaacggcacctacagagtggtgagcgtgctgcccatcggccaccaggactggctg agcggcaagcagttcaagtgcaaggtgaacaacaaggccctgcccagccccatcgaggag atcatcagcaagacccccggccaggcccaccagcccaacgtgtacgtgctgccccccagc agagacgagatgagcaagaacaccgtgaccctgacctgcctggtgaaggacttcttcccc cccgagatcgacgtggagtggcagagcaacggccagcaggagcccgagagcaagtacaga atgaccccccccagctggacgaggacggcagctacttcctgtacagcaagctgagcgtg gacaagagcagatggcagagaggcgacaccttcatctgcgccgtgatgcacgaggccctg cacaaccactacacccagatcagcctgagccacagccccggcaag Individual substituted heavy chains
4F9-VH3 cIgGB
                                                                    [SEQ ID NO: 26]
EVQLVQSGGDLVKPGGSVRLSCVASGFTFSYAMSWVRQAPGKGLQWMGTISDGGSYTHYPDN

LMGRFTFSLDTAKNTAYLQLNSLRAEDTAVYYCARESYDGYYVANWGQGTLVTVSSASTTAP

SVFPLAPSCGSTSGSTVALACLVSGYFPEPVTVSWNSGSLTSGVHTFPSVLQSSGLYSLSSM

VTVPSSRWPSETFTCNVAHPASKTKVDKPVPKRENGRVPRPPDCPKCPAPEMLGGXSVFIFP

PKPKDTLLIARTPEVTCVVVXLDPEDPEVQISWFVDGKQMQTAKTQPREEQFXXXYRVVSVL

PIGHQDWLKGKQFTCKVNNKXLXSPIERTISKARGQAHQPSVYVLPPSREELSKNTVSLTCL
```

IKDFFPPDIDVEWQSNGQQEPESKYRTTPPQLDEDGSYFLYSKLSVDKSRWQRGDTFICAVM

HEALHNHYTQESLSHSPGK

4F9-VH3 cIgGB DNA [SEQ ID NO: 25]

gaggtgcagctggtgcagagcggcggcgacctggtgaagcccggcggcagcgtgagactgag ctgcgtggccagcggcttcaccttcagctacgccatgagctgggtgagacaggcccccggca agggcctgcagtggatgggcaccatcagcgacggcggcagctacacccactaccccgacaac ctgatgggcagattcaccttcagcctggacaccgccaagaacaccgcctacctgcagctgaa cagcctgagagccgaggacaccgccgtgtactactgcgccagagagagctacgacggctact acgtggccaactggggccagggcaccctggtgaccgtgagcagcgccagcaccaccgccccc agcgtgttccccctggcccccagctgcggcagcaccagcggcagcaccgtggccctggcctg cctggtgagcggctacttccccgagcccgtgaccgtgagctggaacagcggcagcctgacca gcggcgtgcacaccttccccagcgtgctgcagagcagcggcctgtacagcctgagcagcatg gtgaccgtgcccagcagcagatggcccagcgagaccttcacctgcaacgtggcccaccccgc cagcaagaccaaggtggacaagcccgtgcccaagagagaaacggcagagtgcccagacccc ccgactgccccaagtgccccgcccccgagatgctgggcggcnnnagcgtgttcatcttcccc cccaagcccaaggacaccctgctgatcgccagaaccccgaggtgacctgcgtggtggtgnn nctggaccccgaggaccccgaggtgcagatcagctggttcgtggacggcaagcagatgcaga ccgccaagacccagcccagagaggagcagttcnnnnnnnnnntacagagtggtgagcgtgctg cccatcggccaccaggactggctgaagggcaagcagttcacctgcaaggtgaacaacaagnn nctgnnnagccccatcgagagaaccatcagcaaggccagaggccaggccaccagcccagcg tgtacgtgctgcccccagcagagaggagctgagcaagaacaccgtgagcctgacctgcctg atcaaggacttcttccccccgacatcgacgtggagtggcagagcaacggccagcaggagcc cgagagcaagtacagaaccacccccccagctggacgaggacggcagctacttcctgtaca gcaagctgagcgtggacaagagcagatggcagagaggcgacaccttcatctgcgccgtgatg cacgaggccctgcacaaccactacacccaggagagcctgagccacagccccggcaag 4F9-VH3 cIgGC [SEQ ID NO: 28]

EVQLVQSGGDLVKPGGSVRLSCVASGFTFSYAMSWVRQAPGKGLQWMGTISDGGSYTHYPDN

LMGRFTFSLDTAKNTAYLQLNSLRAEDTAVYYCARESYDGYYVANWGQGTLVTVSSASTTAP

SVFPLAPSCGSQSGSTVALACLVSGYIPEPVTVSWNSVSLTSGVHTFPSVLQSSGLYSLSSM

VTVPSSRWPSETFTCNVAHPATNTKVDKPVAKECECKCNCNNCPCPGCGLLGGXSVFIFPPK

PKDILVTARTPTVTCVVVXLDPENPEVQISWFVDSKQVQTANTQPREEQSXXXYRVVSVLPI

GHQDWLSGKQFKCKVNNKXLXSPIEEIISKTPGQAHQPNVYVLPPSRDEMSKNTVTLTCLVK

DFFPPEIDVEWQSNGQQEPESKYRMTPPQLDEDGSYFLYSKLSVDKSRWQRGDTFICAVMHE

ALHNHYTQISLSHSPGK

4F9-VH3 cIgGC DNA [SEQ ID NO: 27]

gaggtgcagctggtgcagagcggcggcgacctggtgaagcccggcggcagcgtgagactgag ctgcgtggccagcggcttcaccttcagctacgccatgagctgggtgagacaggcccccggca agggcctgcagtggatgggcaccatcagcgacggcggcagctacacccactaccccgacaac ctgatgggcagattcaccttcagcctggacaccgccaagaacaccgcctacctgcagctgaa cagcctgagagccgaggacaccgccgtgtactactgcgccagagagagctacgacggctact -continued
```
acgtggccaactggggccagggcaccctggtgaccgtgagcagcgccagcaccaccgccccc agcgtgttccccctggcccccagctgcggcagccagagcggcagcaccgtggccctggcctg cctggtgagcggctacatccccgagcccgtgaccgtgagctggaacagcgtgagcctgacca gcggcgtgcacaccttccccagcgtgctgcagagcagcggcctgtacagcctgagcagcatg gtgaccgtgcccagcagcagatggcccagcgagaccttcacctgcaacgtggcccaccccgc caccaacaccaaggtggacaagcccgtggccaaggagtgcgagtgcaagtgcaactgcaaca actgccccctgccccggctgcggcctgctgggcggcnnnagcgtgttcatcttccccccaag cccaaggacatcctggtgaccgccagaaccccaccgtgacctgcgtggtggtgnnnctgga ccccgagaaccccgaggtgcagatcagctggttcgtggacagcaagcaggtgcagaccgcca acacccagcccagagaggagcagagcnnnnnnnnnntacagagtggtgagcgtgctgcccatc ggccaccaggactggctgagcggcaagcagttcaagtgcaaggtgaacaacaagnnnctgnn nagccccatcgaggagatcatcagcaagaccccggccaggccaccagcccaacgtgtacg tgctgccccccagcagagacgagatgagcaagaacaccgtgaccctgacctgcctggtgaag gacttcttccccccgagatcgacgtggagtggcagagcaacggccagcaggagcccgagag caagtacagaatgaccccccccagctggacgaggacggcagctacttcctgtacagcaagc tgagcgtggacaagagcagatggcagagaggcgacaccttcatctgcgccgtgatgcacgag gccctgcacaaccactacacccagatcagcctgagccacagccccggcaag
```

5F12-VH3 CIgGB [SEQ ID NO: 30]
```
EVQLVQSGGDLVKPGGSVRLSCVASFTFDYYMNWVRQAPGKGLQWIGRWIFPGSGATYYNER

FMGKATISADTAKNTAYMQLNSLRAEDTAVYYCLRSDWDVGDFWGQGTLVTVSSASTTAPSV

FPLAPSCGSTSGSTVALACLVSGYFPEPVTVSWNSGSLTSGVHTFPSVLQSSGLYSLSSMVT

VPSSRWPSETFTCNVAHPASKTKVDKPVPKRENGRVPRPPDCPKCPAPEMLGGXSVFIFPPK

PKDTLLIARTPEVTCVVVXLDPEDPEVQISWFVDGKQMQTAKTQPREEQFXXXYRVVSVLPI

GHQDWLKGKQFTCKVNNKXLXSPIERTISKARGQAHQPSVYVLPPSREELSKNTVSLTCLIK

DFFPPDIDVEWQSNGQQEPESKYRTTPPQLDEDGSYFLYSKLSVDKSRWQRGDTFICAVMHE

ALHNHYTQESLSHSPGK
```

5F12-VE3 CIgGB DNA [SEQ ID NO: 29]
```
gaggtgcagctggtgcagagcggcggcgacctggtgaagcccggcggcagcgtgagactgag ctgcgtggccagcttcaccttcgactactacatgaactgggagacaggccccggcaagg gcctgcagtggatcggcagatggatcttccccggcagcggcgccacctactacaacgagaga ttcatgggcaaggccaccatcagcgccgacaccgccaagaacaccgcctacatgcagctgaa cagcctgagagccgaggacaccgccgtgtactactgcctgagaagcgactgggacgtgggcg acttctggggccagggcaccctggtgaccgtgagcagcgccagcaccaccgcccccagcgtg ttccccctggcccccagctgcggcagccagagcggcagcaccgtggccctggcctgcctggt gagcggctacttccccgagcccgtgaccgtgagctggaacagcggcagcctgaccagcggcg tgcacaccttccccagcgtgctgcagagcagcggcctgtacagcctgagcagcatggtgacc gtgcccagcagcagatggcccagcgagaccttcacctgcaacgtggcccaccccgccagcaa gaccaaggtggacaagcccgtgcccaagagagagaacggcagagtgcccagacccccgact gccccaagtgccccgccccgagatgctgggcggcnnnagcgtgttcatcttccccccaag cccaaggacaccctgctgatcgccagaaccccgaggtgacctgcgtggtggtgnnnctgga ccccgaggaccccgaggtgcagatcagctggttcgtggacggcaagcagatgcagaccgcca
``` agacccagcccagagaggagcagttcnnnnnnnnntacagagtggtgagcgtgctgcccatc ggccaccaggactggctgaagggcaagcagttcacctgcaaggtgaacaacaagnnnctgnn nagcccatcgagagaaccatcagcaaggccagaggccaggccaccagcccagcgtgtacg tgctgcccccagcagagaggagctgagcaagaacaccgtgagcctgacctgcctgatcaag gacttcttcccccccgacatcgacgtggagtggcagagcaacggccagcaggagcccgagag caagtacagaaccacccccccccagctggacgaggacggcagctacttcctgtacagcaagc tgagcgtggacaagagcagatggcagagaggcgacaccttcatctgcgccgtgatgcacgag gccctgcacaaccactacacccaggagagcctgagccacagccccggcaag 5F12-VH3-cIgGC Fc [SEQ ID NO: 32]

EVQLVQSGGDLVKPGGSVRLSCVASFTFDYYMNWVRQAPGKGLQWIGRWIFPGSGATYYNER

FMGKATISADTAKNTAYMQLNSLRAEDTAVYYCLRSDWDVGDFWGQGTLVTVSSASTTAPSV

FPLAPSCGSQSGSTVALACLVSGYIPEPVTVSWNSVSLTSGVHTFPSVLQSSGLYSLSSMVT

VPSSRWPSETFTCNVAHPATNTKVDKPVAKECECKCNCNNCPCPGCGLLGGXSVFIFPPKPK

DILVTARTPTVTCVVVXLDPENPEVQISWFVDSKQVQTANTQPREEQSXXXYRVVSVLPIGH

QDWLSGKQFKCKVNNKXLXSPIEEIISKTPGQAHQPNVYVLPPSRDEMSKNTVTLTCLVKDF

FPPEIDVEWQSNGQQEPESKYRMTPPQLDEDGSYFLYSKLSVDKSRWQRGDTFICAVMHEAL

HNHYTQISLSHSPGK

5F12-VH3-cIgGC Fc DNA [SEQ ID NO: 31]

gaggtgcagctggtgcagagcggcggcgacctggtgaagcccggcggcagcgtgagactgag ctgcgtggccagcttcaccttcgactactacatgaactgggtgagacaggcccccggcaagg gcctgcagtggatcggcagatggatcttccccggcagcggcgccacctactacaacgagaga ttcatgggcaaggccaccatcagcgccgacaccgccaagaacaccgcctacatgcagctgaa cagcctgagagccgaggacaccgccgtgtactactgcctgagaagcgactgggacgtgggcg acttctggggccagggcaccctggtgaccgtgagcagcgccagcaccaccgcccccagcgtg ttcccccctggccccagctgcggcagccagagcggcagcaccgtggccctggcctgcctggt gagcggctacatccccgagcccgtgaccgtgagctggaacagcgtgagcctgaccagcggcg tgcacaccttccccagcgtgctgcagagcagcggcctgtacagcctgagcagcatggtgacc gtgcccagcagcagatggcccagcgagaccttcacctgcaacgtggcccaccccgccaccaa caccaaggtggacaagcccgtggccaaggagtgcgagtgcaagtgcaactgcaacaactgcc cctgccccggctgcggcctgctgggcggcnnnagcgtgttcatcttccccccaagcccaag gacatcctggtgaccgccagaacccccaccgtgacctgcgtggtggtgnnnctggaccccga gaaccccgaggtgcagatcagctggttcgtggacagcaagcaggtgcagaccgccaacaccc agcccagagaggagcagagcnnnnnnnnntacagagtggtgagcgtgctgcccatcggccac caggactggctgagcggcaagcagttcaagtgcaaggtgaacaacaagnnnctgnnnagccc catcgaggagatcatcagcaagacccccggccaggccaccagcccaacgtgtacgtgctgc ccccagcagagacgagatgagcaagaacaccgtgaccctgacctgcctggtgaaggacttc ttccccccgagatcgacgtggagtggcagagcaacggccagcaggagcccgagagcaagta cagaatgaccccccccagctggacgaggacggcagctacttcctgtacagcaagctgagcg tggacaagagcagatggcagagaggcgacaccttcatctgcgccgtgatgcacgaggccctg cacaaccactacacccagatcagcctgagccacagccccggcaag -continued Individual un-substituted caninized heavy and light chains
4F9-VH3-cIgGA Fc

[SEQ ID NO: 34]

EVQLVQSGGDLVKPGGSVRLSCVASGFTFSYAMSWVRQAPGKGLQWMGTISDGGSYTHYPDN

LMGRFTFSLDTAKNTAYLQLNSLRAEDTAVYYCARESYDGYYVANWGQGTLVTVSSASTTAP

SVFPLAPSCGSTSGSTVALACLVSGYFPEPVTVSWNSGSLTSGVHTFPSVLQSSGLHSLSSM

VTVPSSRWPSETFTCNVVHPASNTKVDKPVFNECRCTDTPPCPVPEPLGGPSVLIFPPKPKD

ILRITRTPEVTCVVLDLGREDPEVQISWFVDGKEVHTAKTQSREQQFNGTYRVVSVLPIEHQ

DWLTGKEFKCRVNHIDLPSPIERTISKARGRAHKPSVYVLPPSPKELSSSDTVSITCLIKDF

YPPDIDVEWQSNGQQEPERKHRMTPPQLDEDGSYFLYSKLSVDKSRWQQGDPFTCAVMHETL

QNHYTDLSLSHSPGK

4F9-VH3-cIgGA Fc

[SEQ ID NO: 33]

gaggtgcagctggtgcagagcggcggcgacctggtgaagcccggcggcagcgtgagactg agctgcgtggccagcggcttcaccttcagctacgccatgagctgggtgagacaggccccc ggcaagggcctgcagtggatgggcaccatcagcgacggcggcagctacacccactacccc gacaacctgatgggcagattcaccttcagcctggacaccgccaagaacaccgcctacctg cagctgaacagcctgagagccgaggacaccgccgtgtactactgcgccagagagagctac gacggctactacgtggccaactggggccagggcaccctggtgaccgtgagcagcgccagc accaccgccccagcgtgttcccctggccccagctgcggcagcaccagcggcagcacc gtggccctggcctgctggtgagcggctacttccccgagcccgtgaccgtgagctggaac agcggcagcctgaccagcggcgtgcacaccttccccagcgtgctgcagagcagcggcctg cacagcctgagcagcatggtgaccgtgcccagcagcagatggcccagcgagaccttcacc tgcaacgtggtgcaccccgccagcaacaccaaggtggacaagcccgtgttcaacgagtgc agatgcaccgacacccccccctgccccgtgcccgagcccctgggcggccccagcgtgctg atcttcccccccaagccccaaggacatcctgagaatcaccagaaccccgaggtgacctgc gtggtgctggacctgggcagagaggaccccgaggtgcagatcagctggttcgtggacggc aaggaggtgcacaccgccaagacccagagcagagagcagcagttcaacggcacctacaga gtggtgagcgtgctgcccatcgagcaccaggactggctgaccggcaaggagttcaagtgc agagtgaaccacatcgacctgcccagccccatcgagagaaccatcagcaaggccagaggc agagcccacaagcccagcgtgtacgtgctgccccccagccccaaggagctgagcagcagc gacaccgtgagcatcacctgcctgatcaaggacttctacccccccgacatcgacgtggag tggcagagcaacggccagcaggagcccgagagaaagcacagaatgacccccccccagctg gacgaggacggcagctacttcctgtacagcaagctgagcgtggacaagagcagatggcag cagggcgaccccttcacctgcgccgtgatgcacgagaccctgcagaaccactacaccgac ctgagcctgagccacagcccccggcaag 4F9-VH3 cIgGD Fc

[SEQ ID NO: 36]

EVQLVQSGGDLVKPGGSVRLSCVASGFTFSYAMSWVRQAPGKGLQWMGTISDGGSYTHYPDN

LMGRFTFSLDTAKNTAYLQLNSLRAEDTAVYYCARESYDGYYVANWGQGTLVTVSSASTTAP

SVFPLAPSCGSTSGSTVALACLVSGYFPEPVTVSWNSGSLTSGVHTFPSVLQSSGLYSLSST

VTVPSSRWPSETFTCNVVHPASNTKVDKPVPKESTCKCISPCPVPESLGGPSVFIFPPKPKD

ILRITRTPEITCVVLDLGREDPEVQISWFVDGKEVHTAKTQPREQQFNSTYRVVSVLPIEHQ

DWLTGKEFKCRVNHIGLPSPIERTISKARGQAHQPSVYVLPPSPKELSSSDTVTLTCLIKDF

FPPEIDVEWQSNGQPEPESKYHTTAPQLDEDGSYFLYSKLSVDKSRWQQGDTFTCAVMHEAL

QNHYTDLSLSHSPGK

4F9-VH3 cIgGD Fc

[SEQ ID NO: 35]

gaggtgcagctggtgcagagcggcggcgacctggtgaagcccggcggcagcgtgagactg agctgcgtggccagcggcttcaccttcagctacgccatgagctgggtgagacaggccccc ggcaagggcctgcagtggatgggcaccatcagcgacggcggcagctacacccactacccc gacaacctgatgggcagattcaccttcagcctggacaccgccaagaacaccgcctacctg cagctgaacagcctgagagccgaggacaccgccgtgtactactgcgccagagagagctac gacggctactacgtggccaactggggccagggcaccctggtgaccgtgagcagcgccagc accaccgccccagcgtgttcccctggccccagctgcggcagcaccagcggcagcacc gtggccctggcctgcctggtgagcggctacttccccgagcccgtgaccgtgagctggaac agcggcagcctgaccagcggcgtgcacaccttccccagcgtgctgcagagcagcggcctg tacagcctgagcagcaccgtgaccgtgcccagcagcagatggcccagcgagaccttcacc tgcaacgtggtgcaccccgccagcaacaccaaggtggacaagcccgtgcccaaggagagc acctgcaagtgcatcagcccctgccccgtgcccgagagcctgggcggccccagcgtgttc atcttcccccccaagcccaaggacatcctgagaatcaccagaaccccgagatcacctgc gtggtgctggacctgggcagagaggaccccgaggtgcagatcagctggttcgtggacggc aaggaggtgcacaccgccaagacccagcccagagagcagcagttcaacagcacctacaga gtggtgagcgtgctgcccatcgagcaccaggactggctgaccggcaaggagttcaagtgc agagtgaaccacatcggcctgcccagccccatcgagagaaccatcagcaaggccagaggc caggccaccagcccagcgtgtacgtgctgcccccagccccaaggagctgagcagcagc gacaccgtgaccctgacctgcctgatcaaggacttcttcccccccgagatcgacgtggag tggcagagcaacggccagcccgagcccgagagcaagtaccacaccaccgcccccagctg gacgaggacggcagctacttcctgtacagcaagctgagcgtggacaagagcagatggcag cagggcgacaccttcacctgcgccgtgatgcacgaggccctgcagaaccactacaccgac ctgagcctgagccacagccccggcaag 4F9-VL3-cL-Kappa

[SEQ ID NO: 38]

DIVMTQTPLSLSVSPGEPASMSCRASQSISNNLHWYRQKPGQSPQVLVKYASQSISGVPDRF

IGSGSGTDFTLRISRVEADDLGVYYCQQSNSWPQTFGQGTKLELKRNDAQPAVYLFQPSPDQ

LHTGSASVVCLLNSFYPKDINVKWKVDGVIQDTGIQESVTEQDSKDSTYSLSSTLTMSSTEY

LSHELYSCEITHKSLPSTLIKSFQRSECQRVD

4F9-VL3-cL-Kappa

[SEQ ID NO: 37]

gacatcgtgatgacccagacccccctgagcctgagcgtgagccccggcgagcccgccagc atgagctgcagagccagccagagcatcagcaacaacctgcactggtacagacagaagccc ggccagagcccccaggtgctggtgaagtacgccagccagagcatcagcggcgtgcccgac agattcatcggcagcggcagcggcaccgacttcaccctgagaatcagcagagtggaggcc gacgacctgggcgtgtactactgccagcagagcaacagctggccccagaccttcggccag ggcaccaagctggagctgaagagaaacgacgcccagcccgccgtgtacctgttccagccc agccccgaccagctgcacaccggcagcgccagcgtggtgtgcctgctgaacagcttctac cccaaggacatcaacgtgaagtggaaggtggacggcgtgatccaggacaccggcatccag gagagcgtgaccgagcaggacagcaaggacagcacctacagcctgagcagcaccctgacc

```
atgagcagcaccgagtacctgagccacgagctgtacagctgcgagatcacccacaagagc
ctgcccagcaccctgatcaagagcttccagagaagcgagtgccagagagtggac
```

5F12-VH3-cIgGA Fc  [SEQ ID NO: 40]

```
EVQLVQSGGDLVKPGGSVRLSCVASFTFDYYMNWVRQAPGKGLQWIGRWIFPGSGATYYNER
FMGKATISADTAKNTAYMQLNSLRAEDTAVYYCLRSDWDVGDFWGQGTLVTVSSASTTAPSV
FPLAPSCGSTSGSTVALACLVSGYFPEPVTVSWNSGSLTSGVHTFPSVLQSSGLHSLSSMVT
VPSSRWPSETFTCNVVHPASNTKVDKPVFNECRCTDTPPCPVPEPLGGPSVLIFPPKPKDIL
RITRTPEVTCVVLDLGREDPEVQISWFVDGKEVHTAKTQSREQQFNGTYRVVSVLPIEHQDW
LTGKEFKCRVNHIDLPSPIERTISKARGRAHKPSVYVLPPSPKELSSSDTVSITCLIKDFYP
PDIDVEWQSNGQQEPERKHRMTPPQLDEDGSYFLYSKLSVDKSRWQQGDPFTCAVMHETLQN
HYTDLSLSHSPGK
```

5F12-VH3-cIgGA Fc  [SEQ ID NO: 39]

```
gaggtgcagctggtgcagagcggcggcgacctggtgaagcccggcggcagcgtgagactg
agctgcgtggccagcttcaccttcgactactacatgaactgggtgagacaggcccccggc
aagggcctgcagtggatcggcagatggatcttccccggcagcggcgccacctactacaac
gagagattcatgggcaaggccaccatcagcgccgacaccgccaagaacaccgcctacatg
cagctgaacagcctgagagccgaggacaccgccgtgtactactgcctgagaagcgactgg
gacgtgggcgacttctggggccagggcaccctggtgaccgtgagcagcgccagcaccacc
gcccccagcgtgttcccctggccccagctgcggcagcaccagcggcagcaccgtggcc
ctggcctgcctggtgagcggctacttccccgagcccgtgaccgtgagctggaacagcggc
agcctgaccagcggcgtgcacaccttccccagcgtgctgcagagcagcggcctgcacagc
ctgagcagcatggtgaccgtgcccagcagcagatggcccagcgagaccttcacctgcaac
gtggtgcaccccgccagcaacaccaaggtggacaagcccgtgttcaacgagtgcagatgc
accgacacccccccctgccccgtgcccgagccctgggcggcccccagcgtgctgatcttc
ccccccaagcccaaggacatcctgagaatcaccagaaccccccgaggtgacctgcgtggtg
ctggacctgggcagagaggaccccgaggtgcagatcagctggttcgtggacggcaaggag
gtgcacaccgccaagacccagagcagagagcagcagttcaacggcacctacagagtggtg
agcgtgctgcccatcgagcaccaggactggctgaccggcaaggagttcaagtgcagagtg
aaccacatcgacctgcccagccccatcgagagaaccatcagcaaggccagaggcagagcc
cacaagcccagcgtgtacgtgctgccccccagccccaaggagctgagcagcagcgacacc
gtgagcatcacctgcctgatcaaggacttctacccccccgacatcgacgtggagtggcag
agcaacggccagcaggagcccgagagaaagcacagaatgacccccccccagctggacgag
gacggcagctacttcctgtacagcaagctgagcgtggacaagagcagatggcagcagggc
gaccccttcacctgcgccgtgatgcacgagaccctgcagaaccactacaccgacctgagc
ctgagccacagcccccggcaag
```

5F12-VH3-cIgGD Fc  [SEQ ID NO: 42]

```
EVQLVQSGGDLVKPGGSVRLSCVASFTFDYYMNWVRQAPGKGLQWIGRWIFPGSGATYYNER
FMGKATISADTAKNTAYMQLNSLRAEDTAVYYCLRSDWDVGDFWGQGTLVTVSSASTTAPSV
FPLAPSCGSTSGSTVALACLVSGYFPEPVTVSWNSGSLTSGVHTFPSVLQSSGLYSLSSTVT
VPSSRWPSETFTCNVVHPASNTKVDKPVPKESTCKCISPCPVPESLGGPSVFIFPPKPKDIL
```

-continued

RITRTPEITCVVLDLGREDPEVQISWFVDGKEVHTAKTQPREQQFNSTYRVVSVLPIEHQDW

LTGKEFKCRVNHIGLPSPIERTISKARGQAHQPSVYVLPPSPKELSSSDTVTLTCLIKDFFP

PEIDVEWQSNGQPEPESKYHTTAPQLDEDGSYFLYSKLSVDKSRWQQGDTFTCAVMHEALQN

HYTDLSLSHSPGK

5F12-VH3-cIgGD Fc [SEQ ID NO: 41]

gaggtgcagctggtgcagagcggcggcgacctggtgaagcccggcggcagcgtgagactg agctgcgtggccagcttcaccttcgactactacatgaactgggtgagacaggccccggc aagggcctgcagtggatcggcagatggatcttccccggcagcggcgccacctactacaac gagagattcatgggcaaggccaccatcagcgccgacaccgccaagaacaccgcctacatg cagctgaacagcctgagagccgaggacaccgccgtgtactactgcctgagaagcgactgg gacgtgggcgacttctggggccagggcaccctggtgaccgtgagcagcgccagcaccacc gcccccagcgtgttccccctggcccccagctgcggcagcaccagcggcagcaccgtggcc ctggcctgcctggtgagcggctacttccccgagcccgtgaccgtgagctggaacagcggc agcctgaccagcggcgtgcacaccttccccagcgtgctgcagagcagcggcctgtacagc ctgagcagcaccgtgaccgtgcccagcagcagatggcccagcgagaccttcacctgcaac gtggtgcaccccgccagcaacaccaaggtggacaagcccgtgcccaaggagagcacctgc aagtgcatcagccctgccccgtgcccgagcctgggcggccccagcgtgttcatcttc ccccccaagcccaaggacatcctgagaatcaccagaaccccgagatcacctgcgtggtg ctggacctgggcagagaggaccccgaggtgcagatcagctggttcgtggacggcaaggag gtgcacaccgccaagacccagcccagagagcagcagttcaacagcacctacagagtggtg agcgtgctgcccatcgagcaccaggactggctgaccggcaaggagttcaagtgcagagtg aaccacatcggcctgcccagccccatcgagagaaccatcagcaaggccagaggccaggcc caccagcccagcgtgtacgtgctgccccccagccccaaggagctgagcagcagcgacacc gtgaccctgacctgcctgatcaaggacttcttccccccgagatcgacgtggagtggcag agcaacggccagcccgagcccgagagcaagtaccacaccaccgccccccagctggacgag gacggcagctacttcctgtacagcaagctgagcgtggacaagagcagatggcagcagggc gacaccttcacctgcgccgtgatgcacgaggccctgcagaaccactacaccgacctgagc ctgagccacagccccggcaag 5F12-VL3-cLKappa [SEQ ID NO: 44]

DIVMTQTPLSLSVSLGEPASISCRSSRSLLHTNGITYLSWYRQKPGQIPQLLIYQMSNLASG

VPDRFSGSGSGTDFTLRISRVEADDAGVYYCAQTLGLPRTFGQGTKVEIKRNDAQPAVYLFQ

PSPDQLHTGSASVVCLLNSFYPKDINVKWKVDGVIQDTGIQESVTEQDSKDSTYSLSSTLTM

SSTEYLSHELYSCEITHKSLPSTLIKSFQRSECQRVD

5F12-VL3-cLKappa [SEQ ID NO: 43]

gacatcgtgatgacccagaccccctgagcctgagcgtgagcctgggcgagcccgccagc atcagctgcagaagcagcagaagcctgctgcacaccaacggcatcacctacctgagctgg tacagacagaagcccggccagatcccccagctgctgatctaccagatgagcaacctggcc agcggcgtgcccgacagattcagcggcagcggcagcggcaccgacttcaccctgagaatc agcagagtggaggccgacgacgccggcgtgtactactgcgcccagaccctgggcctgccc agaaccttcggccagggcaccaaggtggagatcaagagaaacgacgcccagcccgccgtg tacctgttccagcccagccccgaccagctgcacaccggcagcgccagcgtggtgtgcctg -continued ctgaacagcttctaccccaaggacatcaacgtgaagtggaaggtggacggcgtgatccag gacaccggcatccaggagagcgtgaccgagcaggacagcaaggacagcacctacagcctg agcagcaccctgaccatgagcagcaccgagtacctgagccacgagctgtacagctgcgag atcacccacaagagcctgcccagcaccctgatcaagagcttccagagaagcgagtgccag agagtggac Variable regions of mouse anti-canine PDL-1:4F9
Heavy chain: DNA sequence
[SEQ ID NO: 73]
gaagtgcagctggtggagtctgggggaggcttagtgaagcctggagggtccctgaaactctc ctgtgcagcctctggattcactttcagtagctatgccatgtcttgggttcgccagactccgg acaagagactggagtgggtcgcaaccattagtgatggtggaagttacacccactaccccgac aatttaatgggccgattcaccatctccagagacaatgccaagaacaacctgtacctgcaaat gagccatctgaagtctgacgacacagccatgtattactgtgcacgagagagctatgatggtt actacgtggctaactggggccaagggactctggtcactgtctcagca Heavy chain: Amino acid sequence
[SEQ ID NO: 74]
EVQLVESGGGLVKPGGSLKLSCAASGFTFSSYAMSWVRQTPDKRLEWVATISDGGSYTHYPD

NLMGRFTISRDNAKNNLYLQMSHLKSDDTAMYYCARESYDGYYVANWGQGTLVTVSA

Light chain: DNA sequence
[SEQ ID NO: 75]
gatattgtgctaactcagtctccagccaccctgtctgtgaatccaggagatagcgtcagtct ttcctgcagggccagccaaagtattagcaacaacctacactggtatcaacaaaaatcacatg agtctccaaggcttctcatcaagtatgcttcccagtccatctctgggatcccctccaggttc agtggcagtggatcagggacagatttcactctcagtatcaacagtgtggagactgaagattt tggaatgtatttctgtcaacagagtaacagctggcctcagacgttcggtggaggcaccaagc tggaaatcaaa Light chain: Amino acid sequence
[SEQ ID NO: 76]
DIVLTQSPATLSVNPGDSVSLSCRASQSISNNLHWYQQKSHESPRLLIKYASQSISGIPSRF

SGSGSGTDFTLSINSVETEDFGMYFCQQSNSWPQTFGGGTKLEIK

Variable regions of mouse anti-canine PDL-1: Anti-PDL-1 5F12
Heavy chain: DNA sequence
[SEQ ID NO: 77]
caggtccagctacagcagtctggacctgagctggtgaagcctggggcttcagtgaagatatc ctgcaaggcttctggctacaccttcactgactactatatgaattgggtgaaacagaggcctg gacagggacttgagtggattggatggattttttcccggaagtggtgctacttactacaatgag aggttcatgggcaaggccacacttactgtggataaatcttccaacacagcctacatgttgtt cagtagcctgacctctgaggactctgcggtctatttctgtttaagatctgactgggacgtcg gggacttctggggccaaggcaccactctcacagtctcctca Heavy chain: Amino acid sequence
[SEQ ID NO: 78]
QVQLQQSGPELVKPGASVKISCKASGYTFTDYYMNWVKQRPGQGLEWIGWIFPGSGATYYNE

RFMGKATLTVDKSSNTAYMLFSSLTSEDSAVYFCLRSDWDVGDFWGQGTTLTVSS

Light chain: DNA sequence
[SEQ ID NO: 79]
gatattgtgatgacgcaggctgcattctccaatccagtcactcttggaacatcagcttccat ctcctgcaggtctagtaggagtctcctacatactaatggcatcacttatttgtcttggtttc tgcagaagccaggccagtctcctcagctcctgatttatcagatgtccaaccttgcctcagga

```
-continued
gtcccagacaggttcagtagcagtgggtcaggaactgatttcacactgagaatcagtagagt ggaggctgaggatgtgggtatttattactgtgctcaaactctaggacttcctcggacgttcg gtggaggcaccaagctggaaatcaaa Light chain: Amino acid sequence
                                                      [SEQ ID NO: 80]
DIVMTQAAFSNPVTLGTSASISCRSSRSLLHTNGITYLSWFLQKPGQSPQLLIYQMSNLASG
VPDRFSSSGSGTDFTLRISRVEAEDVGIYYCAQTLGLPRTFGGGTKLEIK
```

Example 5

Epitope Mapping of Anti-Canine PD-L1 Antibodies

The interaction of antibodies with their cognate protein antigens is mediated through the binding of specific amino acids of the antibodies (paratopes) with specific amino acids (epitopes) of target antigens. An epitope is an antigenic determinant that causes a specific reaction by an immunoglobulin. An epitope consists of a group of amino acids on the surface of the antigen. A protein of interest may contain several epitopes that are recognized by different antibodies. The epitopes recognized by antibodies are classified as linear or conformational epitopes. Linear epitopes are formed by a stretch of a continuous sequence of amino acids in a protein, while conformational epitopes are composed of amino acids that are discontinuous (e.g., far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs and help elucidate their mechanisms of action. Epitope information on PD-L1 can also elucidate unique cancer epitopes, and define the protective or pathogenic effects of vaccines. Epitope identification also can lead to development of subunit vaccines based on chemical or genetic coupling of the identified peptide epitope to a carrier protein or other immunostimulating agents.

Epitope mapping can be carried out using polyclonal or monoclonal antibodies and several methods are employed for epitope identification depending on the suspected nature of the epitope (i.e., linear versus conformational). Mapping linear epitopes is more straightforward and relatively, easier to perform. For this purpose, commercial services for linear epitope mapping often employ peptide scanning. In this case, an overlapping set of short peptide sequences of the target protein are chemically synthesized and tested for their ability to bind antibodies of interest. The strategy is rapid, high-throughput, and relatively inexpensive to perform. On the other hand, mapping of a discontinuous epitope is more technically challenging and requires more specialized techniques such as x-ray co-crystallography of a monoclonal antibody together with its target protein, Hydrogen-Deuterium (H/D) exchange, Mass Spectrometry coupled with enzymatic digestion as well as several other methods known to those skilled in the art.

Mapping of PD-L1 Epitopes Using Mass Spectrometry:

A method based on chemical crosslinking and mass spectroscopy detection was employed to identify the epitopes recognized by anti-canine PD-L1 mAbs [CovalX'® Instrument Incorporated]. The application of this technology to epitope mapping of canine PD-L1 resulted in identification of epitopes recognized by the indicated mAbs that are listed in Table 13. The results of epitope mapping of canine PD-L1 with mAb 4F9 shows that this mAb recognizes an epitope located in the extracellular domain of canine PD-L1 comprised of the amino acid sequence represented by SEQ ID NO: 82 and the amino acid sequence represented by SEQ ID NO: 83 [see, Table 13]. Moreover, the results of epitope mapping experiment with mAb 5F12 shows that this mAb recognizes an epitope located in the extracellular domain of canine PD-L1 comprised of the amino acid sequence represented by SEQ ID NO: 82. Notably, the location of the epitopes on canine PD-L1 identified herein are reasonably consistent with those recently reported for the corresponding human PD-L1, [Hao et al., J. Mol. Recognit. 28:269-276 (2015)] which provides further confidence for the determination provided above.

TABLE 13

PD-L1 EPITOPES RECOGNIZED BY ANTI-CANINE PD-L1 MABS

| ANTIBODY DESIGNATION | SEQ ID NO. | PEPTIDE SEQUENCE |
|---|---|---|
| 4F9 | 82 | LNLFALIVYWEMEDKKIIQF |
| 4F9 | 83 | KRITLKVHAPY |
| 5F12 | 82 | LNLFALIVYWEMEDKKIIQF |

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g., Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

We claim:

1. An isolated antibody or antigen binding fragment thereof that binds canine Programmed Death Ligand 1 (canine PD-L1) comprising
   (a) a CDRL1 that comprises the amino acid sequence of SEQ ID NO: 16;
   (b) a CDRL2 that comprises the amino acid sequence of SEQ ID NO: 17;
   (c) a CDRL3 that comprises the amino acid sequence of SEQ ID NO: 18;
   (d) a CDRH1 that comprises the amino acid sequence of SEQ ID NO: 13;
   (e) a CDRH2 that comprises the amino acid sequence of SEQ ID NO: 14; and
   (f) a CDRH3 that comprises the amino acid sequence of SEQ ID NO: 15;
   wherein the antibody and antigen binding fragment thereof bind canine PD-L1 and block the binding of canine PD-L1 to canine Programmed Death 1 (PD-1).

2. The isolated antibody of claim 1, wherein the antibody is a caninized antibody or antigen binding fragment thereof.

3. The caninized antibody or antigen binding fragment thereof of claim 2 that comprises a canine fragment crystallizable region (cFc region) that comprises an amino acid sequence selected from the group consisting of SEQ ID NO: 66 and SEQ ID NO: 68; wherein one to seven amino acid residues are substituted for at the indicated positions selected from the group consisting of P4, D31, N63, G64, T65, A93, and P95.

4. The caninized antibody of claim 3 or antigen binding fragment thereof, wherein there are two substitutions, D31A and N63A, and the amino acid sequence retains P4, G64, T65, A93, and P95.

5. The caninized antibody or antigen binding fragment thereof of claim 4 further comprising a canine light chain that comprises the amino acid sequence of SEQ ID NO: 38.

6. A pharmaceutical composition comprising the antibody of claim 5 or antigen binding fragment thereof and a pharmaceutically acceptable carrier or diluent.

7. The caninized antibody of claim 4 that comprises the amino acid sequence of SEQ ID NO: 26, wherein there is a proline residue at amino acid position 242, an alanine residue at amino acid position 269, an alanine residue at amino acid position 301, a glycine residue at amino acid position 302, a threonine residue at amino acid position 303, an alanine residue at amino acid position 331, and a proline residue at amino acid position 333.

8. The caninized antibody of claim 7 further comprising a canine light chain that comprises the amino acid sequence of SEQ ID NO: 38.

9. A pharmaceutical composition comprising the antibody of claim 8 and a pharmaceutically acceptable carrier or diluent.

10. The caninized antibody of claim 4 that comprises the amino acid sequence of SEQ ID NO: 28, wherein there is a proline residue at amino acid position 240, an alanine residue at amino acid position 267, an alanine residue at amino acid position 299, a glycine residue at amino acid position 300, a threonine residue at amino acid position 301, an alanine residue at amino acid position 329, and a proline residue at amino acid position 331.

11. The caninized antibody of claim 10 further comprising a canine light chain that comprises the amino acid sequence of SEQ ID NO: 38.

12. A pharmaceutical composition comprising the antibody of claim 8 and a pharmaceutically acceptable carrier or diluent.

* * * * *

SEQUENCE LISTING

<160> NUMBER OF SEQ ID NOS: 83

<210> SEQ ID NO 1
<211> LENGTH: 645
<212> TYPE: DNA
<213> ORGANISM: Artificial Sequence
<220> FEATURE:
<223> OTHER INFORMATION: Modified canine sequence
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (91)..(93)
<223> OTHER INFORMATION: n is a, c, g, or t
<220> FEATURE:
<221> NAME/KEY: misc_feature
<222> LOCATION: (187)..(195)
<223> OTHER INFORMATION: n is a, c, g, or t
<220> FEATURE:
<221> NAME/KEY: misc_feature
<222> LOCATION: (277)..(279)
<223> OTHER INFORMATION: n is a, c, g, or t
<220> FEATURE:
<221> NAME/KEY: misc_feature
<222> LOCATION: (283)..(285)
<223> OTHER INFORMATION: n is a, c, g, or t

<400> SEQUENCE: 1
ctgggcggcn nnagcgtgtt tattttccg ccgaaaccga aagataccct gctgattgcg      60 cgcacccccgg aagtgacctg cgtggtggtg nnnctggatc cggaagatcc ggaagtgcag    120
attagctggt ttgtggatgg caaacagatg cagaccgcga aacccagcc gcgcgaagaa     180 cagttttnnnn nnnnntatcg cgtggtgagc gtgctgccga ttggccatca ggattggctg    240
aaaggcaaac agtttacctg caaagtgaac aacaaannnc tgnnnagccc gattgaacgc    300
accattagca aagcgcgcgg ccaggcgcat cagccgagcg tgtatgtgct gccgccgagc    360
cgcgaagaac tgagcaaaaa caccgtgagc ctgacctgcc tgattaaaga tttttttccg    420
ccggatattg atgtggaatg gcagagcaac ggccagcagg aaccggaaag caaatatcgc    480
accaccccgc cgcagctgga tgaagatggc agctattttc tgtatagcaa actgagcgtg    540
gataaaagcc gctggcagcg cggcgatacc tttatttgcg cggtgatgca tgaagcgctg    600
cataaccatt atacccagga aagcctgagc catagcccgg gcaaa                    645

<210> SEQ ID NO 2
<211> LENGTH: 215
<212> TYPE: PRT
<213> ORGANISM: Artificial Sequence
<220> FEATURE:
<223> OTHER INFORMATION: Modified canine sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (63)..(65)
<223> OTHER INFORMATION: Xaa can be any naturally occurring amino acid
<220> FEATURE:

```
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid

<400> SEQUENCE: 2

Leu Gly Gly Xaa Ser Val Phe Ile Phe Pro Pro Lys Pro Lys Asp Thr
1               5                   10                  15

Leu Leu Ile Ala Arg Thr Pro Glu Val Thr Cys Val Val Xaa Leu
            20                  25                  30

Asp Pro Glu Asp Pro Glu Val Gln Ile Ser Trp Phe Val Asp Gly Lys
            35                  40                  45

Gln Met Gln Thr Ala Lys Thr Gln Pro Arg Glu Glu Gln Phe Xaa Xaa
    50                  55                  60

Xaa Tyr Arg Val Val Ser Val Leu Pro Ile Gly His Gln Asp Trp Leu
65                  70                  75                  80

Lys Gly Lys Gln Phe Thr Cys Lys Val Asn Asn Lys Xaa Leu Xaa Ser
                85                  90                  95

Pro Ile Glu Arg Thr Ile Ser Lys Ala Arg Gly Gln Ala His Gln Pro
            100                 105                 110

Ser Val Tyr Val Leu Pro Pro Ser Arg Glu Glu Leu Ser Lys Asn Thr
            115                 120                 125

Val Ser Leu Thr Cys Leu Ile Lys Asp Phe Phe Pro Pro Asp Ile Asp
130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Glu Ser
            195                 200                 205

Leu Ser His Ser Pro Gly Lys
            210             215

<210> SEQ ID NO 3
<211> LENGTH: 645
<212> TYPE: DNA
<213> ORGANISM: Artificial Sequence
<220> FEATURE:
<223> OTHER INFORMATION: Modified canine sequence
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (91)..(93)
<223> OTHER INFORMATION: n is a, c, g, or t
<220> FEATURE:
<221> NAME/KEY: misc_feature
<222> LOCATION: (187)..(195)
<223> OTHER INFORMATION: n is a, c, g, or t
<220> FEATURE:
<221> NAME/KEY: misc_feature
<222> LOCATION: (277)..(279)
<223> OTHER INFORMATION: n is a, c, g, or t
<220> FEATURE:
<221> NAME/KEY: misc_feature
<222> LOCATION: (283)..(285)
<223> OTHER INFORMATION: n is a, c, g, or t
```

<400> SEQUENCE: 3

```
ctgggcggcn nnagcgtgtt tattttccg ccgaaaccga agatattct ggtgaccgcg      60
cgcaccccga ccgtgacctg cgtggtggtg nnnctggatc cggaaaaccc ggaagtgcag    120
attagctggt ttgtggatag caaacaggtg cagaccgcga cacccagcc gcgcgaagaa    180
cagagcnnnn nnnnntatcg cgtggtgagc gtgctgccga ttggccatca ggattggctg    240
agcggcaaac agtttaaatg caaagtgaac aacaaannnc tgnnnagccc gattgaagaa    300
attattagca aaccccgggg ccaggcgcat cagccgaacg tgtatgtgct gccgccgagc    360
cgcgatgaaa tgagcaaaaa caccgtgacc ctgacctgcc tggtgaaaga ttttttccg     420
ccggaaattg atgtggaatg gcagagcaac ggccagcagg aaccggaaag caaatatcgc    480
atgacccgc cgcagctgga tgaagatggc agctattttc tgtatagcaa actgagcgtg    540
gataaaagcc gctggcagcg cggcgatacc tttatttgcg cggtgatgca tgaagcgctg    600
cataaccatt atacccagat tagcctgagc catagcccgg gcaaa                   645
```

<210> SEQ ID NO 4
<211> LENGTH: 215
<212> TYPE: PRT
<213> ORGANISM: Artificial Sequence
<220> FEATURE:
<223> OTHER INFORMATION: Modified canine sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (63)..(65)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid

<400> SEQUENCE: 4

```
Leu Gly Gly Xaa Ser Val Phe Ile Phe Pro Pro Lys Pro Lys Asp Ile
1               5                   10                  15
Leu Val Thr Ala Arg Thr Pro Thr Val Thr Cys Val Val Val Xaa Leu
            20                  25                  30
Asp Pro Glu Asn Pro Glu Val Gln Ile Ser Trp Phe Val Asp Ser Lys
        35                  40                  45
Gln Val Gln Thr Ala Asn Thr Gln Pro Arg Glu Glu Gln Ser Xaa Xaa
    50                  55                  60
Xaa Tyr Arg Val Val Ser Val Leu Pro Ile Gly His Gln Asp Trp Leu
65                  70                  75                  80
Ser Gly Lys Gln Phe Lys Cys Lys Val Asn Asn Lys Xaa Leu Xaa Ser
                85                  90                  95
Pro Ile Glu Glu Ile Ile Ser Lys Thr Pro Gly Gln Ala His Gln Pro
            100                 105                 110
Asn Val Tyr Val Leu Pro Pro Ser Arg Asp Glu Met Ser Lys Asn Thr
        115                 120                 125
```

```
Val Thr Leu Thr Cys Leu Val Lys Asp Phe Phe Pro Glu Ile Asp
    130                 135                 140

Val Glu Trp Gln Ser Asn Gly Gln Gln Glu Pro Glu Ser Lys Tyr Arg
145                 150                 155                 160

Met Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Ile Ser
        195                 200                 205

Leu Ser His Ser Pro Gly Lys
    210                 215

<210> SEQ ID NO 5
<211> LENGTH: 699
<212> TYPE: DNA
<213> ORGANISM: Artificial Sequence
<220> FEATURE:
<223> OTHER INFORMATION: Modified canine sequence

<400> SEQUENCE: 5
ccgaaagaaa gcacctgcaa atgcattccg ccgtgcccgg tgccggaaag cctgggcggc      60
ccgagcgtgt ttattttcc gccgaaaccg aaagatattc tgcgcattac ccgcaccccg      120
gaaattacct gcgtggtgct ggatctgggc cgcgaagatc cggaagtgca gattagctgg      180
tttgtggatg gcaaagaagt gcataccgcg aaaacccagc cgcgcgaaca gcagtttaac      240
agcacctatc gcgtggtgag cgtgctgccg attgaacatc aggattggct gaccggcaaa      300
gaatttaaat gccgcgtgaa ccatattggc ctgccgagcc cgattgaacg caccattagc      360
aaagcgcgcg gccaggcgca tcagccgagc gtgtatgtgc tgccgccgag cccgaaagaa      420
ctgagcagca gcgataccgt gaccctgacc tgcctgatta agatttttt ccgccggaa       480 attgatgtgg aatggcagag caacggccag ccggaaccgg aaagcaaata tcataccacc      540
gcgccgcagc tggatgaaga tggcagctat tttctgtata gcaaactgag cgtggataaa      600
agccgctggc agcagggcga tacctttacc tgcgcggtga tgcatgaagc gctgcagaac      660
cattataccg atctgagcct gagccatagc ccgggcaaa                            699

<210> SEQ ID NO 6
<211> LENGTH: 233
<212> TYPE: PRT
<213> ORGANISM: Artificial Sequence
<220> FEATURE:
<223> OTHER INFORMATION: Modified canine sequence

<400> SEQUENCE: 6

Pro Lys Glu Ser Thr Cys Lys Cys Ile Pro Pro Cys Pro Val Pro Glu
1               5                   10                  15

Ser Leu Gly Gly Pro Ser Val Phe Ile Phe Pro Pro Lys Pro Lys Asp
            20                  25                  30

Ile Leu Arg Ile Thr Arg Thr Pro Glu Ile Thr Cys Val Val Leu Asp
        35                  40                  45

Leu Gly Arg Glu Asp Pro Glu Val Gln Ile Ser Trp Phe Val Asp Gly
    50                  55                  60

Lys Glu Val His Thr Ala Lys Thr Gln Pro Arg Glu Gln Gln Phe Asn
65                  70                  75                  80

Ser Thr Tyr Arg Val Val Ser Val Leu Pro Ile Glu His Gln Asp Trp
                85                  90                  95
```

Leu Thr Gly Lys Glu Phe Lys Cys Arg Val Asn His Ile Gly Leu Pro
                100                 105                 110

Ser Pro Ile Glu Arg Thr Ile Ser Lys Ala Arg Gly Gln Ala His Gln
            115                 120                 125

Pro Ser Val Tyr Val Leu Pro Pro Ser Pro Lys Glu Leu Ser Ser Ser
        130                 135                 140

Asp Thr Val Thr Leu Thr Cys Leu Ile Lys Asp Phe Phe Pro Pro Glu
145                 150                 155                 160

Ile Asp Val Glu Trp Gln Ser Asn Gly Gln Pro Glu Pro Glu Ser Lys
                165                 170                 175

Tyr His Thr Thr Ala Pro Gln Leu Asp Glu Asp Gly Ser Tyr Phe Leu
            180                 185                 190

Tyr Ser Lys Leu Ser Val Asp Lys Ser Arg Trp Gln Gln Gly Asp Thr
        195                 200                 205

Phe Thr Cys Ala Val Met His Glu Ala Leu Gln Asn His Tyr Thr Asp
210                 215                 220

Leu Ser Leu Ser His Ser Pro Gly Lys
225                 230

<210> SEQ ID NO 7
<211> LENGTH: 699
<212> TYPE: DNA
<213> ORGANISM: Artificial Sequence
<220> FEATURE:
<223> OTHER INFORMATION: Modified canine sequence

<400> SEQUENCE: 7
tttaacgaat gccgctgcac cgataccccg ccgtgcccgg tgccggaacc gctgggcggc      60
ccgagcgtgt ttatttttcc gccgaaaccg aaagatattc tgcgcattac cgcaccccg     120
gaaattacct gcgtggtgct ggatctgggc cgcgaagatc cggaagtgca gattagctgg     180
tttgtggatg gcaaagaagt gcataccgcg aaaacccagc cgcgcgaaca gcagtttaac     240
agcacctatc gcgtggtgag cgtgctgccg attaacatc aggattggct gaccggcaaa     300
gaatttaaat gccgcgtgaa ccatattggc ctgccgagcc cgattgaacg caccattagc     360
aaagcgcgcg gccaggcgca tcagccgagc gtgtatgtgc tgccgccgag cccgaaagaa     420
ctgagcagca gcgataccgt gaccctgacc tgcctgatta agatttttt tccgccggaa     480
attgatgtgg aatggcagag caacggccag ccggaaccgg aaagcaaata tcataccacc     540
gcgccgcagc tggatgaaga tggcagctat tttctgtata gcaaactgag cgtggataaa     600
agccgctggc agcagggcga tacctttacc tgcgcggtga tgcatgaagc gctgcagaac     660
cattataccg atctgagcct gagccatagc ccgggcaaa                           699

<210> SEQ ID NO 8
<211> LENGTH: 233
<212> TYPE: PRT
<213> ORGANISM: Artificial Sequence
<220> FEATURE:
<223> OTHER INFORMATION: Modified canine sequence

<400> SEQUENCE: 8

Phe Asn Glu Cys Arg Cys Thr Asp Thr Pro Pro Cys Pro Val Pro Glu
1               5                   10                  15

Pro Leu Gly Gly Pro Ser Val Phe Ile Phe Pro Pro Lys Pro Lys Asp
            20                  25                  30

Ile Leu Arg Ile Thr Arg Thr Pro Glu Ile Thr Cys Val Val Leu Asp

|   |   | 35 |   |   |   | 40 |   |   |   | 45 |   |
|---|---|---|---|---|---|---|---|---|---|---|---|

Leu Gly Arg Glu Asp Pro Glu Val Gln Ile Ser Trp Phe Val Asp Gly
 50                  55                  60

Lys Glu Val His Thr Ala Lys Thr Gln Pro Arg Glu Gln Gln Phe Asn
65                   70                  75                  80

Ser Thr Tyr Arg Val Val Ser Val Leu Pro Ile Glu His Gln Asp Trp
                 85                  90                  95

Leu Thr Gly Lys Glu Phe Lys Cys Arg Val Asn His Ile Gly Leu Pro
             100                 105                 110

Ser Pro Ile Glu Arg Thr Ile Ser Lys Ala Arg Gly Gln Ala His Gln
         115                 120                 125

Pro Ser Val Tyr Val Leu Pro Pro Ser Pro Lys Glu Leu Ser Ser Ser
     130                 135                 140

Asp Thr Val Thr Leu Thr Cys Leu Ile Lys Asp Phe Phe Pro Pro Glu
145                 150                 155                 160

Ile Asp Val Glu Trp Gln Ser Asn Gly Gln Pro Glu Pro Glu Ser Lys
                 165                 170                 175

Tyr His Thr Thr Ala Pro Gln Leu Asp Glu Asp Gly Ser Tyr Phe Leu
             180                 185                 190

Tyr Ser Lys Leu Ser Val Asp Lys Ser Arg Trp Gln Gln Gly Asp Thr
         195                 200                 205

Phe Thr Cys Ala Val Met His Glu Ala Leu Gln Asn His Tyr Thr Asp
     210                 215                 220

Leu Ser Leu Ser His Ser Pro Gly Lys
225                 230

<210> SEQ ID NO 9
<211> LENGTH: 714
<212> TYPE: DNA
<213> ORGANISM: Artificial Sequence
<220> FEATURE:
<223> OTHER INFORMATION: Modified canine sequence

<400> SEQUENCE: 9

```
ccgaaacgcg aaaacggccg cgtgccgcgc ccgccggatt gcccgaaatg cccggcgccg      60
gaaatgctgg gcggcccgag cgtgtttatt tttccgccga accgaaaga tattctgcgc     120 attacccgca ccccggaaat tacctgcgtg gtgctggatc tgggccgcga agatccggaa    180
gtgcagatta gctggtttgt ggatggcaaa gaagtgcata ccgcgaaaac ccagccgcgc    240
gaacagcagt ttaacagcac ctatcgcgtg gtgagcgtgc tgccgattga acatcaggat    300
tggctgaccg gcaaagaatt taaatgccgc gtgaaccata ttggcctgcc gagcccgatt    360
gaacgcacca ttagcaaagc gcgcggccag gcgcatcagc cgagcgtgta tgtgctgccg    420
ccgagcccga agaactgag cagcagcgat accgtgaccc tgacctgcct gattaaagat    480
ttttttccgc cggaaattga tgtggaatgg cagagcaacg gccagccgga accggaaagc    540
aaatatcata ccaccgcgcc gcagctggat gaagatggca gctatttcct gtatagcaaa    600
ctgagcgtgg ataaaagccg ctggcagcag ggcgatacct taccgtgcgc ggtgatgcat    660
gaagcgctgc agaaccatta taccgatctg agcctgagcc atagcccggg caaa          714
```

<210> SEQ ID NO 10
<211> LENGTH: 238
<212> TYPE: PRT
<213> ORGANISM: Artificial Sequence
<220> FEATURE:
<223> OTHER INFORMATION: Modified canine sequence

<400> SEQUENCE: 10

```
Pro Lys Arg Glu Asn Gly Arg Val Pro Arg Pro Asp Cys Pro Lys
1               5                   10                  15
Cys Pro Ala Pro Glu Met Leu Gly Gly Pro Ser Val Phe Ile Phe Pro
            20                  25                  30
Pro Lys Pro Lys Asp Ile Leu Arg Ile Thr Arg Thr Pro Glu Ile Thr
        35                  40                  45
Cys Val Val Leu Asp Leu Gly Arg Glu Asp Pro Glu Val Gln Ile Ser
    50                  55                  60
Trp Phe Val Asp Gly Lys Glu Val His Thr Ala Lys Thr Gln Pro Arg
65                  70                  75                  80
Glu Gln Gln Phe Asn Ser Thr Tyr Arg Val Val Ser Val Leu Pro Ile
                85                  90                  95
Glu His Gln Asp Trp Leu Thr Gly Lys Glu Phe Lys Cys Arg Val Asn
            100                 105                 110
His Ile Gly Leu Pro Ser Pro Ile Glu Arg Thr Ile Ser Lys Ala Arg
        115                 120                 125
Gly Gln Ala His Gln Pro Ser Val Tyr Val Leu Pro Pro Ser Pro Lys
    130                 135                 140
Glu Leu Ser Ser Ser Asp Thr Val Thr Leu Thr Cys Leu Ile Lys Asp
145                 150                 155                 160
Phe Phe Pro Pro Glu Ile Asp Val Glu Trp Gln Ser Asn Gly Gln Pro
                165                 170                 175
Glu Pro Glu Ser Lys Tyr His Thr Thr Ala Pro Gln Leu Asp Glu Asp
            180                 185                 190
Gly Ser Tyr Phe Leu Tyr Ser Lys Leu Ser Val Asp Lys Ser Arg Trp
        195                 200                 205
Gln Gln Gly Asp Thr Phe Thr Cys Ala Val Met His Glu Ala Leu Gln
    210                 215                 220
Asn His Tyr Thr Asp Leu Ser Leu Ser His Ser Pro Gly Lys
225                 230                 235
```

<210> SEQ ID NO 11
<211> LENGTH: 708
<212> TYPE: DNA
<213> ORGANISM: Artificial Sequence
<220> FEATURE:
<223> OTHER INFORMATION: Modified canine sequence

<400> SEQUENCE: 11

```
gccaaggagt gcgagtgcaa gtgcaactgc aacaactgcc cctgccccgg ctgcggcctg      60
ctgggcggcc ccagcgtgtt catcttcccc cccaagccca aggacatcct gagaatcacc     120
agaacccccg agatcacctg cgtggtgctg gacctgggca gagaggaccc cgaggtgcag     180
atcagctggt tcgtggacgg caaggaggtg cacaccgcca agacccagcc cagagagcag     240
cagttcaaca gcacctacag agtggtgagc gtgctgccca tcgagcacca ggactggctg     300
accggcaagg agttcaagtg cagagtgaac cacatcggcc tgcccagccc catcgagaga     360
accatcagca aggccagagg ccaggcccac cagcccagcg tgtacgtgct gccccccagc     420
cccaaggagc tgagcagcag cgacaccgtg accctgacct gcctgatcaa ggacttcttc     480
ccccccgaga tcgacgtgga gtggcagagc aacggccagc ccgagcccga gagcaagtac     540
cacaccaccg cccccagct ggacgaggac ggcagctact cctgtacag caagctgagc     600
gtggacaaga gcagatggca gcagggcgac accttcacct gcgccgtgat gcacgaggcc     660
```
ctgcagaacc actacaccga cctgagcctg agccacagcc ccggcaag                708

<210> SEQ ID NO 12
<211> LENGTH: 236
<212> TYPE: PRT
<213> ORGANISM: Artificial Sequence
<220> FEATURE:
<223> OTHER INFORMATION: Modified canine sequence

<400> SEQUENCE: 12

```
Ala Lys Glu Cys Glu Cys Lys Cys Asn Cys Asn Asn Cys Pro Cys Pro
1               5                   10                  15
Gly Cys Gly Leu Leu Gly Gly Pro Ser Val Phe Ile Phe Pro Pro Lys
            20                  25                  30
Pro Lys Asp Ile Leu Arg Ile Thr Arg Thr Pro Glu Ile Thr Cys Val
        35                  40                  45
Val Leu Asp Leu Gly Arg Glu Asp Pro Glu Val Gln Ile Ser Trp Phe
50                  55                  60
Val Asp Gly Lys Glu Val His Thr Ala Lys Thr Gln Pro Arg Glu Gln
65                  70                  75                  80
Gln Phe Asn Ser Thr Tyr Arg Val Val Ser Val Leu Pro Ile Glu His
                85                  90                  95
Gln Asp Trp Leu Thr Gly Lys Glu Phe Lys Cys Arg Val Asn His Ile
            100                 105                 110
Gly Leu Pro Ser Pro Ile Glu Arg Thr Ile Ser Lys Ala Arg Gly Gln
        115                 120                 125
Ala His Gln Pro Ser Val Tyr Val Leu Pro Pro Ser Pro Lys Glu Leu
130                 135                 140
Ser Ser Ser Asp Thr Val Thr Leu Thr Cys Leu Ile Lys Asp Phe Phe
145                 150                 155                 160
Pro Pro Glu Ile Asp Val Glu Trp Gln Ser Asn Gly Gln Pro Glu Pro
                165                 170                 175
Glu Ser Lys Tyr His Thr Thr Ala Pro Gln Leu Asp Glu Asp Gly Ser
            180                 185                 190
Tyr Phe Leu Tyr Ser Lys Leu Ser Val Asp Lys Ser Arg Trp Gln Gln
        195                 200                 205
Gly Asp Thr Phe Thr Cys Ala Val Met His Glu Ala Leu Gln Asn His
210                 215                 220
Tyr Thr Asp Leu Ser Leu Ser His Ser Pro Gly Lys
225                 230                 235
```

<210> SEQ ID NO 13
<211> LENGTH: 5
<212> TYPE: PRT
<213> ORGANISM: Mus musculus

<400> SEQUENCE: 13

```
Ser Tyr Ala Met Ser
1               5
```

<210> SEQ ID NO 14
<211> LENGTH: 17
<212> TYPE: PRT
<213> ORGANISM: Mus musculus

<400> SEQUENCE: 14

```
Thr Ile Ser Asp Gly Gly Ser Tyr Thr His Tyr Pro Asp Asn Leu Met
1               5                   10                  15
```

Gly

<210> SEQ ID NO 15
<211> LENGTH: 10
<212> TYPE: PRT
<213> ORGANISM: Mus musculus

<400> SEQUENCE: 15

Glu Ser Tyr Asp Gly Tyr Tyr Val Ala Asn
1               5                   10

<210> SEQ ID NO 16
<211> LENGTH: 11
<212> TYPE: PRT
<213> ORGANISM: Mus musculus

<400> SEQUENCE: 16

Arg Ala Ser Gln Ser Ile Ser Asn Asn Leu His
1               5                   10

<210> SEQ ID NO 17
<211> LENGTH: 7
<212> TYPE: PRT
<213> ORGANISM: Mus musculus

<400> SEQUENCE: 17

Tyr Ala Ser Gln Ser Ile Ser
1               5

<210> SEQ ID NO 18
<211> LENGTH: 9
<212> TYPE: PRT
<213> ORGANISM: Mus musculus

<400> SEQUENCE: 18

Gln Gln Ser Asn Ser Trp Pro Gln Thr
1               5

<210> SEQ ID NO 19
<211> LENGTH: 5
<212> TYPE: PRT
<213> ORGANISM: Mus musculus

<400> SEQUENCE: 19

Asp Tyr Tyr Met Asn
1               5

<210> SEQ ID NO 20
<211> LENGTH: 17
<212> TYPE: PRT
<213> ORGANISM: Mus musculus

<400> SEQUENCE: 20

Trp Ile Phe Pro Gly Ser Gly Ala Thr Tyr Tyr Asn Glu Arg Phe Met
1               5                   10                  15

Gly

<210> SEQ ID NO 21
<211> LENGTH: 8
<212> TYPE: PRT
<213> ORGANISM: Mus musculus

<400> SEQUENCE: 21

Ser Asp Trp Asp Val Gly Asp Phe
1               5

<210> SEQ ID NO 22
<211> LENGTH: 16
<212> TYPE: PRT
<213> ORGANISM: Mus musculus

<400> SEQUENCE: 22

Arg Ser Ser Arg Ser Leu Leu His Thr Asn Gly Ile Thr Tyr Leu Ser
1               5                   10                  15

<210> SEQ ID NO 23
<211> LENGTH: 7
<212> TYPE: PRT
<213> ORGANISM: Mus musculus

<400> SEQUENCE: 23

Gln Met Ser Asn Leu Ala Ser
1               5

<210> SEQ ID NO 24
<211> LENGTH: 9
<212> TYPE: PRT
<213> ORGANISM: Mus musculus

<400> SEQUENCE: 24

Ala Gln Thr Leu Gly Leu Pro Arg Thr
1               5

<210> SEQ ID NO 25
<211> LENGTH: 1359
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (724)..(726)
<223> OTHER INFORMATION: n is a, c, g, or t
<220> FEATURE:
<221> NAME/KEY: misc_feature
<222> LOCATION: (805)..(807)
<223> OTHER INFORMATION: n is a, c, g, or t
<220> FEATURE:
<221> NAME/KEY: misc_feature
<222> LOCATION: (901)..(909)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t
<220> FEATURE:
<221> NAME/KEY: misc_feature
<222> LOCATION: (997)..(999)
<223> OTHER INFORMATION: n is a, c, g, or t

<400> SEQUENCE: 25
gaggtgcagc tggtgcagag cggcggcgac ctggtgaagc ccggcggcag cgtgagactg      60
agctgcgtgg ccagcggctt caccttcagc tacgccatga gctgggtgag acaggccccc     120
ggcaagggcc tgcagtggat gggcaccatc agcgacggcg gcagctacac ccactacccc     180
gacaacctga tgggcagatt caccttcagc ctggacaccg ccaagaacac cgcctacctg     240
cagctgaaca gcctgagagc cgaggacacc gccgtgtact actgcgccag agagagctac     300
gacggctact acgtggccaa ctggggccag ggcaccctgg tgaccgtgag cagcgccagc     360
accaccgccc ccagcgtgtt ccccctggcc ccagctgcg gcagcaccag cggcagcacc     420

```
gtggccctgg cctgcctggt gagcggctac ttccccgagc ccgtgaccgt gagctggaac    480
agcggcagcc tgaccagcgg cgtgcacacc ttccccagcg tgctgcagag cagcggcctg    540
tacagcctga gcagcatggt gaccgtgccc agcagcagat ggcccagcga gaccttcacc    600
tgcaacgtgg cccaccccgc cagcaagacc aaggtggaca agcccgtgcc caagagagag    660
aacggcagag tgcccagacc ccccgactgc cccaagtgcc ccgcccccga tgctgggc      720 ggcnnnagcg tgttcatctt ccccccccaag cccaaggaca ccctgctgat cgccagaacc    780
cccgaggtga cctgcgtggt ggtgnnnctg gaccccgagg accccgaggt gcagatcagc    840
tggttcgtgg acggcaagca gatgcagacc gccaagaccc agcccagaga ggagcagttc    900
nnnnnnnnnt acagagtggt gagcgtgctg cccatcggcc accaggactg gctgaagggc    960
aagcagttca cctgcaaggt gaacaacaag nnnctgnnna gccccatcga gaaccatc     1020 agcaaggcca gaggccaggc ccaccagccc agcgtgtacg tgctgccccc cagcagagag   1080
gagctgagca gaacaccgt gagcctgacc tgcctgatca aggacttctt ccccccccgac   1140 atcgacgtgg agtggcagag caacggccag caggagcccg agagcaagta cagaaccacc   1200 ccccccccagc tggacgagga cggcagctac ttcctgtaca gcaagctgag cgtggacaag   1260
agcagatggc agagaggcga caccttcatc tgcgccgtga tgcacgaggc cctgcacaac   1320
cactacaccc aggagagcct gagccacagc cccggcaag                          1359
```

<210> SEQ ID NO 26
<211> LENGTH: 453
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (301)..(303)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid

<400> SEQUENCE: 26

```
Glu Val Gln Leu Val Gln Ser Gly Gly Asp Leu Val Lys Pro Gly Gly
1               5                   10                  15

Ser Val Arg Leu Ser Cys Val Ala Ser Gly Phe Thr Phe Ser Tyr Ala
            20                  25                  30

Met Ser Trp Val Arg Gln Ala Pro Gly Lys Gly Leu Gln Trp Met Gly
        35                  40                  45

Thr Ile Ser Asp Gly Gly Ser Tyr Thr His Tyr Pro Asp Asn Leu Met
    50                  55                  60

Gly Arg Phe Thr Phe Ser Leu Asp Thr Ala Lys Asn Thr Ala Tyr Leu
65                  70                  75                  80

Gln Leu Asn Ser Leu Arg Ala Glu Asp Thr Ala Val Tyr Tyr Cys Ala
```

85                  90                  95
Arg Glu Ser Tyr Asp Gly Tyr Tyr Val Ala Asn Trp Gly Gln Gly Thr
            100                 105                 110

Leu Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
            165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
            195                 200                 205

Lys Thr Lys Val Asp Lys Pro Val Pro Lys Arg Glu Asn Gly Arg Val
        210                 215                 220

Pro Arg Pro Pro Asp Cys Pro Lys Cys Pro Ala Pro Glu Met Leu Gly
225                 230                 235                 240

Gly Xaa Ser Val Phe Ile Phe Pro Pro Lys Pro Lys Asp Thr Leu Leu
                245                 250                 255

Ile Ala Arg Thr Pro Glu Val Thr Cys Val Val Xaa Leu Asp Pro
            260                 265                 270

Glu Asp Pro Glu Val Gln Ile Ser Trp Phe Val Asp Gly Lys Gln Met
        275                 280                 285

Gln Thr Ala Lys Thr Gln Pro Arg Glu Glu Gln Phe Xaa Xaa Xaa Tyr
        290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Xaa Leu Xaa Ser Pro Ile
                325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
        355                 360                 365

Leu Thr Cys Leu Ile Lys Asp Phe Phe Pro Pro Asp Ile Asp Val Glu
        370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
            405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
            435                 440                 445

His Ser Pro Gly Lys
        450

<210> SEQ ID NO 27
<211> LENGTH: 1353
<212> TYPE: DNA
<213> ORGANISM: Artificial Sequence
<220> FEATURE:
<223> OTHER INFORMATION: caninized mouse antibody
<220> FEATURE:

```
<221> NAME/KEY: misc_feature
<222> LOCATION: (718)..(720)
<223> OTHER INFORMATION: n is a, c, g, or t
<220> FEATURE:
<221> NAME/KEY: misc_feature
<222> LOCATION: (799)..(801)
<223> OTHER INFORMATION: n is a, c, g, or t
<220> FEATURE:
<221> NAME/KEY: misc_feature
<222> LOCATION: (895)..(903)
<223> OTHER INFORMATION: n is a, c, g, or t
<220> FEATURE:
<221> NAME/KEY: misc_feature
<222> LOCATION: (985)..(987)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t

<400> SEQUENCE: 27
gaggtgcagc tggtgcagag cggcggcgac ctggtgaagc ccggcggcag cgtgagactg      60
agctgcgtgg ccagcggctt caccttcagc tacgccatga gctgggtgag acaggccccc     120
ggcaagggcc tgcagtggat gggcaccatc agcgacggcg gcagctacac ccactacccc     180
gacaacctga tgggcagatt caccttcagc ctggacaccg ccaagaacac cgcctacctg     240
cagctgaaca gcctgagagc cgaggacacc gccgtgtact actgcgccag agagagctac     300
gacggctact acgtggccaa ctggggccag ggcaccctgg tgaccgtgag cagcgccagc     360
accaccgccc ccagcgtgtt ccccctggcc ccagctgcg gcagccagag cggcagcacc      420
gtggccctgg cctgcctggt gagcggctac atccccgagc ccgtgaccgt gagctggaac     480
agcgtgagcc tgaccagcgg cgtgcacacc ttccccagcg tgctgcagag cagcggcctg     540
tacagcctga gcagcatggt gaccgtgccc agcagcagat ggcccagcga gaccttcacc     600
tgcaacgtgg cccaccccgc caccaacacc aaggtggaca gcccgtggc caaggagtgc      660 gagtgcaagt gcaactgcaa caactgcccc tgccccggct cgggcctgct gggcggcnnn     720
agcgtgttca tcttccccc caagcccaag gacatcctgg tgaccgccag aaccccccacc     780 gtgacctgcg tggtggtgnn nctgaccccc gagaaccccg aggtgcagat cagctggttc     840
gtggacagca agcaggtgca gaccgccaac acccagccca gagaggagca gagcnnnnnn     900
nnntacagag tggtgagcgt gctgcccatc ggccaccagg actggctgag cggcaagcag     960
ttcaagtgca aggtgaacaa caagnnnctg nnnagcccca tcgaggagat catcagcaag    1020
acccccggcc aggcccacca gcccaacgtg tacgtgctgc cccccagcag agacgagatg    1080
agcaagaaca ccgtgaccct gacctgcctg gtgaaggact tcttcccccc cgagatcgac    1140
gtggagtggc agagcaacgg ccagcaggag cccgagagca gtacagaat gaccccccccc   1200 cagctggacg aggacggcag ctacttcctg tacagcaagc tgagcgtgga caagagcaga    1260
tggcagagag cgacaccttt catctgcgcc gtgatgcacg aggccctgca caaccactac    1320
acccagatca gcctgagcca cagccccggc aag                                 1353

<210> SEQ ID NO 28
<211> LENGTH: 451
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (240)..(240)
<223> OTHER INFORMATION: Xaa can be any naturally occurring amino acid
```

```
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (299)..(301)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid

<400> SEQUENCE: 28

Glu Val Gln Leu Val Gln Ser Gly Gly Asp Leu Val Lys Pro Gly Gly
1               5                   10                  15

Ser Val Arg Leu Ser Cys Val Ala Ser Gly Phe Thr Phe Ser Tyr Ala
            20                  25                  30

Met Ser Trp Val Arg Gln Ala Pro Gly Lys Gly Leu Gln Trp Met Gly
        35                  40                  45

Thr Ile Ser Asp Gly Gly Ser Tyr Thr His Tyr Pro Asp Asn Leu Met
    50                  55                  60

Gly Arg Phe Thr Phe Ser Leu Asp Thr Ala Lys Asn Thr Ala Tyr Leu
65                  70                  75                  80

Gln Leu Asn Ser Leu Arg Ala Glu Asp Thr Ala Val Tyr Tyr Cys Ala
                85                  90                  95

Arg Glu Ser Tyr Asp Gly Tyr Tyr Val Ala Asn Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Gln Ser Gly Ser Thr Val Ala Leu Ala
    130                 135                 140

Cys Leu Val Ser Gly Tyr Ile Pro Glu Pro Val Thr Val Ser Trp Asn
145                 150                 155                 160

Ser Val Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Thr
        195                 200                 205

Asn Thr Lys Val Asp Lys Pro Val Ala Lys Glu Glu Cys Lys Cys
    210                 215                 220

Asn Cys Asn Asn Cys Pro Cys Pro Gly Cys Gly Leu Leu Gly Gly Xaa
225                 230                 235                 240

Ser Val Phe Ile Phe Pro Pro Lys Pro Lys Asp Ile Leu Val Thr Ala
                245                 250                 255

Arg Thr Pro Thr Val Thr Cys Val Val Val Xaa Leu Asp Pro Glu Asn
            260                 265                 270

Pro Glu Val Gln Ile Ser Trp Phe Val Asp Ser Lys Gln Val Gln Thr
        275                 280                 285

Ala Asn Thr Gln Pro Arg Glu Glu Gln Xaa Xaa Xaa Tyr Arg Val
    290                 295                 300

Val Ser Val Leu Pro Ile Gly His Gln Asp Trp Leu Ser Gly Lys Gln
305                 310                 315                 320
```

```
Phe Lys Cys Lys Val Asn Asn Lys Xaa Leu Xaa Ser Pro Ile Glu Glu
            325                 330                 335

Ile Ile Ser Lys Thr Pro Gly Gln Ala His Gln Pro Asn Val Tyr Val
            340                 345                 350

Leu Pro Pro Ser Arg Asp Glu Met Ser Lys Asn Thr Val Thr Leu Thr
            355                 360                 365

Cys Leu Val Lys Asp Phe Phe Pro Glu Ile Asp Val Glu Trp Gln
370                 375                 380

Ser Asn Gly Gln Gln Glu Pro Glu Ser Lys Tyr Arg Met Thr Pro Pro
385                 390                 395                 400

Gln Leu Asp Glu Asp Gly Ser Tyr Phe Leu Tyr Ser Lys Leu Ser Val
            405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Ile Ser Leu Ser His Ser
            435                 440                 445

Pro Gly Lys
    450
```

```
<210> SEQ ID NO 29
<211> LENGTH: 1353
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (718)..(720)
<223> OTHER INFORMATION: n is a, c, g, or t
<220> FEATURE:
<221> NAME/KEY: misc_feature
<222> LOCATION: (799)..(801)
<223> OTHER INFORMATION: n is a, c, g, or t
<220> FEATURE:
<221> NAME/KEY: misc_feature
<222> LOCATION: (895)..(903)
<223> OTHER INFORMATION: n is a, c, g, or t
<220> FEATURE:
<221> NAME/KEY: misc_feature
<222> LOCATION: (985)..(987)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t

<400> SEQUENCE: 29
gaggtgcagc tggtgcagag cggcggcgac ctggtgaagc ccggcggcag cgtgagactg      60
agctgcgtgg ccagcttcac cttcgactac tacatgaact gggtgagaca ggcccccggc     120
aagggcctgc agtggatcgg cagatggatc ttccccggca cggcgccac ctactacaac     180 gagagattca tgggcaaggc caccatcagc gccgacaccg ccaagaacac cgcctacatg     240
cagctgaaca gcctgagagc cgaggacacc gccgtgtact actgcctgag aagcgactgg     300
gacgtgggcg acttctgggg ccagggcacc ctggtgaccg tgagcagcgc cagcaccacc     360
gcccccagcg tgttccccct ggccccagc tgcggcagca ccagcggcag caccgtggcc     420
ctggcctgcc tggtgagcgg ctacttcccc gagcccgtga ccgtgagctg aacagcggc     480 agcctgacca gcggcgtgca caccttcccc agcgtgctgc agagcagcgg cctgtacagc     540
ctgagcagca tggtgaccgt gcccagcagc agatggccca gcgagacctt cacctgcaac     600
gtggcccacc ccgccagcaa gaccaaggtg gacaagcccg tgcccaagag agagaacggc     660
```

```
agagtgccca gaccccccga ctgccccaag tgccccgccc ccgagatgct gggcggcnnn    720
agcgtgttca tcttcccccc caagcccaag gacaccctgc tgatcgccag aaccccgag     780 gtgacctgcg tggtggtgnn nctggacccc gaggacccg aggtgcagat cagctggttc     840
gtggacggca gcagatgca gaccgccaag acccagccca gagaggagca gttcnnnnnn     900
nnntacagag tggtgagcgt gctgcccatc ggccaccagg actggctgaa gggcaagcag    960
ttcacctgca aggtgaacaa caagnnnctg nnnagcccca tcgagagaac catcagcaag    1020
gccagaggcc aggcccacca gcccagcgtg tacgtgctgc ccccagcag agaggagctg     1080 agcaagaaca ccgtgagcct gacctgcctg atcaaggact tcttccccc cgacatcgac     1140 gtggagtggc agagcaacgg ccagcaggag cccgagagca agtacagaac caccccccc     1200 cagctggacg aggacggcag ctacttcctg tacagcaagc tgagcgtgga caagagcaga    1260
tggcagagag gcgacacctt catctgcgcc gtgatgcacg aggccctgca caaccactac    1320
acccaggaga gcctgagcca gcccccggc aag                                  1353
```

<210> SEQ ID NO 30
<211> LENGTH: 451
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (299)..(301)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid

<400> SEQUENCE: 30

Glu Val Gln Leu Val Gln Ser Gly Gly Asp Leu Val Lys Pro Gly Gly
1               5                   10                  15

Ser Val Arg Leu Ser Cys Val Ala Ser Phe Thr Phe Asp Tyr Tyr Met
            20                  25                  30

Asn Trp Val Arg Gln Ala Pro Gly Lys Gly Leu Gln Trp Ile Gly Arg
        35                  40                  45

Trp Ile Phe Pro Gly Ser Gly Ala Thr Tyr Tyr Asn Glu Arg Phe Met
    50                  55                  60

Gly Lys Ala Thr Ile Ser Ala Asp Thr Ala Lys Asn Thr Ala Tyr Met
65                  70                  75                  80

Gln Leu Asn Ser Leu Arg Ala Glu Asp Thr Ala Val Tyr Tyr Cys Leu
                85                  90                  95

Arg Ser Asp Trp Asp Val Gly Asp Phe Trp Gly Gln Gly Thr Leu Val
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu

```
                130             135             140
Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Xaa
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Xaa Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Xaa Xaa Xaa Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Xaa Leu Xaa Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
450

<210> SEQ ID NO 31
<211> LENGTH: 1347
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (712)..(714)
<223> OTHER INFORMATION: n is a, c, g, or t
<220> FEATURE:
<221> NAME/KEY: misc_feature
<222> LOCATION: (793)..(795)
<223> OTHER INFORMATION: n is a, c, g, or t
<220> FEATURE:
<221> NAME/KEY: misc_feature
```

<222> LOCATION: (889)..(897)
<223> OTHER INFORMATION: n is a, c, g, or t
<220> FEATURE:
<221> NAME/KEY: misc_feature
<222> LOCATION: (979)..(981)
<223> OTHER INFORMATION: n is a, c, g, or t
<220> FEATURE:
<221> NAME/KEY: misc_feature
<222> LOCATION: (985)..(987)
<223> OTHER INFORMATION: n is a, c, g, or t

<400> SEQUENCE: 31

```
gaggtgcagc tggtgcagag cggcggcgac ctggtgaagc ccggcggcag cgtgagactg      60
agctgcgtgg ccagcttcac cttcgactac tacatgaact gggtgagaca ggccccccggc    120
aagggcctgc agtggatcgg cagatggatc ttccccggca gcggcgccac ctactacaac    180
gagagattca tgggcaaggc caccatcagc gccgacaccg ccaagaacac cgcctacatg    240
cagctgaaca gcctgagagc cgaggacacc gccgtgtact actgcctgag aagcgactgg    300
gacgtgggcg acttctgggg ccagggcacc ctggtgaccg tgagcagcgc cagcaccacc    360
gccccccagcg tgttcccccct ggccccccagc tgcggcagcc agagcggcag caccgtggcc    420
ctggcctgcc tggtgagcgg ctacatcccc gagcccgtga ccgtgagctg aacagcgtg    480
agcctgacca gcggcgtgca caccttcccc agcgtgctgc agagcagcgg cctgtacagc    540
ctgagcagca tggtgaccgt gcccagcagc agatggccca gcgagacctt cacctgcaac    600
gtggcccacc ccgccaccaa caccaaggtg acaagcccg tggccaagga gtgcgagtgc    660
aagtgcaact gcaacaactg cccctgcccc ggctgcggcc tgctgggcgg cnnnagcgtg    720
ttcatcttcc ccccaagcc caaggacatc ctggtgaccg ccagaacccc caccgtgacc    780
tgcgtggtgg tgnnnctgga ccccgagaac cccgaggtgc agatcagctg gttcgtggac    840
agcaagcagg tgcagaccgc caacacccag cccagagagg agcagagcnn nnnnnnntac    900
agagtggtga gcgtgctgcc catcggccac caggactggc tgagcggcaa gcagttcaag    960
tgcaaggtga acaacaagnn nctgnnnagc cccatcgagg agatcatcag caagacccccc   1020
ggccaggccc accagcccaa cgtgtacgtg ctgcccccca gcagagacga gatgagcaag   1080
aacaccgtga ccctgacctg cctggtgaag gacttcttcc ccccgagat cgacgtggag    1140
tggcagagca acggccagca ggagcccgag agcaagtaca gaatgacccc cccccagctg   1200
gacgaggacg gcagctactt cctgtacagc aagctgagcg tggacaagag cagatggcag   1260
agaggcgaca ccttcatctg cgccgtgatg cacgaggccc tgcacaacca ctacacccag   1320
atcagcctga gccacagccc cggcaag                                        1347
```

<210> SEQ ID NO 32
<211> LENGTH: 449
<212> TYPE: PRT
<213> ORGANISM: Artificial Sequence
<220> FEATURE:
<223> OTHER INFORMATION: caninized mouse anitbody
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: misc_feature
<222> LOCATION: (297)..(299)
<223> OTHER INFORMATION: Xaa can be any naturally occurring amino acid
<220> FEATURE:

```
<221> NAME/KEY: misc_feature
<222> LOCATION: (327)..(327)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid

<400> SEQUENCE: 32

Glu Val Gln Leu Val Gln Ser Gly Gly Asp Leu Val Lys Pro Gly Gly
1               5                   10                  15

Ser Val Arg Leu Ser Cys Val Ala Ser Phe Thr Phe Asp Tyr Tyr Met
            20                  25                  30

Asn Trp Val Arg Gln Ala Pro Gly Lys Gly Leu Gln Trp Ile Gly Arg
        35                  40                  45

Trp Ile Phe Pro Gly Ser Gly Ala Thr Tyr Tyr Asn Glu Arg Phe Met
    50                  55                  60

Gly Lys Ala Thr Ile Ser Ala Asp Thr Ala Lys Asn Thr Ala Tyr Met
65                  70                  75                  80

Gln Leu Asn Ser Leu Arg Ala Glu Asp Thr Ala Val Tyr Tyr Cys Leu
                85                  90                  95

Arg Ser Asp Trp Asp Val Gly Asp Phe Trp Gly Gln Gly Thr Leu Val
            100                 105                 110

Thr Val Ser Ser Ala Ser Thr Thr Ala Pro Ser Val Phe Pro Leu Ala
        115                 120                 125

Pro Ser Cys Gly Ser Gln Ser Gly Ser Thr Val Ala Leu Ala Cys Leu
    130                 135                 140

Val Ser Gly Tyr Ile Pro Glu Pro Val Thr Val Ser Trp Asn Ser Val
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Thr Asn Thr
        195                 200                 205

Lys Val Asp Lys Pro Val Ala Lys Glu Cys Glu Cys Lys Cys Asn Cys
210                 215                 220

Asn Asn Cys Pro Cys Pro Gly Cys Gly Leu Leu Gly Gly Xaa Ser Val
225                 230                 235                 240

Phe Ile Phe Pro Pro Lys Pro Lys Asp Ile Leu Val Thr Ala Arg Thr
                245                 250                 255

Pro Thr Val Thr Cys Val Val Val Xaa Leu Asp Pro Glu Asn Pro Glu
            260                 265                 270

Val Gln Ile Ser Trp Phe Val Asp Ser Lys Gln Val Gln Thr Ala Asn
        275                 280                 285

Thr Gln Pro Arg Glu Glu Gln Ser Xaa Xaa Xaa Tyr Arg Val Val Ser
290                 295                 300

Val Leu Pro Ile Gly His Gln Asp Trp Leu Ser Gly Lys Gln Phe Lys
305                 310                 315                 320

Cys Lys Val Asn Asn Lys Xaa Leu Xaa Ser Pro Ile Glu Glu Ile Ile
                325                 330                 335

Ser Lys Thr Pro Gly Gln Ala His Gln Pro Asn Val Tyr Val Leu Pro
            340                 345                 350

Pro Ser Arg Asp Glu Met Ser Lys Asn Thr Val Thr Leu Thr Cys Leu
        355                 360                 365
```

```
Val Lys Asp Phe Phe Pro Pro Glu Ile Asp Val Glu Trp Gln Ser Asn
    370                 375                 380

Gly Gln Gln Glu Pro Glu Ser Lys Tyr Arg Met Thr Pro Pro Gln Leu
385                 390                 395                 400

Asp Glu Asp Gly Ser Tyr Phe Leu Tyr Ser Lys Leu Ser Val Asp Lys
                405                 410                 415

Ser Arg Trp Gln Arg Gly Asp Thr Phe Ile Cys Ala Val Met His Glu
            420                 425                 430

Ala Leu His Asn His Tyr Thr Gln Ile Ser Leu Ser His Ser Pro Gly
        435                 440                 445

Lys

<210> SEQ ID NO 33
<211> LENGTH: 1347
<212> TYPE: DNA
<213> ORGANISM: Artificial Sequence
<220> FEATURE:
<223> OTHER INFORMATION: caninized mouse antibody

<400> SEQUENCE: 33
gaggtgcagc tggtgcagag cggcggcgac ctggtgaagc ccggcggcag cgtgagactg      60
agctgcgtgg ccagcggctt caccttcagc tacgccatga gctgggtgag acaggccccc     120
ggcaagggcc tgcagtggat gggcaccatc agcgacggcg gcagctacac ccactacccc     180
gacaacctga tgggcagatt caccttcagc ctggacaccg ccaagaacac cgcctacctg     240
cagctgaaca gcctgagagc cgaggacacc gccgtgtact actgcgccag agagagctac     300
gacggctact acgtggccaa ctggggccag ggcaccctgg tgaccgtgag cagcgccagc     360
accaccgccc ccagcgtgtt cccctggcc ccagctgcg gcagcaccag cggcagcacc       420
gtggccctgg cctgctggt gagcggctac ttccccgagc ccgtgaccgt gagctggaac      480
agcggcagcc tgaccagcgg cgtgcacacc ttccccagcg tgctgcagag cagcggcctg     540
cacagcctga gcagcatggt gaccgtgccc agcagcagat ggcccagcga gaccttcacc     600
tgcaacgtgg tgcaccccgc cagcaacacc aaggtggaca gcccgtgtt caacgagtgc     660 agatgcaccg acaccccccc ctgccccgtg cccgagccc tgggcggccc cagcgtgctg      720
atcttccccc ccaagcccaa ggacatcctg agaatcacca gaacccccga ggtgacctgc     780
gtggtgctgg acctgggcag agaggacccc gaggtgcaga tcagctggtt cgtggacggc     840
aaggaggtgc acaccgccaa gacccagagc agagagcagc agttcaacgg cacctacaga     900
gtggtgagcg tgctgcccat cgagcaccag gactggctga ccggcaagga gttcaagtgc     960
agagtgaacc acatcgacct gcccagcccc atcgagagaa ccatcagcaa ggccagaggc    1020
agagcccaca gcccagcgt gtacgtgctg ccccccagcc caaggagct gagcagcagc      1080 gacaccgtga gcatcacctg cctgatcaag gacttctacc ccccgacat cgacgtggag    1140 tggcagagca acggccagca ggagcccgag agaaagcaca atgaccccc ccccagctg      1200 gacgaggacg gcagctactt cctgtacagc aagctgagcg tggacaagag cagatggcag    1260
cagggcgacc ccttcacctg cgccgtgatg cacgagaccc tgcagaacca ctacacccga    1320
ctgagcctga gccacagccc cggcaag                                       1347

<210> SEQ ID NO 34
<211> LENGTH: 449
<212> TYPE: PRT
<213> ORGANISM: Artificial Sequence
<220> FEATURE:
```

<223> OTHER INFORMATION: caninized mouse antibody

<400> SEQUENCE: 34

```
Glu Val Gln Leu Val Gln Ser Gly Gly Asp Leu Val Lys Pro Gly Gly
1               5                   10                  15

Ser Val Arg Leu Ser Cys Val Ala Ser Gly Phe Thr Phe Ser Tyr Ala
            20                  25                  30

Met Ser Trp Val Arg Gln Ala Pro Gly Lys Gly Leu Gln Trp Met Gly
        35                  40                  45

Thr Ile Ser Asp Gly Gly Ser Tyr Thr His Tyr Pro Asp Asn Leu Met
    50                  55                  60

Gly Arg Phe Thr Phe Ser Leu Asp Thr Ala Lys Asn Thr Ala Tyr Leu
65                  70                  75                  80

Gln Leu Asn Ser Leu Arg Ala Glu Asp Thr Ala Val Tyr Tyr Cys Ala
                85                  90                  95

Arg Glu Ser Tyr Asp Gly Tyr Tyr Val Ala Asn Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu His Ser Leu Ser Ser Met Val Thr Val Pro Ser Ser
            180                 185                 190

Arg Trp Pro Ser Glu Thr Phe Thr Cys Asn Val Val His Pro Ala Ser
        195                 200                 205

Asn Thr Lys Val Asp Lys Pro Val Phe Asn Glu Cys Arg Cys Thr Asp
    210                 215                 220

Thr Pro Pro Cys Pro Val Pro Glu Pro Leu Gly Gly Pro Ser Val Leu
225                 230                 235                 240

Ile Phe Pro Pro Lys Pro Lys Asp Ile Leu Arg Ile Thr Arg Thr Pro
                245                 250                 255

Glu Val Thr Cys Val Val Leu Asp Leu Gly Arg Glu Asp Pro Glu Val
            260                 265                 270

Gln Ile Ser Trp Phe Val Asp Gly Lys Glu Val His Thr Ala Lys Thr
        275                 280                 285

Gln Ser Arg Glu Gln Gln Phe Asn Gly Thr Tyr Arg Val Val Ser Val
    290                 295                 300

Leu Pro Ile Glu His Gln Asp Trp Leu Thr Gly Lys Glu Phe Lys Cys
305                 310                 315                 320

Arg Val Asn His Ile Asp Leu Pro Ser Pro Ile Glu Arg Thr Ile Ser
                325                 330                 335

Lys Ala Arg Gly Arg Ala His Lys Pro Ser Val Tyr Val Leu Pro Pro
            340                 345                 350

Ser Pro Lys Glu Leu Ser Ser Ser Asp Thr Val Ser Ile Thr Cys Leu
        355                 360                 365

Ile Lys Asp Phe Tyr Pro Pro Asp Ile Asp Val Glu Trp Gln Ser Asn
    370                 375                 380

Gly Gln Gln Glu Pro Glu Arg Lys His Arg Met Thr Pro Pro Gln Leu
385                 390                 395                 400
```

Asp Glu Asp Gly Ser Tyr Phe Leu Tyr Ser Lys Leu Ser Val Asp Lys
            405                 410                 415

Ser Arg Trp Gln Gln Gly Asp Pro Phe Thr Cys Ala Val Met His Glu
        420                 425                 430

Thr Leu Gln Asn His Tyr Thr Asp Leu Ser Leu Ser His Ser Pro Gly
    435                 440                 445

Lys

<210> SEQ ID NO 35
<211> LENGTH: 1347
<212> TYPE: DNA
<213> ORGANISM: Artificial Sequence
<220> FEATURE:
<223> OTHER INFORMATION: caninized mouse antibody

<400> SEQUENCE: 35

| | |
|---|---|
| gaggtgcagc tggtgcagag cggcggcgac ctggtgaagc ccggcggcag cgtgagactg | 60 |
| agctgcgtgg ccagcggctt caccttcagc tacgccatga gctgggtgag acaggccccc | 120 |
| ggcaagggcc tgcagtggat gggcaccatc agcgacggcg gcagctacac ccactacccc | 180 |
| gacaacctga tgggcagatt caccttcagc ctggacaccg ccaagaacac cgcctacctg | 240 |
| cagctgaaca gcctgagagc cgaggacacc gccgtgtact actgcgccag agagagctac | 300 |
| gacggctact acgtggccaa ctgggggcca ggcaccctgg tgaccgtgag cagcgccagc | 360 |
| accaccgccc ccagcgtgtt cccccctggcc ccagctgcg gcagcaccag cggcagcacc | 420 |
| gtggccctgg cctgcctggt gagcggctac ttccccgagc ccgtgaccgt gagctggaac | 480 |
| agcggcagcc tgaccagcgg cgtgcacacc ttccccagcg tgctgcagag cagcggcctg | 540 |
| tacagcctga gcagcaccgt gaccgtgccc agcagcagat ggcccagcga gaccttcacc | 600 |
| tgcaacgtgg tgcaccccgc cagcaacacc aaggtggaca gcccgtgcc aaggagagc | 660 |
| acctgcaagt gcatcagccc ctgccccgtg cccgagagcc tgggcggccc cagcgtgttc | 720 |
| atcttccccc ccaagcccaa ggacatcctg agaatcacca gaaccccccga gatcacctgc | 780 |
| gtggtgctgg acctgggcag agaggaccccc gaggtgcaga tcagctggtt cgtggacggc | 840 |
| aaggaggtgc acaccgccaa gacccagccc agagagcagc agttcaacag cacctacaga | 900 |
| gtggtgagcg tgctgcccat cgagcaccag gactggctga ccggcaagga gttcaagtgc | 960 |
| agagtgaacc acatcggcct gcccagcccc atcgagagaa ccatcagcaa ggccagaggc | 1020 |
| caggcccacc agcccagcgt gtacgtgctg ccccccagcc ccaaggagct gagcagcagc | 1080 |
| gacaccgtga ccctgacctg cctgatcaag gacttcttcc cccccgagat cgacgtggag | 1140 |
| tggcagagca cggccagcc cgagcccgag agcaagtacc acaccaccgc ccccccagctg | 1200 |
| gacgaggacg gcagctactt cctgtacagc aagctgagcg tggacaagag cagatggcag | 1260 |
| cagggcgaca ccttcacctg cgccgtgatg cacgaggccc tgcagaacca ctacaccgac | 1320 |
| ctgagcctga gccacagccc cggcaag | 1347 |

<210> SEQ ID NO 36
<211> LENGTH: 449
<212> TYPE: PRT
<213> ORGANISM: Artificial Sequence
<220> FEATURE:
<223> OTHER INFORMATION: caninized mouse antibody

<400> SEQUENCE: 36

Glu Val Gln Leu Val Gln Ser Gly Gly Asp Leu Val Lys Pro Gly Gly
1               5                   10                  15

-continued

```
Ser Val Arg Leu Ser Cys Val Ala Ser Gly Phe Thr Phe Ser Tyr Ala
         20                  25                  30
Met Ser Trp Val Arg Gln Ala Pro Gly Lys Gly Leu Gln Trp Met Gly
         35                  40                  45
Thr Ile Ser Asp Gly Ser Tyr Thr His Tyr Pro Asp Asn Leu Met
 50                  55                  60
Gly Arg Phe Thr Phe Ser Leu Asp Thr Ala Lys Asn Thr Ala Tyr Leu
 65                  70                  75                  80
Gln Leu Asn Ser Leu Arg Ala Glu Asp Thr Ala Val Tyr Tyr Cys Ala
                 85                  90                  95
Arg Glu Ser Tyr Asp Gly Tyr Tyr Val Ala Asn Trp Gly Gln Gly Thr
            100                 105                 110
Leu Val Thr Val Ser Ser Ala Ser Thr Thr Ala Pro Ser Val Phe Pro
            115                 120                 125
Leu Ala Pro Ser Cys Gly Ser Thr Ser Gly Ser Thr Val Ala Leu Ala
        130                 135                 140
Cys Leu Val Ser Gly Tyr Phe Pro Glu Pro Val Thr Val Ser Trp Asn
145                 150                 155                 160
Ser Gly Ser Leu Thr Ser Gly Val His Thr Phe Pro Ser Val Leu Gln
                165                 170                 175
Ser Ser Gly Leu Tyr Ser Leu Ser Ser Thr Val Thr Val Pro Ser Ser
            180                 185                 190
Arg Trp Pro Ser Glu Thr Phe Thr Cys Asn Val Val His Pro Ala Ser
        195                 200                 205
Asn Thr Lys Val Asp Lys Pro Val Pro Lys Glu Ser Thr Cys Lys Cys
        210                 215                 220
Ile Ser Pro Cys Pro Val Pro Glu Ser Leu Gly Gly Pro Ser Val Phe
225                 230                 235                 240
Ile Phe Pro Pro Lys Pro Lys Asp Ile Leu Arg Ile Thr Arg Thr Pro
                245                 250                 255
Glu Ile Thr Cys Val Val Leu Asp Leu Gly Arg Glu Asp Pro Glu Val
            260                 265                 270
Gln Ile Ser Trp Phe Val Asp Gly Lys Glu Val His Thr Ala Lys Thr
        275                 280                 285
Gln Pro Arg Glu Gln Gln Phe Asn Ser Thr Tyr Arg Val Val Ser Val
    290                 295                 300
Leu Pro Ile Glu His Gln Asp Trp Leu Thr Gly Lys Glu Phe Lys Cys
305                 310                 315                 320
Arg Val Asn His Ile Gly Leu Pro Ser Pro Ile Glu Arg Thr Ile Ser
                325                 330                 335
Lys Ala Arg Gly Gln Ala His Gln Pro Ser Val Tyr Val Leu Pro Pro
            340                 345                 350
Ser Pro Lys Glu Leu Ser Ser Asp Thr Val Thr Leu Thr Cys Leu
        355                 360                 365
Ile Lys Asp Phe Phe Pro Pro Glu Ile Asp Val Glu Trp Gln Ser Asn
        370                 375                 380
Gly Gln Pro Glu Pro Glu Ser Lys Tyr His Thr Thr Ala Pro Gln Leu
385                 390                 395                 400
Asp Glu Asp Gly Ser Tyr Phe Leu Tyr Ser Lys Leu Ser Val Asp Lys
                405                 410                 415
Ser Arg Trp Gln Gln Gly Asp Thr Phe Thr Cys Ala Val Met His Glu
            420                 425                 430
```

Ala Leu Gln Asn His Tyr Thr Asp Leu Ser Leu Ser His Ser Pro Gly
        435                 440                 445

Lys

<210> SEQ ID NO 37
<211> LENGTH: 654
<212> TYPE: DNA
<213> ORGANISM: Artificial Sequence
<220> FEATURE:
<223> OTHER INFORMATION: caninized mouse antibody

<400> SEQUENCE: 37

```
gacatcgtga tgacccagac ccccctgagc ctgagcgtga gccccggcga gcccgccagc      60
atgagctgca gagccagcca gagcatcagc aacaacctgc actggtacag acagaagccc     120
ggccagagcc cccaggtgct ggtgaagtac gccagccaga gcatcagcgg cgtgcccgac     180
agattcatcg gcagcggcag cggcaccgac ttcaccctga gaatcagcag agtggaggcc     240
gacgacctgg gcgtgtacta ctgccagcag agcaacagct ggccccagac cttcggccag     300
ggcaccaagc tggagctgaa gagaaacgac gcccagcccg ccgtgtacct gttccagccc     360
agccccgacc agctgcacac cggcagcgcc agcgtggtgt gcctgctgaa cagcttctac     420
cccaaggaca tcaacgtgaa gtggaaggtg gacggcgtga tccaggacac cggcatccag     480
gagagcgtga ccgagcagga cagcaaggac agcacctaca gcctgagcag caccctgacc     540
atgagcagca ccgagtacct gagccacgag ctgtacagct gcgagatcac ccacaagagc     600
ctgcccagca ccctgatcaa gagcttccag agaagcgagt gccagagagt ggac           654
```

<210> SEQ ID NO 38
<211> LENGTH: 218
<212> TYPE: PRT
<213> ORGANISM: Artificial Sequence
<220> FEATURE:
<223> OTHER INFORMATION: caninized mouse antibody

<400> SEQUENCE: 38

Asp Ile Val Met Thr Gln Thr Pro Leu Ser Leu Ser Val Ser Pro Gly
1               5                   10                  15

Glu Pro Ala Ser Met Ser Cys Arg Ala Ser Gln Ser Ile Ser Asn Asn
            20                  25                  30

Leu His Trp Tyr Arg Gln Lys Pro Gly Gln Ser Pro Gln Val Leu Val
        35                  40                  45

Lys Tyr Ala Ser Gln Ser Ile Ser Gly Val Pro Asp Arg Phe Ile Gly
    50                  55                  60

Ser Gly Ser Gly Thr Asp Phe Thr Leu Arg Ile Ser Arg Val Glu Ala
65                  70                  75                  80

Asp Asp Leu Gly Val Tyr Tyr Cys Gln Gln Ser Asn Ser Trp Pro Gln
                85                  90                  95

Thr Phe Gly Gln Gly Thr Lys Leu Glu Leu Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Ser Lys Asp Ser Thr Tyr Ser Leu Ser
                165                 170                 175

Ser Thr Leu Thr Met Ser Ser Thr Glu Tyr Leu Ser His Glu Leu Tyr
            180                 185                 190

Ser Cys Glu Ile Thr His Lys Ser Leu Pro Ser Thr Leu Ile Lys Ser
        195                 200                 205

Phe Gln Arg Ser Glu Cys Gln Arg Val Asp
    210                 215

<210> SEQ ID NO 39
<211> LENGTH: 1341
<212> TYPE: DNA
<213> ORGANISM: Artificial Sequence
<220> FEATURE:
<223> OTHER INFORMATION: caninized mouse antibody

<400> SEQUENCE: 39

| | | |
|---|---|---|
| gaggtgcagc tggtgcagag cggcggcgac ctggtgaagc ccggcggcag cgtgagactg | 60 |
| agctgcgtgg ccagcttcac cttcgactac tacatgaact gggtgagaca ggcccccggc | 120 |
| aagggcctgc agtggatcgg cagatggatc ttccccggca cgcgcgccac ctactacaac | 180 |
| gagagattca tgggcaaggc caccatcagc gccgacaccg ccaagaacac cgcctacatg | 240 |
| cagctgaaca gcctgagagc cgaggacacc gccgtgtact actgcctgag aagcgactgg | 300 |
| gacgtgggcg acttctgggg ccagggcacc ctggtgaccg tgagcagcgc cagcaccacc | 360 |
| gcccccagcg tgttccccct ggcccccagc tgcggcagca ccagcggcag caccgtggcc | 420 |
| ctggcctgcc tggtgagcgg ctacttcccc gagcccgtga ccgtgagctg aacagcggc | 480 |
| agcctgacca gcggcgtgca caccttcccc agcgtgctgc agagcagcgg cctgcacagc | 540 |
| ctgagcagca tggtgaccgt gcccagcagc agatggccca gcgagacctt cacctgcaac | 600 |
| gtggtgcacc ccgccagcaa caccaaggtg gacaagccct gtttcaacga gtgcagatgc | 660 |
| accgacaccc cccctgccc cgtgcccgag ccctgggcg ccccagcgt gctgatcttc | 720 |
| cccccaagc caaggacat cctgagaatc accagaaccc ccgaggtgac ctgcgtggtg | 780 |
| ctggacctgg gcagagagga ccccgaggtg cagatcagct ggttcgtgga cggcaaggag | 840 |
| gtgcacaccg ccaagaccca gagcagagag cagcagttca cggcaccta cagagtggtg | 900 |
| agcgtgctgc ccatcgagca ccaggactgg ctgaccggca aggagttcaa gtgcagagtg | 960 |
| aaccacatcg acctgcccag ccccatcgag agaaccatca gcaaggccag aggcagagcc | 1020 |
| cacaagccca gcgtgtacgt gctgccccc agccccaagg agctgagcag cagcgacacc | 1080 |
| gtgagcatca cctgcctgat caaggacttc taccccccg acatcgacgt ggagtggcag | 1140 |
| agcaacggcc agcaggagcc cgagagaaag cacagaatga cccccccca gctggacgag | 1200 |
| gacggcagct acttcctgta cagcaagctg agcgtggaca gagcagatg gcagcagggc | 1260 |
| gaccccttca cctgcgccgt gatgcacgag accctgcaga ccactacac cgaccстgagc | 1320 |
| ctgagccaca gccccggcaa g | 1341 |

<210> SEQ ID NO 40
<211> LENGTH: 447
<212> TYPE: PRT
<213> ORGANISM: Artificial Sequence
<220> FEATURE:
<223> OTHER INFORMATION: caninized mouse antibody

<400> SEQUENCE: 40

Glu Val Gln Leu Val Gln Ser Gly Gly Asp Leu Val Lys Pro Gly Gly
1               5                   10                  15

-continued

Ser Val Arg Leu Ser Cys Val Ala Ser Phe Thr Phe Asp Tyr Tyr Met
           20                  25                  30

Asn Trp Val Arg Gln Ala Pro Gly Lys Gly Leu Gln Trp Ile Gly Arg
           35                  40                  45

Trp Ile Phe Pro Gly Ser Gly Ala Thr Tyr Tyr Asn Glu Arg Phe Met
       50                  55                  60

Gly Lys Ala Thr Ile Ser Ala Asp Thr Ala Lys Asn Thr Ala Tyr Met
65                  70                  75                  80

Gln Leu Asn Ser Leu Arg Ala Glu Asp Thr Ala Val Tyr Tyr Cys Leu
               85                  90                  95

Arg Ser Asp Trp Asp Val Gly Asp Phe Trp Gly Gln Gly Thr Leu Val
               100                 105                 110

Thr Val Ser Ser Ala Ser Thr Thr Ala Pro Ser Val Phe Pro Leu Ala
           115                 120                 125

Pro Ser Cys Gly Ser Thr Ser Gly Ser Thr Val Ala Leu Ala Cys Leu
       130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
               165                 170                 175

Gly Leu His Ser Leu Ser Ser Met Val Thr Val Pro Ser Ser Arg Trp
               180                 185                 190

Pro Ser Glu Thr Phe Thr Cys Asn Val Val His Pro Ala Ser Asn Thr
           195                 200                 205

Lys Val Asp Lys Pro Val Phe Asn Glu Cys Arg Cys Thr Asp Thr Pro
210                 215                 220

Pro Cys Pro Val Pro Glu Pro Leu Gly Gly Pro Ser Val Leu Ile Phe
225                 230                 235                 240

Pro Pro Lys Pro Lys Asp Ile Leu Arg Ile Thr Arg Thr Pro Glu Val
               245                 250                 255

Thr Cys Val Val Leu Asp Leu Gly Arg Glu Asp Pro Glu Val Gln Ile
               260                 265                 270

Ser Trp Phe Val Asp Gly Lys Glu Val His Thr Ala Lys Thr Gln Ser
       275                 280                 285

Arg Glu Gln Gln Phe Asn Gly Thr Tyr Arg Val Val Ser Val Leu Pro
       290                 295                 300

Ile Glu His Gln Asp Trp Leu Thr Gly Lys Glu Phe Lys Cys Arg Val
305                 310                 315                 320

Asn His Ile Asp Leu Pro Ser Pro Ile Glu Arg Thr Ile Ser Lys Ala
               325                 330                 335

Arg Gly Arg Ala His Lys Pro Ser Val Tyr Val Leu Pro Pro Ser Pro
               340                 345                 350

Lys Glu Leu Ser Ser Ser Asp Thr Val Ser Ile Thr Cys Leu Ile Lys
           355                 360                 365

Asp Phe Tyr Pro Pro Asp Ile Asp Val Glu Trp Gln Ser Asn Gly Gln
       370                 375                 380

Gln Glu Pro Glu Arg Lys His Arg Met Thr Pro Gln Leu Asp Glu
385                 390                 395                 400

Asp Gly Ser Tyr Phe Leu Tyr Ser Lys Leu Ser Val Asp Lys Ser Arg
               405                 410                 415

Trp Gln Gln Gly Asp Pro Phe Thr Cys Ala Val Met His Glu Thr Leu
           420                 425                 430

Gln Asn His Tyr Thr Asp Leu Ser Leu Ser His Ser Pro Gly Lys

<210> SEQ ID NO 41
<211> LENGTH: 1341
<212> TYPE: DNA
<213> ORGANISM: Artificial Sequence
<220> FEATURE:
<223> OTHER INFORMATION: caninized mouse antibody

<400> SEQUENCE: 41

| | | | | | |
|---|---|---|---|---|---|
| gaggtgcagc | tggtgcagag | cggcggcgac | ctggtgaagc | ccggcggcag | cgtgagactg | 60 |
| agctgcgtgg | ccagcttcac | cttcgactac | tacatgaact | gggtgagaca | ggccccccggc | 120 |
| aagggcctgc | agtggatcgg | cagatggatc | ttccccggca | gcggcgccac | ctactacaac | 180 |
| gagagattca | tgggcaaggc | caccatcagc | gccgacaccg | ccaagaacac | cgcctacatg | 240 |
| cagctgaaca | gcctgagagc | cgaggacacc | gccgtgtact | actgcctgag | aagcgactgg | 300 |
| gacgtgggcg | acttctgggg | ccagggcacc | ctggtgaccg | tgagcagcgc | cagcaccacc | 360 |
| gccccccagcg | tgttcccccct | ggccccccagc | tgcggcagca | ccagcggcag | caccgtggcc | 420 |
| ctggcctgcc | tggtgagcgg | ctacttcccc | gagcccgtga | ccgtgagctg | aacagcggc | 480 |
| agcctgacca | gcggcgtgca | caccttcccc | agcgtgctgc | agagcagcgg | cctgtacagc | 540 |
| ctgagcagca | ccgtgaccgt | gcccagcagc | agatggccca | gcgagacctt | cacctgcaac | 600 |
| gtggtgcacc | ccgccagcaa | caccaaggtg | gacaagcccg | tgcccaagga | gagcacctgc | 660 |
| aagtgcatca | gcccctgccc | cgtgcccgag | agcctgggcg | ccccagcgt | gttcatcttc | 720 |
| ccccccaagc | ccaaggacat | cctgagaatc | accagaaccc | ccgagatcac | ctgcgtggtg | 780 |
| ctggacctgg | gcagagagga | ccccgaggtg | cagatcagct | ggttcgtgga | cggcaaggag | 840 |
| gtgcacaccg | ccaagaccca | gcccagagag | cagcagttca | acagcaccta | cagagtggtg | 900 |
| agcgtgctgc | ccatcgagca | ccaggactgg | ctgaccggca | aggagttcaa | gtgcagagtg | 960 |
| aaccacatcg | gcctgcccag | ccccatcgag | agaaccatca | gcaaggccag | aggccaggcc | 1020 |
| caccagccca | gcgtgtacgt | gctgccccccc | agccccaagg | agctgagcag | cagcgacacc | 1080 |
| gtgaccctga | cctgcctgat | caaggacttc | ttccccccccg | agatcgacgt | ggagtggcag | 1140 |
| agcaacggcc | agcccgagcc | cgagagcaag | taccacacca | ccgccccccca | gctggacgag | 1200 |
| gacggcagct | acttcctgta | cagcaagctg | agcgtggaca | gagcagatg | gcagcagggc | 1260 |
| gacaccttca | cctgcgccgt | gatgcacgag | gccctgcaga | accactacac | cgacctgagc | 1320 |
| ctgagccaca | gccccggcaa | g | | | | 1341 |

<210> SEQ ID NO 42
<211> LENGTH: 447
<212> TYPE: PRT
<213> ORGANISM: Artificial Sequence
<220> FEATURE:
<223> OTHER INFORMATION: caninized mouse antibody

<400> SEQUENCE: 42

Glu Val Gln Leu Val Gln Ser Gly Gly Asp Leu Val Lys Pro Gly Gly
1               5                   10                  15

Ser Val Arg Leu Ser Cys Val Ala Ser Phe Thr Phe Asp Tyr Tyr Met
            20                  25                  30

Asn Trp Val Arg Gln Ala Pro Gly Lys Gly Leu Gln Trp Ile Gly Arg
        35                  40                  45

Trp Ile Phe Pro Gly Ser Gly Ala Thr Tyr Tyr Asn Glu Arg Phe Met
    50                  55                  60

Gly Lys Ala Thr Ile Ser Ala Asp Thr Ala Lys Asn Thr Ala Tyr Met
65                  70                  75                  80

Gln Leu Asn Ser Leu Arg Ala Glu Asp Thr Ala Val Tyr Tyr Cys Leu
                85                  90                  95

Arg Ser Asp Trp Asp Val Gly Asp Phe Trp Gly Gln Gly Thr Leu Val
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Thr Val Thr Val Pro Ser Ser Arg Trp
            180                 185                 190

Pro Ser Glu Thr Phe Thr Cys Asn Val Val His Pro Ala Ser Asn Thr
        195                 200                 205

Lys Val Asp Lys Pro Val Pro Lys Glu Ser Thr Cys Lys Cys Ile Ser
210                 215                 220

Pro Cys Pro Val Pro Glu Ser Leu Gly Gly Pro Ser Val Phe Ile Phe
225                 230                 235                 240

Pro Pro Lys Pro Lys Asp Ile Leu Arg Ile Thr Arg Thr Pro Glu Ile
                245                 250                 255

Thr Cys Val Val Leu Asp Leu Gly Arg Glu Asp Pro Glu Val Gln Ile
            260                 265                 270

Ser Trp Phe Val Asp Gly Lys Glu Val His Thr Ala Lys Thr Gln Pro
        275                 280                 285

Arg Glu Gln Gln Phe Asn Ser Thr Tyr Arg Val Val Ser Val Leu Pro
290                 295                 300

Ile Glu His Gln Asp Trp Leu Thr Gly Lys Glu Phe Lys Cys Arg Val
305                 310                 315                 320

Asn His Ile Gly Leu Pro Ser Pro Ile Glu Arg Thr Ile Ser Lys Ala
                325                 330                 335

Arg Gly Gln Ala His Gln Pro Ser Val Tyr Val Leu Pro Pro Ser Pro
            340                 345                 350

Lys Glu Leu Ser Ser Ser Asp Thr Val Thr Leu Thr Cys Leu Ile Lys
        355                 360                 365

Asp Phe Phe Pro Pro Glu Ile Asp Val Glu Trp Gln Ser Asn Gly Gln
370                 375                 380

Pro Glu Pro Glu Ser Lys Tyr His Thr Thr Ala Pro Gln Leu Asp Glu
385                 390                 395                 400

Asp Gly Ser Tyr Phe Leu Tyr Ser Lys Leu Ser Val Asp Lys Ser Arg
                405                 410                 415

Trp Gln Gln Gly Asp Thr Phe Thr Cys Ala Val Met His Glu Ala Leu
            420                 425                 430

Gln Asn His Tyr Thr Asp Leu Ser Leu Ser His Ser Pro Gly Lys
        435                 440                 445

<210> SEQ ID NO 43
<211> LENGTH: 669
<212> TYPE: DNA
<213> ORGANISM: Artificial Sequence
<220> FEATURE:

<223> OTHER INFORMATION: caninized mouse antibody

<400> SEQUENCE: 43

```
gacatcgtga tgacccagac cccctgagc ctgagcgtga gcctgggcga gcccgccagc      60
atcagctgca gaagcagcag aagcctgctg cacaccaacg gcatcaccta cctgagctgg    120
tacagacaga agcccggcca gatccccag ctgctgatct accagatgag caacctggcc    180
agcggcgtgc ccgacagatt cagcggcagc ggcagcggca ccgacttcac cctgagaatc    240
agcagagtgg aggccgacga cgccggcgtg tactactgcg cccagaccct gggcctgccc    300
agaaccttcg gccagggcac caaggtggag atcaagagaa acgacgccca gcccgccgtg    360
tacctgttcc agcccagccc cgaccagctg cacaccggca gcgccagcgt ggtgtgcctg    420
ctgaacagct tctaccccaa ggacatcaac gtgaagtgga aggtggacgg cgtgatccag    480
gacaccggca tccaggagag cgtgaccgag caggacagca aggacagcac ctacagcctg    540
agcagcaccc tgaccatgag cagcaccgag tacctgagcc acgagctgta cagctgcgag    600
atcacccaca gagcctgcc cagcaccctg atcaagagct ccagagaag cgagtgccag    660
agagtggac                                                             669
```

<210> SEQ ID NO 44
<211> LENGTH: 223
<212> TYPE: PRT
<213> ORGANISM: Artificial Sequence
<220> FEATURE:
<223> OTHER INFORMATION: caninized mouse antibody

<400> SEQUENCE: 44

```
Asp Ile Val Met Thr Gln Thr Pro Leu Ser Leu Ser Val Ser Leu Gly
1               5                   10                  15

Glu Pro Ala Ser Ile Ser Cys Arg Ser Ser Arg Ser Leu Leu His Thr
            20                  25                  30

Asn Gly Ile Thr Tyr Leu Ser Trp Tyr Arg Gln Lys Pro Gly Gln Ile
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Ala Gly Val Tyr Tyr Cys Ala Gln Thr
                85                  90                  95

Leu Gly Leu Pro Arg Thr Phe Gly Gln Gly Thr Lys Val Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

<210> SEQ ID NO 45
<211> LENGTH: 17
<212> TYPE: PRT
<213> ORGANISM: Canis familiaris

<400> SEQUENCE: 45

Phe Asn Glu Cys Arg Cys Thr Asp Thr Pro Pro Cys Pro Val Pro Glu
1               5                   10                  15

Pro

<210> SEQ ID NO 46
<211> LENGTH: 22
<212> TYPE: PRT
<213> ORGANISM: Canis familiaris

<400> SEQUENCE: 46

Pro Lys Arg Glu Asn Gly Arg Val Pro Arg Pro Pro Asp Cys Pro Lys
1               5                   10                  15

Cys Pro Ala Pro Glu Met
            20

<210> SEQ ID NO 47
<211> LENGTH: 20
<212> TYPE: PRT
<213> ORGANISM: Canis familiaris

<400> SEQUENCE: 47

Ala Lys Glu Cys Glu Cys Lys Cys Asn Cys Asn Asn Cys Pro Cys Pro
1               5                   10                  15

Gly Cys Gly Leu
            20

<210> SEQ ID NO 48
<211> LENGTH: 17
<212> TYPE: PRT
<213> ORGANISM: Canis familiaris

<400> SEQUENCE: 48

Pro Lys Glu Ser Thr Cys Lys Cys Ile Pro Pro Cys Pro Val Pro Glu
1               5                   10                  15

Ser

<210> SEQ ID NO 49
<211> LENGTH: 795
<212> TYPE: DNA
<213> ORGANISM: Canis familiaris

<400> SEQUENCE: 49
ctagactccc ctgacaggcc ctggagcccg ctcaccttct ccccggcgca gctcacggtg      60
caggagggag agaacgccac gttcacctgc agcctggccg acatcccga cagcttcgtg     120 ctcaactggt accgcctgag cccccgcaac agacggaca agctggccgc cttccaggag     180
gaccgcatcg agccgggccg ggacaggcgc ttccgcgtca tgcggctgcc caacgggcgg     240
gacttccaca tgagcatcgt cgctgcgcgc ctcaacgaca cggcatcta cctgtgcggg     300 gccatctacc tgcccccaa cacacagatc aacgagagtc ccgcgcaga gctctccgtg     360 acggagagaa ccctggagcc ccccacacag agcccagcc ccaccccag actcagcggc     420 cagttgcagg ggctggtcat cggcgtcacg agcgtgctgg tgggtgtcct gctactgctg     480

```
ctgctgacct gggtcctggc cgctgtcttc cccagggcca cccgaggtgc ctgtgtgtgc    540
gggagcgagg acgagcctct gaaggagggc cccgatgcag cgcccgtctt caccctggac    600
tacggggagc tggacttcca gtggcgagag aagacgccgg agccccggc gccctgtgcc    660 ccggagcaga ccgagtatgc caccatcgtc ttcccgggca ggccggcgtc ccgggccgc    720 agggcctcgg ccagcagcct gcaggagcc cagcctccga gccccgagga cggacccggc    780
ctgtggcccc tctga                                                    795
```

<210> SEQ ID NO 50
<211> LENGTH: 264
<212> TYPE: PRT
<213> ORGANISM: Canis familiaris

<400> SEQUENCE: 50

```
Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val Ile Gly Val Thr Ser Val Leu Val Gly Val Leu Leu Leu
145                 150                 155                 160

Leu Leu Thr Trp Val Leu Ala Ala Val Phe Pro Arg Ala Thr Arg Gly
                165                 170                 175

Ala Cys Val Cys Gly Ser Glu Asp Glu Pro Leu Lys Glu Gly Pro Asp
            180                 185                 190

Ala Ala Pro Val Phe Thr Leu Asp Tyr Gly Glu Leu Asp Phe Gln Trp
        195                 200                 205

Arg Glu Lys Thr Pro Glu Pro Pro Ala Pro Cys Ala Pro Glu Gln Thr
    210                 215                 220

Glu Tyr Ala Thr Ile Val Phe Pro Gly Arg Pro Ala Ser Pro Gly Arg
225                 230                 235                 240

Arg Ala Ser Ala Ser Ser Leu Gln Gly Ala Gln Pro Pro Ser Pro Glu
                245                 250                 255

Asp Gly Pro Gly Leu Trp Pro Leu
            260
```

<210> SEQ ID NO 51
<211> LENGTH: 438
<212> TYPE: DNA
<213> ORGANISM: Canis familiaris

<400> SEQUENCE: 51

-continued

| | |
|---|---|
| ctggattccc cgacagacc ctggagccct ctcaccttct ccctgccca gctgaccgtc | 60 |
| caggaaggcg agaatgccac cttcacctgc agcctcgccg acatccccga cagcttcgtg | 120 |
| ctgaactggt acagactgag ccccaggaac cagaccgaca agctggccgc tttccaggag | 180 |
| gacaggatcg aacccggcag ggacaggagg tttagggtca tgaggctgcc caacggcagg | 240 |
| gacttccaca tgtccatcgt ggccgccaga ctgaacgact ccggcatcta cctgtgcggc | 300 |
| gctatctacc tgcccccca cacccagatc aacgagagcc caggggccga actgagcgtg | 360 |
| acagagagaa ccctggaacc tcccacccag agcccttccc ctcctcctag actgagcgga | 420 |
| cagctgcagg gcctggtg | 438 |

<210> SEQ ID NO 52
<211> LENGTH: 146
<212> TYPE: PRT
<213> ORGANISM: Canis familiaris

<400> SEQUENCE: 52

Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val
145

<210> SEQ ID NO 53
<211> LENGTH: 1128
<212> TYPE: DNA
<213> ORGANISM: Artificial Sequence
<220> FEATURE:
<223> OTHER INFORMATION: canine and human fusion

<400> SEQUENCE: 53

| | |
|---|---|
| ctggattccc cgacagacc ctggagccct ctcaccttct ccctgccca gctgaccgtc | 60 |
| caggaaggcg agaatgccac cttcacctgc agcctcgccg acatccccga cagcttcgtg | 120 |
| ctgaactggt acagactgag ccccaggaac cagaccgaca agctggccgc tttccaggag | 180 |
| gacaggatcg aacccggcag ggacaggagg tttagggtca tgaggctgcc caacggcagg | 240 |
| gacttccaca tgtccatcgt ggccgccaga ctgaacgact ccggcatcta cctgtgcggc | 300 |
| gctatctacc tgcccccca cacccagatc aacgagagcc caggggccga actgagcgtg | 360 |
| acagagagaa ccctggaacc tcccacccag agcccttccc ctcctcctag actgagcgga | 420 |
| cagctgcagg gcctggtggg taccgacaaa actcacacat gcccaccgtg cccagcacct | 480 |

```
gaactcctgg ggggaccgtc agtcttcctc ttccccccaa aacccaagga caccctcatg    540
atctcccgga cccctgaggt cacatgcgtg gtggtggacg tgagccacga agaccctgag    600
gtcaagttca actggtacgt ggacggcgtg gaggtgcata atgccaagac aaagccgcgg    660
gaggagcagt acaacagcac gtaccgtgtg gtcagcgtcc tcaccgtcct gcaccaggac    720
tggctgaatg gcaaggagta caagtgcaag gtctccaaca aagccctccc agcccccatc    780
gagaaaacca tctccaaagc caagggcagc cccgagaac acaggtgta cccctgccc    840 ccatcccggg atgagctgac caagaaccag gtcagcctga cctgcctggt caaaggcttc    900
tatcccagcg acatcgccgt ggagtgggag agcaatgggc agccggagaa caactacaag    960
accacgcctc ccgtgctgga ctccgacggc tccttcttcc tctacagcaa gctcaccgtg   1020
gacaagagca ggtggcagca ggggaacgtc ttctcatgct ccgtgatgca tgaggctctg   1080
cacaaccact acacgcagaa gagcctctcc ctgtctccgg gtaaatga               1128
```

<210> SEQ ID NO 54
<211> LENGTH: 375
<212> TYPE: PRT
<213> ORGANISM: Artificial Sequence
<220> FEATURE:
<223> OTHER INFORMATION: canine and human fusion

<400> SEQUENCE: 54

```
Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val Gly Thr Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
```

```
                    245                 250                 255
Pro Ala Pro Ile Glu Lys Thr Ile Ser Lys Ala Lys Gly Gln Pro Arg
            260                 265                 270

Glu Pro Gln Val Tyr Thr Leu Pro Ser Arg Asp Glu Leu Thr Lys
            275                 280             285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys
            370             375

<210> SEQ ID NO 55
<211> LENGTH: 816
<212> TYPE: DNA
<213> ORGANISM: Canis familiaris

<400> SEQUENCE: 55
tttacgatca cagtttctaa ggacctgtat gtggtagagt atggtggcaa tgtgacaatg      60
gaatgcaaat tcccggtgga aaacagttaa acttgtttg cactaatcgt ctactgggaa     120
atggaggata aaaaaattat acaatttgtg aatggaaagg aagacctgaa agttcagcac     180
agcagctaca gccagagggc tcagctattg aaggaccagc tcttcttggg gaaggctgcg     240
cttcagatca cagatgtgag attgcaggat gcaggggttt actgctgctt gatcggctat     300
ggcggtgctg actacaagcg gattactttg aaagttcatg ccccgtaccg caacatcagc     360
caaagaattt ctgtggatcc tgtcacctct gaacatgaac taatgtgtca ggctgagggt     420
taccctgagg ctgaagtcat ctggacaagc agtgaccacc gagtcctgag tggcaaaacc     480
accatcacta attccaatag ggaagagaag cttttcaatg tgaccagcac gctgaacatc     540
aatgcaacag ctaatgagat tttctactgc acttttcaaa gatcaggtcc tgaggaaaac     600
aatactgccg agttggtcat cccagaacga ctgcccgttc agcaagtga gaggactcat      660
ttcatgattc tgggaccttt cctgttgctt cttggtgtag tcctggcagt cactttctgt     720
ctaaaaaaac atgggagaat gatggatgtg gaaaaatgtt gcacccgaga taggaactca     780
aagaaacgaa atgatataca atttgaagag acataa                                816

<210> SEQ ID NO 56
<211> LENGTH: 271
<212> TYPE: PRT
<213> ORGANISM: Canis familiaris

<400> SEQUENCE: 56

Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
            35                  40                  45
```

```
Phe Val Asn Gly Lys Glu Asp Leu Lys Val Gln His Ser Ser Tyr Ser
 50                  55                  60
Gln Arg Ala Gln Leu Leu Lys Asp Gln Leu Phe Leu Gly Lys Ala Ala
 65                  70                  75                  80
Leu Gln Ile Thr Asp Val Arg Leu Gln Asp Ala Gly Val Tyr Cys Cys
                 85                  90                  95
Leu Ile Gly Tyr Gly Gly Ala Asp Tyr Lys Arg Ile Thr Leu Lys Val
            100                 105                 110
His Ala Pro Tyr Arg Asn Ile Ser Gln Arg Ile Ser Val Asp Pro Val
            115                 120                 125
Thr Ser Glu His Glu Leu Met Cys Gln Ala Glu Gly Tyr Pro Glu Ala
130                 135                 140
Glu Val Ile Trp Thr Ser Ser Asp His Arg Val Leu Ser Gly Lys Thr
145                 150                 155                 160
Thr Ile Thr Asn Ser Asn Arg Glu Glu Lys Leu Phe Asn Val Thr Ser
                165                 170                 175
Thr Leu Asn Ile Asn Ala Thr Ala Asn Glu Ile Phe Tyr Cys Thr Phe
            180                 185                 190
Gln Arg Ser Gly Pro Glu Glu Asn Asn Thr Ala Glu Leu Val Ile Pro
            195                 200                 205
Glu Arg Leu Pro Val Pro Ala Ser Glu Arg Thr His Phe Met Ile Leu
210                 215                 220
Gly Pro Phe Leu Leu Leu Leu Gly Val Val Leu Ala Val Thr Phe Cys
225                 230                 235                 240
Leu Lys Lys His Gly Arg Met Met Asp Val Glu Lys Cys Cys Thr Arg
                245                 250                 255
Asp Arg Asn Ser Lys Lys Arg Asn Asp Ile Gln Phe Glu Glu Thr
            260                 265                 270

<210> SEQ ID NO 57
<211> LENGTH: 660
<212> TYPE: DNA
<213> ORGANISM: Canis familiaris

<400> SEQUENCE: 57
tttaccatca ccgtgtccaa ggacctgtac gtggtcgagt acggcggcaa tgtgaccatg     60
gagtgcaagt tccccgtgga gaagcagctg aacctgttcg ccctcatcgt gtactgggag    120
atggaggaca agaagatcat ccagttcgtg aacggcaagg aggacctgaa ggtgcagcac    180
tccagctact cccagagagc ccagctgctg aaggaccagc tgttcctggg caaggccgcc    240
ctgcagatca ccgacgtgag actgcaggac gccggcgtgt attgctgcct gatcggctac    300
ggaggcgccg actacaagag gatcaccctg aaggtgcatg cccctacag gaacatcagc    360 cagaggatca gcgtcgatcc cgtgaccagc gagcacgagc tgatgtgcca agccgagggc    420
tatcccgagg ccgaagtgat ctggaccagc agcgaccaca gggtcctgag cggcaagacc    480
accatcacca acagcaacag ggaggagaag ctgttcaacg tgaccagcac cctcaacatc    540
aacgccaccg ccaacgagat cttctactgc accttccaga ggagcggccc cgaagagaac    600
aacaccgccg agctggtgat ccccgagaga ctgcctgtgc ctgccagcga gaggacccac    660

<210> SEQ ID NO 58
<211> LENGTH: 220
<212> TYPE: PRT
<213> ORGANISM: Canis familiaris

<400> SEQUENCE: 58
```

```
Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80

Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
                100                 105                 110

His Ala Pro Tyr Arg Asn Ile Ser Gln Arg Ile Ser Val Asp Pro Val
            115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
                180                 185                 190

Gln Arg Ser Gly Pro Glu Glu Asn Asn Thr Ala Glu Leu Val Ile Pro
            195                 200                 205

Glu Arg Leu Pro Val Pro Ala Ser Glu Arg Thr His
            210                 215                 220

<210> SEQ ID NO 59
<211> LENGTH: 1350
<212> TYPE: DNA
<213> ORGANISM: Artificial Sequence
<220> FEATURE:
<223> OTHER INFORMATION: canine and human fusion

<400> SEQUENCE: 59
tttaccatca ccgtgtccaa ggacctgtac gtggtcgagt acggcggcaa tgtgaccatg      60
gagtgcaagt tccccgtgga gaagcagctg aacctgttcg ccctcatcgt gtactgggag     120
atggaggaca gaagatcat ccagttcgtg aacggcaagg aggacctgaa ggtgcagcac      180
tccagctact cccagagagc ccagctgctg aaggaccagc tgttcctggg caaggccgcc     240
ctgcagatca ccgacgtgag actgcaggac gccggcgtgt attgctgcct gatcggctac    300
ggaggcgccg actacaagag gatcaccctg aaggtgcatg caccctacag gaacatcagc    360
cagaggatca gcgtcgatcc cgtgaccagc gagcacgagc tgatgtgcca gccgagggc    420 tatcccgagg ccgaagtgat ctggaccagc agcgaccaca gggtcctgag cggcaagacc    480
accatcacca cagcaacag ggaggagaag ctgttcaacg tgaccagcac cctcaacatc     540
aacgccaccg ccaacgagat cttctactgc accttccaga ggagcggccc cgaagagaac    600
aacaccgccg agctggtgat ccccgagaga ctgcctgtgc ctgccagcga gaggacccac    660
ggtaccgaca aaactcacac atgcccaccg tgcccagcac ctgaactcct ggggggaccg    720
tcagtcttcc tcttccccc aaaacccaag gacaccctca tgatctcccg gacccctgag    780
```

```
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccgtg tggtcagcgt cctcaccgtc ctgcaccagg actggctgaa tggcaaggag   960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350
```

<210> SEQ ID NO 60
<211> LENGTH: 449
<212> TYPE: PRT
<213> ORGANISM: Artificial Sequence
<220> FEATURE:
<223> OTHER INFORMATION: canine and human fusion

<400> SEQUENCE: 60

```
Phe Thr Ile Thr Val Ser Lys Asp Leu Tyr Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80

Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His Gly Thr Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
              260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 61
<211> LENGTH: 648
<212> TYPE: DNA
<213> ORGANISM: Canis familiaris

<400> SEQUENCE: 61
ctgggcggcc ccagcgtgct gatcttcccc cccaagccca aggacatcct gagaatcacc      60 agaaccccg aggtgacctg cgtggtgctg gacctgggca gagaggaccc cgaggtgcag     120
atcagctggt tcgtggacgg caaggaggtg cacaccgcca gacccagag cagagagcag     180 cagttcaacg gcacctacag agtggtgagc gtgctgccca tcgagcacca ggactggctg     240
accggcaagg agttcaagtg cagagtgaac cacatcgacc tgcccagccc catcgagaga     300
accatcagca aggccagagg cagagcccac aagcccagcg tgtacgtgct gccccccagc     360
cccaaggagc tgagcagcag cgacaccgtg agcatcacct gcctgatcaa ggacttctac     420
ccccccgaca tcgacgtgga gtggcagagc aacggccagc aggagcccga gaaaagcac     480 agaatgaccc cccccagct ggacgaggac ggcagctact cctgtacag caagctgagc      540 gtggacaaga gcagatggca gcagggcgac cccttcacct gcgccgtgat gcacgagacc     600
ctgcagaacc actacaccga cctgagcctg agccacagcc ccggcaag               648

<210> SEQ ID NO 62
<211> LENGTH: 216
<212> TYPE: PRT
<213> ORGANISM: Canis familiaris

<400> SEQUENCE: 62

Leu Gly Gly Pro Ser Val Leu Ile Phe Pro Pro Lys Pro Lys Asp Ile
1               5                  10                  15

Leu Arg Ile Thr Arg Thr Pro Glu Val Thr Cys Val Val Leu Asp Leu
```

```
                    20                  25                  30
Gly Arg Glu Asp Pro Glu Val Gln Ile Ser Trp Phe Val Asp Gly Lys
                35                  40                  45

Glu Val His Thr Ala Lys Thr Gln Ser Arg Glu Gln Gln Phe Asn Gly
            50                  55                  60

Thr Tyr Arg Val Val Ser Val Leu Pro Ile Glu His Gln Asp Trp Leu
65                  70                  75                  80

Thr Gly Lys Glu Phe Lys Cys Arg Val Asn His Ile Asp Leu Pro Ser
                85                  90                  95

Pro Ile Glu Arg Thr Ile Ser Lys Ala Arg Gly Arg Ala His Lys Pro
            100                 105                 110

Ser Val Tyr Val Leu Pro Pro Ser Pro Lys Glu Leu Ser Ser Ser Asp
        115                 120                 125

Thr Val Ser Ile Thr Cys Leu Ile Lys Asp Phe Tyr Pro Pro Asp Ile
    130                 135                 140

Asp Val Glu Trp Gln Ser Asn Gly Gln Gln Glu Pro Glu Arg Lys His
145                 150                 155                 160

Arg Met Thr Pro Pro Gln Leu Asp Glu Asp Gly Ser Tyr Phe Leu Tyr
                165                 170                 175

Ser Lys Leu Ser Val Asp Lys Ser Arg Trp Gln Gln Gly Asp Pro Phe
            180                 185                 190

Thr Cys Ala Val Met His Glu Thr Leu Gln Asn His Tyr Thr Asp Leu
        195                 200                 205

Ser Leu Ser His Ser Pro Gly Lys
    210                 215

<210> SEQ ID NO 63
<211> LENGTH: 648
<212> TYPE: DNA
<213> ORGANISM: Canis familiaris

<400> SEQUENCE: 63
ctgggcggcc ccagcgtgtt catcttcccc cccaagccca aggacatcct gagaatcacc      60
agaaccccg agatcacctg cgtggtgctg acctgggca gagaggaccc cgaggtgcag      120
atcagctggt tcgtggacgg caaggaggtg cacaccgcca agacccagcc cagagagcag     180
cagttcaaca gcacctacag agtggtgagc gtgctgccca tcgagcacca ggactggctg     240
accggcaagg agttcaagtg cagagtgaac cacatcggcc tgcccagccc catcgagaga     300
accatcagca aggccagagg ccaggcccac cagcccagcg tgtacgtgct gccccccagc     360
cccaaggagc tgagcagcag cgacaccgtg accctgacct gcctgatcaa ggacttcttc     420
ccccccgaga tcgacgtgga gtggcagagc aacggccagc ccgagcccga gagcaagtac     480
cacaccaccg ccccccagct ggacgaggac ggcagctact tcctgtacag caagctgagc     540
gtggacaaga gcagatggca gcagggcgac accttcacct gcgccgtgat gcacgaggcc     600
ctgcagaaca ctacaccga cctgagcctg agccacagcc ccggcaag                   648

<210> SEQ ID NO 64
<211> LENGTH: 216
<212> TYPE: PRT
<213> ORGANISM: Canis familiaris

<400> SEQUENCE: 64

Leu Gly Gly Pro Ser Val Phe Ile Phe Pro Pro Lys Pro Lys Asp Ile
1               5                   10                  15
```

Leu Arg Ile Thr Arg Thr Pro Glu Ile Thr Cys Val Val Leu Asp Leu
            20                  25                  30

Gly Arg Glu Asp Pro Glu Val Gln Ile Ser Trp Phe Val Asp Gly Lys
        35                  40                  45

Glu Val His Thr Ala Lys Thr Gln Pro Arg Glu Gln Gln Phe Asn Ser
    50                  55                  60

Thr Tyr Arg Val Val Ser Val Leu Pro Ile Glu His Gln Asp Trp Leu
65                  70                  75                  80

Thr Gly Lys Glu Phe Lys Cys Arg Val Asn His Ile Gly Leu Pro Ser
                85                  90                  95

Pro Ile Glu Arg Thr Ile Ser Lys Ala Arg Gly Gln Ala His Gln Pro
            100                 105                 110

Ser Val Tyr Val Leu Pro Pro Ser Pro Lys Glu Leu Ser Ser Ser Asp
        115                 120                 125

Thr Val Thr Leu Thr Cys Leu Ile Lys Asp Phe Phe Pro Pro Glu Ile
    130                 135                 140

Asp Val Glu Trp Gln Ser Asn Gly Gln Pro Glu Pro Glu Ser Lys Tyr
145                 150                 155                 160

His Thr Thr Ala Pro Gln Leu Asp Glu Asp Gly Ser Tyr Phe Leu Tyr
                165                 170                 175

Ser Lys Leu Ser Val Asp Lys Ser Arg Trp Gln Gln Gly Asp Thr Phe
            180                 185                 190

Thr Cys Ala Val Met His Glu Ala Leu Gln Asn His Tyr Thr Asp Leu
        195                 200                 205

Ser Leu Ser His Ser Pro Gly Lys
    210                 215

<210> SEQ ID NO 65
<211> LENGTH: 645
<212> TYPE: DNA
<213> ORGANISM: Canis familiaris

<400> SEQUENCE: 65
ctgggcggcc ccagcgtgtt catcttcccc cccaagccca aggacaccct gctgatcgcc      60
agaaccccccg aggtgacctg cgtggtggtg gacctggacc ccgaggaccc cgaggtgcag    120
atcagctggt tcgtggacgg caagcagatg cagaccgcca agacccagcc cagagaggag    180
cagttcaacg gcacctacag agtggtgagc gtgctgccca tcggccacca ggactggctg    240
aagggcaagc agttcacctg caaggtgaac aacaaggccc tgcccagccc catcgagaga    300
accatcagca aggccagagg ccaggcccac cagcccagcg tgtacgtgct gccccccagc    360
agagaggagc tgagcaagaa caccgtgagc ctgacctgcc tgatcaagga cttcttcccc    420
cccgacatcg acgtggagtg gcagagcaac ggccagcagg agcccgagag caagtacaga    480
accaccccccc cccagctgga cgaggacggc agctacttcc tgtacagcaa gctgagcgtg    540
gacaagagca gatggcagag aggcgacacc ttcatctgcg ccgtgatgca cgaggccctg    600
cacaaccact acacccagga gagcctgagc cacagccccg gcaag                    645

<210> SEQ ID NO 66
<211> LENGTH: 215
<212> TYPE: PRT
<213> ORGANISM: Canis familiaris

<400> SEQUENCE: 66

Leu Gly Gly Pro Ser Val Phe Ile Phe Pro Pro Lys Pro Lys Asp Thr
1               5                   10                  15

Leu Leu Ile Ala Arg Thr Pro Glu Val Thr Cys Val Val Asp Leu
            20                  25                  30

Asp Pro Glu Asp Pro Glu Val Gln Ile Ser Trp Phe Val Asp Gly Lys
        35                  40                  45

Gln Met Gln Thr Ala Lys Thr Gln Pro Arg Glu Glu Gln Phe Asn Gly
 50                  55                  60

Thr Tyr Arg Val Val Ser Val Leu Pro Ile Gly His Gln Asp Trp Leu
 65                  70                  75                  80

Lys Gly Lys Gln Phe Thr Cys Lys Val Asn Asn Lys Ala Leu Pro Ser
                85                  90                  95

Pro Ile Glu Arg Thr Ile Ser Lys Ala Arg Gly Gln Ala His Gln Pro
            100                 105                 110

Ser Val Tyr Val Leu Pro Pro Ser Arg Glu Glu Leu Ser Lys Asn Thr
        115                 120                 125

Val Ser Leu Thr Cys Leu Ile Lys Asp Phe Phe Pro Pro Asp Ile Asp
130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Glu Ser
        195                 200                 205

Leu Ser His Ser Pro Gly Lys
    210                 215

<210> SEQ ID NO 67
<211> LENGTH: 645
<212> TYPE: DNA
<213> ORGANISM: Canis familiaris

<400> SEQUENCE: 67
ctgggcggcc ccagcgtgtt catcttcccc cccaagccca aggacatcct ggtgaccgcc    60
agaaccccca ccgtgacctg cgtggtggtg gacctggacc ccgagaaccc cgaggtgcag   120
atcagctggt tcgtggacag caagcaggtg cagaccgcca acaccagcc agagaggag    180 cagagcaacg gcacctacag agtggtgagc gtgctgccca tcggccacca ggactggctg   240
agcggcaagc agttcaagtg caaggtgaac aacaaggccc tgcccagccc catcgaggag   300
atcatcagca gaccccccgg ccaggcccac cagcccaacg tgtacgtgct gccccccagc   360
agagacgaga tgagcaagaa caccgtgacc ctgacctgcc tggtgaagga cttcttcccc   420
cccgagatcg acgtggagtg gcagagcaac ggccagcagg agcccgagag caagtacaga   480 atgaccccc cccagctgga cgaggacggc agctacttcc tgtacagcaa gctgagcgtg   540
gacaagagca gatggcagag aggcgacacc ttcatctgcg ccgtgatgca cgaggccctg   600
cacaaccact acacccagat cagcctgagc acagccccg gcaag              645

<210> SEQ ID NO 68
<211> LENGTH: 215
<212> TYPE: PRT
<213> ORGANISM: Canis familiaris

<400> SEQUENCE: 68

Leu Gly Gly Pro Ser Val Phe Ile Phe Pro Pro Lys Pro Lys Asp Ile

```
  1               5                   10                  15
Leu Val Thr Ala Arg Thr Pro Thr Val Thr Cys Val Val Asp Leu
                20                  25                  30

Asp Pro Glu Asn Pro Glu Val Gln Ile Ser Trp Phe Val Asp Ser Lys
                35                  40                  45

Gln Val Gln Thr Ala Asn Thr Gln Pro Arg Glu Glu Gln Ser Asn Gly
                50                  55                  60

Thr Tyr Arg Val Val Ser Val Leu Pro Ile Gly His Gln Asp Trp Leu
 65                 70                  75                  80

Ser Gly Lys Gln Phe Lys Cys Lys Val Asn Asn Lys Ala Leu Pro Ser
                    85                  90                  95

Pro Ile Glu Glu Ile Ile Ser Lys Thr Pro Gly Gln Ala His Gln Pro
                    100                 105                 110

Asn Val Tyr Val Leu Pro Pro Ser Arg Asp Glu Met Ser Lys Asn Thr
                    115                 120                 125

Val Thr Leu Thr Cys Leu Val Lys Asp Phe Phe Pro Pro Glu Ile Asp
 130                135                 140

Val Glu Trp Gln Ser Asn Gly Gln Gln Glu Pro Glu Ser Lys Tyr Arg
 145                150                 155                 160

Met Thr Pro Pro Gln Leu Asp Glu Asp Gly Ser Tyr Phe Leu Tyr Ser
                    165                 170                 175

Lys Leu Ser Val Asp Lys Ser Arg Trp Gln Arg Gly Asp Thr Phe Ile
                180                 185                 190

Cys Ala Val Met His Glu Ala Leu His Asn His Tyr Thr Gln Ile Ser
                195                 200                 205

Leu Ser His Ser Pro Gly Lys
 210                215

<210> SEQ ID NO 69
<211> LENGTH: 867
<212> TYPE: DNA
<213> ORGANISM: Canis familiaris

<400> SEQUENCE: 69
atggggagcc ggcgggggcc ctggccgctc gtctgggccg tgctgcagct gggctggtgg      60
ccaggatggc tcctagactc ccctgacagg ccctggagcc cgctcacctt ctccccggcg     120
cagctcacgg tgcaggaggg agagaacgcc acgttcacct gcagcctggc cgacatcccc     180
gacagcttcg tgctcaactg gtaccgcctg agccccgcaa ccagacgga caagctggcc      240 gccttccagg aggaccgcat cgagccgggc cgggacaggc gcttccgcgt catgcggctg     300
cccaacgggc gggacttcca catgagcatc gtcgctgcgc cctcaacga cagcggcatc     360 tacctgtgcg ggccatcta cctgcccccc aacacacaga tcaacgagag tccccgcgca     420
gagctctccg tgacggagag aaccctggag ccccccacac agagcccag ccccccaccc     480 agactcagcg ccagttgca ggggctggtc atcggcgtca cgagcgtgct ggtgggtgtc     540
ctgctactgc tgctgctgac ctgggtcctg gccgctgtct tccccagggc cacccgaggt     600
gcctgtgtgt gcgggagcga ggacgagcct ctgaaggagg ccccgatgc agcgcccgtc      660 ttcaccctgg actacgggga gctggacttc agtggcgag agaagacgcc ggagcccccg      720
gcgccctgtg ccccggagca gaccgagtat gccaccatcg tcttcccggg caggccggcg     780
tccccgggcc gcagggcctc ggccagcagc ctgcagggag cccagcctcc gagcccgag      840 gacggacccg gcctgtggcc cctctga                                          867
```

<210> SEQ ID NO 70
<211> LENGTH: 288
<212> TYPE: PRT
<213> ORGANISM: Canis familiaris

<400> SEQUENCE: 70

```
Met Gly Ser Arg Arg Gly Pro Trp Pro Leu Val Trp Ala Val Leu Gln
1               5                   10                  15
Leu Gly Trp Trp Pro Gly Trp Leu Leu Asp Ser Pro Asp Arg Pro Trp
            20                  25                  30
Ser Pro Leu Thr Phe Ser Pro Ala Gln Leu Thr Val Gln Glu Gly Glu
        35                  40                  45
Asn Ala Thr Phe Thr Cys Ser Leu Ala Asp Ile Pro Asp Ser Phe Val
    50                  55                  60
Leu Asn Trp Tyr Arg Leu Ser Pro Arg Asn Gln Thr Asp Lys Leu Ala
65                  70                  75                  80
Ala Phe Gln Glu Asp Arg Ile Glu Pro Gly Arg Asp Arg Arg Phe Arg
                85                  90                  95
Val Met Arg Leu Pro Asn Gly Arg Asp Phe His Met Ser Ile Val Ala
            100                 105                 110
Ala Arg Leu Asn Asp Ser Gly Ile Tyr Leu Cys Gly Ala Ile Tyr Leu
        115                 120                 125
Pro Pro Asn Thr Gln Ile Asn Glu Ser Pro Arg Ala Glu Leu Ser Val
    130                 135                 140
Thr Glu Arg Thr Leu Glu Pro Pro Thr Gln Ser Pro Ser Pro Pro
145                 150                 155                 160
Arg Leu Ser Gly Gln Leu Gln Gly Leu Val Ile Gly Val Thr Ser Val
                165                 170                 175
Leu Val Gly Val Leu Leu Leu Leu Leu Thr Trp Val Leu Ala Ala
            180                 185                 190
Val Phe Pro Arg Ala Thr Arg Gly Ala Cys Val Cys Gly Ser Glu Asp
        195                 200                 205
Glu Pro Leu Lys Glu Gly Pro Asp Ala Ala Pro Val Phe Thr Leu Asp
    210                 215                 220
Tyr Gly Glu Leu Asp Phe Gln Trp Arg Glu Lys Thr Pro Glu Pro Pro
225                 230                 235                 240
Ala Pro Cys Ala Pro Glu Gln Thr Glu Tyr Ala Thr Ile Val Phe Pro
                245                 250                 255
Gly Arg Pro Ala Ser Pro Gly Arg Arg Ala Ser Ala Ser Ser Leu Gln
            260                 265                 270
Gly Ala Gln Pro Pro Ser Pro Glu Asp Gly Pro Gly Leu Trp Pro Leu
        275                 280                 285
```

<210> SEQ ID NO 71
<211> LENGTH: 870
<212> TYPE: DNA
<213> ORGANISM: Canis familiaris

<400> SEQUENCE: 71

```
atgagaatgt ttagtgtctt tacattcatg gcctactgcc atttgctaaa agcatttacg      60
atcacagttt ctaaggacct gtatgtggta gagtatggtg gcaatgtgac aatggaatgc     120
aaattcccgg tggaaaaaca gttaaacttg tttgcactaa tcgtctactg ggaaatggag     180
gataaaaaaa ttatacaatt tgtgaatgga aggaagacc tgaaagttca gcacagcagc      240
tacagccaga gggctcagct attgaaggac cagctcttct tggggaaggc tgcgcttcag     300
```

```
atcacagatg tgagattgca ggatgcaggg gtttactgct gcttgatcgg ctatggcggt      360
gctgactaca agcggattac tttgaaagtt catgccccgt accgcaacat cagccaaaga      420
atttctgtgg atcctgtcac ctctgaacat gaactaatgt gtcaggctga gggttaccct      480
gaggctgaag tcatctggac aagcagtgac caccgagtcc tgagtggcaa aaccaccatc      540
actaattcca atagggaaga gaagcttttc aatgtgacca gcacgctgaa catcaatgca      600
acagctaatg agattttcta ctgcactttt caaagatcag gtcctgagga aaacaatact      660
gccgagttgg tcatcccaga acgactgccc gttccagcaa gtgagaggac tcatttcatg      720
attctgggac ctttcctgtt gcttcttggt gtagtcctgg cagtcacttt ctgtctaaaa      780
aaacatggga gaatgatgga tgtggaaaaa tgttgcaccc gagataggaa ctcaaagaaa      840
cgaaatgata tacaatttga agagacataa                                       870
```

<210> SEQ ID NO 72
<211> LENGTH: 289
<212> TYPE: PRT
<213> ORGANISM: Canis familiaris

<400> SEQUENCE: 72

```
Met Arg Met Phe Ser Val Phe Thr Phe Met Ala Tyr Cys His Leu Leu
1               5                   10                  15

Lys Ala Phe Thr Ile Thr Val Ser Lys Asp Leu Tyr Val Val Glu Tyr
            20                  25                  30

Gly Gly Asn Val Thr Met Glu Cys Lys Phe Pro Val Glu Lys Gln Leu
        35                  40                  45

Asn Leu Phe Ala Leu Ile Val Tyr Trp Glu Met Glu Asp Lys Lys Ile
    50                  55                  60

Ile Gln Phe Val Asn Gly Lys Glu Asp Leu Lys Val Gln His Ser Ser
65                  70                  75                  80

Tyr Ser Gln Arg Ala Gln Leu Leu Lys Asp Gln Leu Phe Leu Gly Lys
                85                  90                  95

Ala Ala Leu Gln Ile Thr Asp Val Arg Leu Gln Asp Ala Gly Val Tyr
            100                 105                 110

Cys Cys Leu Ile Gly Tyr Gly Gly Ala Asp Tyr Lys Arg Ile Thr Leu
        115                 120                 125

Lys Val His Ala Pro Tyr Arg Asn Ile Ser Gln Arg Ile Ser Val Asp
    130                 135                 140

Pro Val Thr Ser Glu His Glu Leu Met Cys Gln Ala Glu Gly Tyr Pro
145                 150                 155                 160

Glu Ala Glu Val Ile Trp Thr Ser Ser Asp His Arg Val Leu Ser Gly
                165                 170                 175

Lys Thr Thr Ile Thr Asn Ser Asn Arg Glu Glu Lys Leu Phe Asn Val
            180                 185                 190

Thr Ser Thr Leu Asn Ile Asn Ala Thr Ala Asn Glu Ile Phe Tyr Cys
        195                 200                 205

Thr Phe Gln Arg Ser Gly Pro Glu Glu Asn Asn Thr Ala Glu Leu Val
    210                 215                 220

Ile Pro Glu Arg Leu Pro Val Pro Ala Ser Glu Arg Thr His Phe Met
225                 230                 235                 240

Ile Leu Gly Pro Phe Leu Leu Leu Gly Val Val Leu Ala Val Thr
                245                 250                 255

Phe Cys Leu Lys Lys His Gly Arg Met Met Asp Val Glu Lys Cys Cys
            260                 265                 270
```

Thr Arg Asp Arg Asn Ser Lys Lys Arg Asn Asp Ile Gln Phe Glu Glu
        275                 280                 285
Thr

<210> SEQ ID NO 73
<211> LENGTH: 357
<212> TYPE: DNA
<213> ORGANISM: Artificial Sequence
<220> FEATURE:
<223> OTHER INFORMATION: caninized mouse

<400> SEQUENCE: 73
gaagtgcagc tggtggagtc tgggggaggc ttagtgaagc ctggagggtc cctgaaactc    60
tcctgtgcag cctctggatt cactttcagt agctatgcca tgtcttgggt tcgccagact   120
ccggacaaga gactggagtg ggtcgcaacc attagtgatg gtggaagtta cacccactac   180
cccgacaatt taatgggccg attcaccatc tccagagaca atgccaagaa caacctgtac   240
ctgcaaatga gccatctgaa gtctgacgac acagccatgt attactgtgc acgagagagc   300
tatgatggtt actacgtggc taactggggc caagggactc tggtcactgt ctcagca      357

<210> SEQ ID NO 74
<211> LENGTH: 119
<212> TYPE: PRT
<213> ORGANISM: Artificial Sequence
<220> FEATURE:
<223> OTHER INFORMATION: caninized mouse

<400> SEQUENCE: 74

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Asp Lys Arg Leu Glu Trp Val
        35                  40                  45

Ala Thr Ile Ser Asp Gly Gly Ser Tyr Thr His Tyr Pro Asp Asn Leu
    50                  55                  60

Met Gly Arg Phe Thr Ile Ser Arg Asp Asn Ala Lys Asn Asn Leu Tyr
65                  70                  75                  80

Leu Gln Met Ser His Leu Lys Ser Asp Asp Thr Ala Met Tyr Tyr Cys
                85                  90                  95

Ala Arg Glu Ser Tyr Asp Gly Tyr Tyr Val Ala Asn Trp Gly Gln Gly
            100                 105                 110

Thr Leu Val Thr Val Ser Ala
        115

<210> SEQ ID NO 75
<211> LENGTH: 321
<212> TYPE: DNA
<213> ORGANISM: Artificial Sequence
<220> FEATURE:
<223> OTHER INFORMATION: caninized mouse

<400> SEQUENCE: 75
gatattgtgc taactcagtc tccagccacc ctgtctgtga atccaggaga tagcgtcagt    60
ctttcctgca gggccagcca aagtattagc aacaacctac actggtatca acaaaaatca   120
catgagtctc caaggcttct catcaagtat gcttcccagt ccatctctgg atcccctcc    180 aggttcagtg gcagtggatc aggacagat ttcactctca gtatcaacag tgtggagact   240

```
gaagattttg gaatgtattt ctgtcaacag agtaacagct ggcctcgagac gttcggtgga      300 ggcaccaagc tggaaatcaa a                                                 321
```

<210> SEQ ID NO 76
<211> LENGTH: 107
<212> TYPE: PRT
<213> ORGANISM: Artificial Sequence
<220> FEATURE:
<223> OTHER INFORMATION: caninized mouse

<400> SEQUENCE: 76

```
Asp Ile Val Leu Thr Gln Ser Pro Ala Thr Leu Ser Val Asn Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Gln
                85                  90                  95

Thr Phe Gly Gly Gly Thr Lys Leu Glu Ile Lys
            100                 105
```

<210> SEQ ID NO 77
<211> LENGTH: 351
<212> TYPE: DNA
<213> ORGANISM: Artificial Sequence
<220> FEATURE:
<223> OTHER INFORMATION: caninized mouse

<400> SEQUENCE: 77

```
caggtccagc tacagcagtc tggacctgag ctggtgaagc ctggggcttc agtgaagata      60
tcctgcaagg cttctggcta caccttcact gactactata tgaattgggt gaaacagagg      120
cctggacagg gacttgagtg gattggatgg atttttcccg gaagtggtgc tacttactac      180
aatgagaggt tcatgggcaa ggccacactt actgtgata aatcttccaa cacagcctac       240
atgttgttca gtagcctgac ctctgaggac tctgcggtct atttctgttt aagatctgac      300
tgggacgtcg ggacttctg gggccaaggc accactctca cagtctcctc a                351
```

<210> SEQ ID NO 78
<211> LENGTH: 117
<212> TYPE: PRT
<213> ORGANISM: Artificial Sequence
<220> FEATURE:
<223> OTHER INFORMATION: caninized mouse

<400> SEQUENCE: 78

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Arg Pro Gly Gln Gly Leu Glu Trp Ile
        35                  40                  45

Gly Trp Ile Phe Pro Gly Ser Gly Ala Thr Tyr Tyr Asn Glu Arg Phe
    50                  55                  60
```

```
Met Gly Lys Ala Thr Leu Thr Val Asp Lys Ser Ser Asn Thr Ala Tyr
 65                  70                  75                  80

Met Leu Phe Ser Ser Leu Thr Ser Glu Asp Ser Ala Val Tyr Phe Cys
                 85                  90                  95

Leu Arg Ser Asp Trp Asp Val Gly Asp Phe Trp Gly Gln Gly Thr Thr
            100                 105                 110

Leu Thr Val Ser Ser
        115

<210> SEQ ID NO 79
<211> LENGTH: 336
<212> TYPE: DNA
<213> ORGANISM: Artificial Sequence
<220> FEATURE:
<223> OTHER INFORMATION: caninized mouse

<400> SEQUENCE: 79
gatattgtga tgacgcaggc tgcattctcc aatccagtca ctcttggaac atcagcttcc      60
atctcctgca ggtctagtag gagtctccta catactaatg gcatcactta tttgtcttgg    120
tttctgcaga agccaggcca gtctcctcag ctcctgattt atcagatgtc caaccttgcc    180
tcaggagtcc cagacaggtt cagtagcagt gggtcaggaa ctgatttcac actgagaatc    240
agtagagtgg aggctgagga tgtgggtatt tattactgtg ctcaaactct aggacttcct    300
cggacgttcg gtggaggcac caagctggaa atcaaa                              336

<210> SEQ ID NO 80
<211> LENGTH: 112
<212> TYPE: PRT
<213> ORGANISM: Artificial Sequence
<220> FEATURE:
<223> OTHER INFORMATION: caninized mouse

<400> SEQUENCE: 80

Asp Ile Val Met Thr Gln Ala Ala Phe Ser Asn Pro Val Thr Leu Gly
 1               5                  10                  15

Thr Ser Ala Ser Ile Ser Cys Arg Ser Ser Arg Ser Leu Leu His Thr
            20                  25                  30

Asn Gly Ile Thr Tyr Leu Ser Trp Phe Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
 65                  70                  75                  80

Ser Arg Val Glu Ala Glu Asp Val Gly Ile Tyr Tyr Cys Ala Gln Thr
                 85                  90                  95

Leu Gly Leu Pro Arg Thr Phe Gly Gly Gly Thr Lys Leu Glu Ile Lys
            100                 105                 110

<210> SEQ ID NO 81
<211> LENGTH: 401
<212> TYPE: PRT
<213> ORGANISM: Artificial Sequence
<220> FEATURE:
<223> OTHER INFORMATION: canine and human fusion

<400> SEQUENCE: 81

Met Asn Phe Leu Leu Ser Trp Val His Trp Ser Leu Ala Leu Leu Leu
 1               5                  10                  15
```

```
Tyr Leu His His Ala Lys Trp Ser Gln Ala Leu Asp Ser Pro Asp Arg
             20                  25                  30

Pro Trp Ser Pro Leu Thr Phe Ser Pro Ala Gln Leu Thr Val Gln Glu
         35                  40                  45

Gly Glu Asn Ala Thr Phe Thr Cys Ser Leu Ala Asp Ile Pro Asp Ser
 50                      55                  60

Phe Val Leu Asn Trp Tyr Arg Leu Ser Pro Arg Asn Gln Thr Asp Lys
 65                  70                  75                  80

Leu Ala Ala Phe Gln Glu Asp Arg Ile Glu Pro Gly Arg Asp Arg Arg
                 85                  90                  95

Phe Arg Val Met Arg Leu Pro Asn Gly Arg Asp Phe His Met Ser Ile
             100                 105                 110

Val Ala Ala Arg Leu Asn Asp Ser Gly Ile Tyr Leu Cys Gly Ala Ile
         115                 120                 125

Tyr Leu Pro Pro Asn Thr Gln Ile Asn Glu Ser Pro Arg Ala Glu Leu
         130                 135                 140

Ser Val Thr Glu Arg Thr Leu Glu Pro Thr Gln Ser Pro Ser Pro Pro
145                 150                 155                 160

Pro Pro Arg Leu Ser Gly Gln Leu Gln Gly Leu Val Gly Thr Asp Lys
             165                 170                 175

Thr His Thr Cys Pro Pro Cys Pro Ala Pro Glu Leu Leu Gly Gly Pro
             180                 185                 190

Ser Val Phe Leu Phe Pro Pro Lys Pro Lys Asp Thr Leu Met Ile Ser
         195                 200                 205

Arg Thr Pro Glu Val Thr Cys Val Val Val Asp Val Ser His Glu Asp
210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
             245                 250                 255

Val Ser Val Leu Thr Val Leu His Gln Asp Trp Leu Asn Gly Lys Glu
             260                 265                 270

Tyr Lys Cys Lys Val Ser Asn Lys Ala Leu Pro Ala Pro Ile Glu Lys
         275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                 325                 330                 335

Ser Asn Gly Gln Pro Glu Asn Asn Tyr Lys Thr Thr Pro Pro Val Leu
             340                 345                 350

Asp Ser Asp Gly Ser Phe Phe Leu Tyr Ser Lys Leu Thr Val Asp Lys
         355                 360                 365

Ser Arg Trp Gln Gln Gly Asn Val Phe Ser Cys Ser Val Met His Glu
         370                 375                 380

Ala Leu His Asn His Tyr Thr Gln Lys Ser Leu Ser Leu Ser Pro Gly
385                 390                 395                 400

Lys

<210> SEQ ID NO 82
<211> LENGTH: 20
<212> TYPE: PRT
<213> ORGANISM: Canis familiaris
```

```
<400> SEQUENCE: 82

Leu Asn Leu Phe Ala Leu Ile Val Tyr Trp Glu Met Glu Asp Lys Lys
1               5                   10                  15

Ile Ile Gln Phe
            20

<210> SEQ ID NO 83
<211> LENGTH: 11
<212> TYPE: PRT
<213> ORGANISM: Canis familiaris

<400> SEQUENCE: 83

Lys Arg Ile Thr Leu Lys Val His Ala Pro Tyr
1               5                   10
```